US008148107B2

(12) United States Patent
Macdonald et al.

(10) Patent No.: US 8,148,107 B2
(45) Date of Patent: Apr. 3, 2012

(54) HIGH AFFINITY HUMAN ANTIBODIES TO HUMAN NERVE GROWTH FACTOR

(75) Inventors: Lynn Macdonald, White Plains, NY (US); Richard Torres, New York, NY (US); Marc R. Morra, Beacon Falls, CT (US); Joel H. Martin, Putnam Valley, NY (US); Joel C. Reinhardt, Mount Kisco, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 13/166,905

(22) Filed: Jun. 23, 2011

(65) Prior Publication Data

US 2011/0256587 A1 Oct. 20, 2011

Related U.S. Application Data

(62) Division of application No. 12/188,330, filed on Aug. 8, 2008, now Pat. No. 7,988,967.

(60) Provisional application No. 60/964,224, filed on Aug. 10, 2007, provisional application No. 60/994,526, filed on Sep. 20, 2007, provisional application No. 61/062,860, filed on Jan. 28, 2008, provisional application No. 61/079,259, filed on Jul. 9, 2008.

(51) Int. Cl.

| | |
|---|---|
| ***C07H 21/04*** | (2006.01) |
| ***C12N 15/13*** | (2006.01) |
| ***C12N 5/10*** | (2006.01) |
| ***C12N 5/07*** | (2010.01) |
| ***C12N 1/21*** | (2006.01) |

(52) U.S. Cl. .................. 435/69.1; 536/23.53; 536/23.1; 435/320.1; 435/336; 435/358; 435/365; 435/252.8; 435/252.3

(58) Field of Classification Search ........................ None
See application file for complete search history.

(56) References Cited

U.S. PATENT DOCUMENTS

| | | | |
|---|---|---|---|
| 5,147,294 | A | 9/1992 | Smith et al. |
| 6,548,062 | B2 | 4/2003 | Buchkovich et al. |
| 7,252,822 | B2 | 8/2007 | Shelton et al. |
| 7,255,860 | B2 | 8/2007 | Shelton et al. |
| 7,425,329 | B2 | 9/2008 | Shelton et al. |
| 7,449,616 | B2 | 11/2008 | Pons et al. |
| 7,569,364 | B2 | 8/2009 | Rosenthal et al. |
| 7,601,352 | B1 | 10/2009 | Novak et al. |
| 7,601,818 | B2 | 10/2009 | Wild et al. |
| 7,655,231 | B2 | 2/2010 | Shelton et al. |
| 7,655,232 | B2 | 2/2010 | Pons et al. |
| 7,727,527 | B2 | 6/2010 | Shelton |
| 7,795,413 | B2 | 9/2010 | Wild, Jr. et al. |
| 2004/0071701 | A1 | 4/2004 | Delafoy et al. |
| 2004/0131615 | A1 | 7/2004 | Shelton et al. |
| 2007/0253930 | A1 | 11/2007 | Roy et al. |
| 2008/0107658 | A1 | 5/2008 | Franks et al. |
| 2009/0041717 | A1 | 2/2009 | MacDonald et al. |
| 2009/0208490 | A1 | 8/2009 | Pavone et al. |
| 2009/0300780 | A1 | 12/2009 | Cattaneo et al. |
| 2010/0278839 | A1 | 11/2010 | Powell et al. |

FOREIGN PATENT DOCUMENTS

| | | |
|---|---|---|
| WO | 02096458 | 12/2002 |
| WO | 2004058184 | 7/2004 |
| WO | 2005019266 | 3/2005 |
| WO | 2006110883 | 10/2006 |
| WO | 2006131951 | 12/2006 |
| WO | 2006131952 | 12/2006 |

OTHER PUBLICATIONS

Wilson-Gerwing et al. (2005) J. Neuroscience 25(3): 758-767.
Casset F et al. (2003) Biochem Biophys Res Comm. 307(1): 198-205.
Chen et al. (1999) J Mol Biol. 293(4): 865-881.
Holm P et al. (2007) Mol Immunol. 44(6): 1075-1084.
MacCallum et al. (1996) J Mol Biol. 262: 732-745.
Padlan et al. (1989) PNAS USA. 86: 5938-5942.
Paul WE. (1993) Fundamental Immunology, Third Edition. Raven Press, New York, pp. 292-295.
Rudikoff et al. (1982) PNAS USA. 79(6): 1979-1983.
Safieh-Garabedian B et al. (1995) Brit J Pharmacol. 115: 1265-1275.
Vajdos FF et al. (2002) J Mol Biol. 320(2): 415-428.

*Primary Examiner* — Elizabeth C Kemmerer
*Assistant Examiner* — Kimberly A Ballard
(74) *Attorney, Agent, or Firm* — Valeta Gregg, Esq.; Veronica Mallon

(57) ABSTRACT

A human antibody or antigen-binding fragment of an antibody which specifically binds human nerve growth factor (NGF) with $K_D$ of 5 pM or less, as measured by surface plasmon resonance, wherein the antibody or fragment thereof binds human NGF with an affinity of about 2-10-fold higher than the antibody or fragment binds rat and mouse NGF. The antibodies are useful in treating pain, including inflammatory pain, post-operative incision pain, neuropathic pain, fracture pain, osteoporotic fracture pain, post-herpetic neuralgia, osteoarthritis, rheumatoid arthritis, cancer pain, pain resulting from burns, gout joint pain, as well as diseases, such as hepatocellular carcinoma, breast cancer, and liver cirrhosis.

16 Claims, No Drawings

```
                              SEQUENCE LISTING


<160> NUMBER OF SEQ ID NOS: 543

<210> SEQ ID NO 1
<211> LENGTH: 847
<212> TYPE: DNA
<213> ORGANISM: Homo sapiens

<400> SEQUENCE: 1

agcgtccgga cccaataaca gttttaccaa gggagcagct ttctatcctg gccacactga     60

ggtgcatagc gtaatgtcca tgttgttcta cactctgatc acagcttttc tgatcggcat    120

acaggcggaa ccacactcag agagcaatgt ccctgcagga cacaccatcc cccaagccca    180

ctggactaaa cttcagcatt cccttgacac tgcccttcgc agagcccgca gcgccccggc    240

agcggcgata gctgcacgcg tggcggggca gacccgcaac attactgtgg accccaggct    300

gtttaaaaag cggcgactcc gttcaccccg tgtgctgttt agcacccagc ctccccgtga    360

agctgcagac actcaggatc tggacttcga ggtcggtggt gctgcccccct tcaacaggac    420

tcacaggagc aagcggtcat catcccatcc catcttccac aggggcgaat tctcggtgtg    480

tgacagtgtc agcgtgtggg ttggggataa gaccaccgcc acagacatca agggcaagga    540

ggtgatggtg ttgggagagg tgagcattaa caacagtgta ttcaaacagt actttttga     600

gaccaagtgc cgggacccaa atcccgttga cagcgggtgc cggggcattg actcaaagca    660

ctggaactca tattgtacca cgactcacac ctttgtcaag gcgctgacca tggatggcaa    720

gcaggctgcc tggcggttta tccggataga tacggcctgt atgtgtgtgc tcagcaggaa    780

ggctgtgaga agagcctgac ctgccgacac gctccctccc cctgcccctt ctacactctc    840

ctgggcc                                                              847


<210> SEQ ID NO 2
<211> LENGTH: 115
<212> TYPE: PRT
<213> ORGANISM: Homo sapiens

<400> SEQUENCE: 2

Ser Ser Ser His Pro Ile Phe His Arg Gly Glu Phe Ser Val Val Ser
1               5                   10                  15

Val Trp Val Gly Asp Lys Thr Thr Ala Thr Asp Ile Lys Gly Lys Glu
            20                  25                  30

Val Met Val Leu Gly Glu Val Asn Ile Asn Asn Ser Val Phe Lys Gln
        35                  40                  45

Tyr Phe Phe Glu Thr Lys Cys Arg Asp Pro Asn Pro Val Asp Ser Gly
    50                  55                  60

Cys Arg Gly Ile Asp Ser Lys His Trp Asn Ser Tyr Cys Thr Thr Thr
65                  70                  75                  80

His Thr Phe Ala Leu Thr Met Asp Gly Lys Gln Ala Ala Trp Arg Phe
                85                  90                  95
```

```
Ile Arg Ile Asp Thr Ala Cys Val Cys Val Leu Ser Arg Lys Ala Val
            100                 105                 110

Arg Arg Ala
        115


<210> SEQ ID NO 3
<211> LENGTH: 349
<212> TYPE: DNA
<213> ORGANISM: Artificial Sequence
<220> FEATURE:
<223> OTHER INFORMATION: Synthetic

<400> SEQUENCE: 3

caggtgcagc tacagcagtg gggcgcagga ctattgaagc cttcggagac cctgtccctc      60

acctgcgctg tctatggtgg atccttcagt gattactact ggagctggat ccgccagccc     120

cccgggaagg ggctggagtg gattggagaa atcaatcata ctggaagcac caattacaac     180

ccgtccctca agagtcgagt caccatatca gtagacacgt cccagaacca cttctccctg     240

aagttgaggt ctgtgaccgc cgcggacacg gctctgtatt actgtgcgag agaggaggtc     300

atctggttcg actcctgggg ccagggaacc ctggtcaccg tctcctcag                 349


<210> SEQ ID NO 4
<211> LENGTH: 116
<212> TYPE: PRT
<213> ORGANISM: Artificial Sequence
<220> FEATURE:
<223> OTHER INFORMATION: Synthetic

<400> SEQUENCE: 4

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Thr Gly Ser Thr Asn Tyr Asn Pro Ser Leu Lys
    50                  55                  60

Ser Arg Val Thr Ile Ser Val Asp Thr Ser Gln Asn His Phe Ser Leu
65                  70                  75                  80

Lys Leu Arg Ser Val Thr Ala Ala Asp Thr Ala Leu Tyr Tyr Cys Ala
                85                  90                  95

Arg Glu Glu Val Ile Trp Phe Asp Ser Trp Gly Gln Gly Thr Leu Val
            100                 105                 110

Thr Val Ser Ser
        115


<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5

ggtggatcct tcagtgatta ctac                                             24


<210> SEQ ID NO 6
<211> LENGTH: 8
<212> TYPE: PRT
<213> ORGANISM: Artificial Sequence
<220> FEATURE:
```

<223> OTHER INFORMATION: Synthetic

<400> SEQUENCE: 6

Gly Gly Ser Phe Ser Asp Tyr Tyr
 1               5

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
atcaatcata ctggaagcac c 21

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

Ile Asn His Thr Gly Ser Thr
 1               5

<210> SEQ ID NO 9
<211> LENGTH: 30
<212> TYPE: DNA
<213> ORGANISM: Artificial Sequence
<220> FEATURE:
<223> OTHER INFORMATION: Synthetic

<400> SEQUENCE: 9
gcgagagagg aggtcatctg gttcgactcc 30

<210> SEQ ID NO 10
<211> LENGTH: 10
<212> TYPE: PRT
<213> ORGANISM: Artificial Sequence
<220> FEATURE:
<223> OTHER INFORMATION: Synthetic

<400> SEQUENCE: 10

Ala Arg Glu Glu Val Ile Trp Phe Asp Ser
 1               5                   10

<210> SEQ ID NO 11
<211> LENGTH: 325
<212> TYPE: DNA
<213> ORGANISM: Artificial Sequence
<220> FEATURE:
<223> OTHER INFORMATION: Synthetic

<400> SEQUENCE: 11
gaaattgtgt tgacgcagtc tccaggcacc ctgtctttgt ctccagggga aagagccacc 60
ctctcctgca gggccagtca gagtgttagt aatagccact tagcctggta ccagcagcaa 120
cctggccagg ctcccaggct cctcatctat agtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggaa gttcactgta cactttcggc 300
caggggacca aactggagat caaac 325

<210> SEQ ID NO 12
<211> LENGTH: 108
<212> TYPE: PRT
<213> ORGANISM: Artificial Sequence
<220> FEATURE:
<223> OTHER INFORMATION: Synthetic

<400> SEQUENCE: 12

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Asn Ser
            20                  25                  30

His Leu Ala Trp Tyr Gln Gln Gln Pro Gly Gln Ala Pro Arg Leu Leu
        35                  40                  45

Ile Tyr Ser Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Tyr Thr Phe Gly Gln Gly Thr Lys Leu Glu Ile Lys
            100                 105
```

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13

```
cagagtgtta gtaatagcca c                                                21
```

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

```
Gln Ser Val Ser Asn Ser His
 1               5
```

<210> SEQ ID NO 15
<211> LENGTH: 9
<212> TYPE: DNA
<213> ORGANISM: Artificial Sequence
<220> FEATURE:
<223> OTHER INFORMATION: Synthetic

<400> SEQUENCE: 15

```
agtgcatcc                                                               9
```

<210> SEQ ID NO 16
<211> LENGTH: 3
<212> TYPE: PRT
<213> ORGANISM: Artificial Sequence
<220> FEATURE:
<223> OTHER INFORMATION: Synthetic

<400> SEQUENCE: 16

```
Ser Ala Ser
 1
```

<210> SEQ ID NO 17
<211> LENGTH: 27
<212> TYPE: DNA
<213> ORGANISM: Artificial Sequence
<220> FEATURE:
<223> OTHER INFORMATION: Synthetic

<400> SEQUENCE: 17
cagcagtatg gaagttcact gtacact 27

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Gln Gln Tyr Gly Ser Ser Leu Tyr Thr
1 5

<210> SEQ ID NO 19
<211> LENGTH: 367
<212> TYPE: DNA
<213> ORGANISM: Artificial Sequence
<220> FEATURE:
<223> OTHER INFORMATION: Synthetic

<400> SEQUENCE: 19
gaggtgcagc tggtggagtc tgggggaggc ttggtacagc cggggggtc cctgagactc 60 tcctgtgcag cctctggatt caccttcagt agctacgaca tacactgggt ccgccaagct 120
acaggaaaag gtctggagtg ggtctcagct atcggtgctg ctggtgacac atactattca 180
ggctccgtga agggccgatt caccatctcc agagaaaatg ccaagaactc cttgtatctt 240
gaaatgaata aattgagagc cggggacacg gctgtgtatt actgtgcaag agagggaacc 300
ggaactacga actactatta tggtatggac gtctggggcc aagggaccac ggtcaccgtc 360
tcctcag 367

<210> SEQ ID NO 20
<211> LENGTH: 122
<212> TYPE: PRT
<213> ORGANISM: Artificial Sequence
<220> FEATURE:
<223> OTHER INFORMATION: Synthetic

<400> SEQUENCE: 20

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Asp Ile His Trp Val Arg Gln Ala Thr Gly Lys Gly Leu Glu Trp Val
35 40 45

Ser Ala Ile Gly Ala Ala Gly Asp Thr Tyr Tyr Ser Gly Ser Val Lys
50 55 60

Gly Arg Phe Thr Ile Ser Arg Glu Asn Ala Lys Asn Ser Leu Tyr Leu
65 70 75 80

Glu Met Asn Lys Leu Arg Ala Gly Asp Thr Ala Val Tyr Tyr Cys Ala
85 90 95

Arg Glu Gly Thr Gly Thr Thr Asn Tyr Tyr Tyr Gly Met Asp Val Trp
100 105 110

```
Gly Gln Gly Thr Thr Val Thr Val Ser Ser
        115                 120


<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21

ggattcacct tcagtagcta cgac                                           24


<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Gly Phe Thr Phe Ser Ser Tyr Asp
 1               5


<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23

atcggtgctg ctggtgacac a                                              21


<210> SEQ ID NO 24
<211> LENGTH: 7
<212> TYPE: PRT
<213> ORGANISM: Artificial Sequence
<220> FEATURE:
<223> OTHER INFORMATION: Synthetic

<400> SEQUENCE: 24

Ile Gly Ala Ala Gly Asp Thr
 1               5


<210> SEQ ID NO 25
<211> LENGTH: 48
<212> TYPE: DNA
<213> ORGANISM: Artificial Sequence
<220> FEATURE:
<223> OTHER INFORMATION: Synthetic

<400> SEQUENCE: 25

gcaagagagg gaaccggaac tacgaactac tattatggta tggacgtc                 48


<210> SEQ ID NO 26
<211> LENGTH: 16
<212> TYPE: PRT
<213> ORGANISM: Artificial Sequence
<220> FEATURE:
<223> OTHER INFORMATION: Synthetic

<400> SEQUENCE: 26

Ala Arg Glu Gly Thr Gly Thr Thr Asn Tyr Tyr Tyr Gly Met Asp Val
 1               5                  10                  15


<210> SEQ ID NO 27
```

<211> LENGTH: 322
<212> TYPE: DNA
<213> ORGANISM: Artificial Sequence
<220> FEATURE:
<223> OTHER INFORMATION: Synthetic

<400> SEQUENCE: 27
gaaattgtat tgacgcagtc tccaggcacc ctgtctttgt ctccagggga aagagccacc 60
ctctcctgca gggccagtca gagtgttagc aggcacttag cctggtacca gcagaactct 120
ggccaggctc ccaggctcct catctatagt gcatccagca gggccactgg catcccagac 180
aggttcagtg gcagggggtc tgggacagac ttcactctca ccatcagcag actggagcct 240
gaggaatttg cagtgtatta ctgtcagcag tatagtagct caccgatcac cttcggccaa 300
gggacacgac tggagattaa tc 322

<210> SEQ ID NO 28
<211> LENGTH: 107
<212> TYPE: PRT
<213> ORGANISM: Artificial Sequence
<220> FEATURE:
<223> OTHER INFORMATION: Synthetic

<400> SEQUENCE: 28

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Arg His
20 25 30

Leu Ala Trp Tyr Gln Gln Asn Ser Gly Gln Ala Pro Arg Leu Leu Ile
35 40 45

Tyr Ser Ala Ser Ser Arg Ala Thr Gly Ile Pro Asp Arg Phe Ser Gly
50 55 60

Arg Gly Ser Gly Thr Asp Phe Thr Leu Thr Ile Ser Arg Leu Glu Pro
65 70 75 80

Glu Glu Phe Ala Val Tyr Tyr Cys Gln Gln Tyr Ser Ser Ser Pro Ile
85 90 95

Thr Phe Gly Gln Gly Thr Arg Leu Glu Ile Asn
100 105

<210> SEQ ID NO 29
<211> LENGTH: 18
<212> TYPE: DNA
<213> ORGANISM: Artificial Sequence
<220> FEATURE:
<223> OTHER INFORMATION: Synthetic

<400> SEQUENCE: 29
cagagtgtta gcaggcac 18

<210> SEQ ID NO 30
<211> LENGTH: 6
<212> TYPE: PRT
<213> ORGANISM: Artificial Sequence
<220> FEATURE:
<223> OTHER INFORMATION: Synthetic

<400> SEQUENCE: 30

Gln Ser Val Ser Arg His
1 5

<210> SEQ ID NO 31
<211> LENGTH: 9
<212> TYPE: DNA

<213> ORGANISM: Artificial Sequence
<220> FEATURE:
<223> OTHER INFORMATION: Synthetic

<400> SEQUENCE: 31 agtgcatcc 9

<210> SEQ ID NO 32
<211> LENGTH: 3
<212> TYPE: PRT
<213> ORGANISM: Artificial Sequence
<220> FEATURE:
<223> OTHER INFORMATION: Synthetic

<400> SEQUENCE: 32

Ser Ala Ser
1

<210> SEQ ID NO 33
<211> LENGTH: 27
<212> TYPE: DNA
<213> ORGANISM: Artificial Sequence
<220> FEATURE:
<223> OTHER INFORMATION: Synthetic

<400> SEQUENCE: 33
cagcagtata gtagctcacc gatcacc 27

<210> SEQ ID NO 34
<211> LENGTH: 9
<212> TYPE: PRT
<213> ORGANISM: Artificial Sequence
<220> FEATURE:
<223> OTHER INFORMATION: Synthetic

<400> SEQUENCE: 34

Gln Gln Tyr Ser Ser Ser Pro Ile Thr
1               5

<210> SEQ ID NO 35
<211> LENGTH: 367
<212> TYPE: DNA
<213> ORGANISM: Artificial Sequence
<220> FEATURE:
<223> OTHER INFORMATION: Synthetic

<400> SEQUENCE: 35
gaggtgcagc tggtggagtc tgggggaggc ttggtacagc ctggggggtc cctgagactc 60
tcctgtgcag cctcgggatt caccttcaga gcctacgaca tgcactgggt ccgccaaaca 120
gcaggaaaag gtctggagtg ggtctcagct attggttctg ctggtgacac atactattca 180
ggctccgtga agggccgatt caccatctcc agagaaaatg ccaagaagtc cttgtatctt 240
caaatgaata gcctgagagc cggggacacg gctgtgtatt tttgtgcaag agaggcaact 300
ggaactacga actactacta cggtatggac gtctggggcc aagggaccac ggtcaccgtc 360
tcctccg 367

<210> SEQ ID NO 36
<211> LENGTH: 122
<212> TYPE: PRT
<213> ORGANISM: Artificial Sequence
<220> FEATURE:
<223> OTHER INFORMATION: Synthetic

<400> SEQUENCE: 36

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Arg Ala Tyr
            20                  25                  30

Asp Met His Trp Val Arg Gln Thr Ala Gly Lys Gly Leu Glu Trp Val
        35                  40                  45

Ser Ala Ile Gly Ser Ala Gly Asp Thr Tyr Tyr Ser Gly Ser Val Lys
    50                  55                  60

Gly Arg Phe Thr Ile Ser Arg Glu Asn Ala Lys Lys Ser Leu Tyr Leu
65                  70                  75                  80

Gln Met Asn Ser Leu Arg Ala Gly Asp Thr Ala Val Tyr Phe Cys Ala
                85                  90                  95

Arg Glu Ala Thr Gly Thr Thr Asn Tyr Tyr Tyr Gly Met Asp Val Trp
            100                 105                 110

Gly Gln Gly Thr Thr Val Thr Val Ser Ser
        115                 120
```

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37

```
ggattcacct tcagagccta cgac                                            24
```

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

```
Gly Phe Thr Phe Arg Ala Tyr Asp
 1               5
```

<210> SEQ ID NO 39
<211> LENGTH: 21
<212> TYPE: DNA
<213> ORGANISM: Artificial Sequence
<220> FEATURE:
<223> OTHER INFORMATION: Synthetic

<400> SEQUENCE: 39

```
attggttctg ctggtgacac a                                               21
```

<210> SEQ ID NO 40
<211> LENGTH: 7
<212> TYPE: PRT
<213> ORGANISM: Artificial Sequence
<220> FEATURE:
<223> OTHER INFORMATION: Synthetic

<400> SEQUENCE: 40

```
Ile Gly Ser Ala Gly Asp Thr
 1               5
```

<210> SEQ ID NO 41
<211> LENGTH: 48
<212> TYPE: DNA
<213> ORGANISM: Artificial Sequence
<220> FEATURE:

<223> OTHER INFORMATION: Synthetic

<400> SEQUENCE: 41
gcaagagagg caactggaac tacgaactac tactacggta tggacgtc 48

<210> SEQ ID NO 42
<211> LENGTH: 16
<212> TYPE: PRT
<213> ORGANISM: Artificial Sequence
<220> FEATURE:
<223> OTHER INFORMATION: Synthetic

<400> SEQUENCE: 42

Ala Arg Glu Ala Thr Gly Thr Thr Asn Tyr Tyr Tyr Gly Met Asp Val
1 5 10 15

<210> SEQ ID NO 43
<211> LENGTH: 325
<212> TYPE: DNA
<213> ORGANISM: Artificial Sequence
<220> FEATURE:
<223> OTHER INFORMATION: Synthetic

<400> SEQUENCE: 43
gaaaatgtgt tgacgcagtc tccaggcacc ctgtctttgt ctccagggga aagaggcacc 60
ctctcctgca gggccagtca gaatattagc ggcaggtcct tagcctggta ccaccagaaa 120
cctggccaga ctcccaaact cctcatcttt ggtgcgtcca ggagggccac tggcatccca 180
gacaggttca gtggcagcgg gtctggaaca gacttcactc tcaccatcag cagactggag 240
cctgaagatt ttgcagtgta ttactgtcag caatatggta gctcaccgat caccttcggc 300
caagggacac gactggagat taaac 325

<210> SEQ ID NO 44
<211> LENGTH: 108
<212> TYPE: PRT
<213> ORGANISM: Artificial Sequence
<220> FEATURE:
<223> OTHER INFORMATION: Synthetic

<400> SEQUENCE: 44

Glu Asn Val Leu Thr Gln Ser Pro Gly Thr Leu Ser Leu Ser Pro Gly
1 5 10 15

Glu Arg Gly Thr Leu Ser Cys Arg Ala Ser Gln Asn Ile Ser Gly Arg
20 25 30

Ser Leu Ala Trp Tyr His Gln Lys Pro Gly Gln Thr Pro Lys Leu Leu
35 40 45

Ile Phe Gly Ala Ser Arg Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Ile Thr Phe Gly Gln Gly Thr Arg Leu Glu Ile Lys
100 105

<210> SEQ ID NO 45
<211> LENGTH: 21
<212> TYPE: DNA
<213> ORGANISM: Artificial Sequence
<220> FEATURE:
<223> OTHER INFORMATION: Synthetic

<400> SEQUENCE: 45
cagaatatta gcggcaggtc c 21

<210> SEQ ID NO 46
<211> LENGTH: 7
<212> TYPE: PRT
<213> ORGANISM: Artificial Sequence
<220> FEATURE:
<223> OTHER INFORMATION: Synthetic

<400> SEQUENCE: 46

Gln Asn Ile Ser Gly Arg Ser
1 5

<210> SEQ ID NO 47
<211> LENGTH: 9
<212> TYPE: DNA
<213> ORGANISM: Artificial Sequence
<220> FEATURE:
<223> OTHER INFORMATION: Synthetic

<400> SEQUENCE: 47 ggtgcgtcc 9

<210> SEQ ID NO 48
<211> LENGTH: 3
<212> TYPE: PRT
<213> ORGANISM: Artificial Sequence
<220> FEATURE:
<223> OTHER INFORMATION: Synthetic

<400> SEQUENCE: 48

Gly Ala Ser
1

<210> SEQ ID NO 49
<211> LENGTH: 27
<212> TYPE: DNA
<213> ORGANISM: Artificial Sequence
<220> FEATURE:
<223> OTHER INFORMATION: Synthetic

<400> SEQUENCE: 49
cagcaatatg gtagctcacc gatcacc 27

<210> SEQ ID NO 50
<211> LENGTH: 9
<212> TYPE: PRT
<213> ORGANISM: Artificial Sequence
<220> FEATURE:
<223> OTHER INFORMATION: Synthetic

<400> SEQUENCE: 50

Gln Gln Tyr Gly Ser Ser Pro Ile Thr
1 5

<210> SEQ ID NO 51
<211> LENGTH: 367
<212> TYPE: DNA
<213> ORGANISM: Artificial Sequence
<220> FEATURE:
<223> OTHER INFORMATION: Synthetic

<400> SEQUENCE: 51
gaggtgcagc tggtggagtc tgggggaggc ttgatacagc ctgggggtc cctgagactc 60 tcctgtgcag cctctggatt caccttcagt aacttcgaca tgcactgggt ccgccaagct 120

```
acaggaaaag gtctggagtg ggtcgcagct attggttctg ctggtgacac atactatccg    180

gactccgtga ggggccgatt caccatctcc agagaaaatg ccaagaactc cttgtttctt    240

caaatgaaca gcctacgaga cggggacacg gctgtgtatt attgtgcaag agagggaact    300

ggaactacga actattacta cggtatggac gtctggggcc aagggaccac ggtcaccgtc    360

tcgtcag                                                              367


<210> SEQ ID NO 52
<211> LENGTH: 122
<212> TYPE: PRT
<213> ORGANISM: Artificial Sequence
<220> FEATURE:
<223> OTHER INFORMATION: Synthetic

<400> SEQUENCE: 52

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Phe Ser Asn Phe
            20                  25                  30

Asp Met His Trp Val Arg Gln Ala Thr Gly Lys Gly Leu Glu Trp Val
        35                  40                  45

Ala Ala Ile Gly Ser Ala Gly Asp Thr Tyr Tyr Pro Asp Ser Val Arg
    50                  55                  60

Gly Arg Phe Thr Ile Ser Arg Glu Asn Ala Lys Asn Ser Leu Phe Leu
65                  70                  75                  80

Gln Met Asn Ser Leu Arg Asp Gly Asp Thr Ala Val Tyr Tyr Cys Ala
                85                  90                  95

Arg Glu Gly Thr Gly Thr Thr Asn Tyr Tyr Tyr Gly Met Asp Val Trp
            100                 105                 110

Gly Gln Gly Thr Thr Val Thr Val Ser Ser
        115                 120


<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53

ggattcacct tcagtaactt cgac                                            24


<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Gly Phe Thr Phe Ser Asn Phe Asp
 1               5


<210> SEQ ID NO 55
<211> LENGTH: 21
<212> TYPE: DNA
<213> ORGANISM: Artificial Sequence
<220> FEATURE:
<223> OTHER INFORMATION: Synthetic

<400> SEQUENCE: 55
```

attggttctg ctggtgacac a 21

<210> SEQ ID NO 56
<211> LENGTH: 7
<212> TYPE: PRT
<213> ORGANISM: Artificial Sequence
<220> FEATURE:
<223> OTHER INFORMATION: Synthetic

<400> SEQUENCE: 56

Ile Gly Ser Ala Gly Asp Thr
1 5

<210> SEQ ID NO 57
<211> LENGTH: 48
<212> TYPE: DNA
<213> ORGANISM: Artificial Sequence
<220> FEATURE:
<223> OTHER INFORMATION: Synthetic

<400> SEQUENCE: 57
gcaagagagg gaactggaac tacgaactat tactacggta tggacgtc 48

<210> SEQ ID NO 58
<211> LENGTH: 16
<212> TYPE: PRT
<213> ORGANISM: Artificial Sequence
<220> FEATURE:
<223> OTHER INFORMATION: Synthetic

<400> SEQUENCE: 58

Ala Arg Glu Gly Thr Gly Thr Thr Asn Tyr Tyr Tyr Gly Met Asp Val
1 5 10 15

<210> SEQ ID NO 59
<211> LENGTH: 322
<212> TYPE: DNA
<213> ORGANISM: Artificial Sequence
<220> FEATURE:
<223> OTHER INFORMATION: Synthetic

<400> SEQUENCE: 59
gaaattatgt tgacgcagtc tccaggcacc ctgtctttgt ctccagggga aagagccacc 60
ctctcctgca gggccagtca gagtgttagc agtcacttag cctggtacca gcagacctct 120
ggccaggctc ccaggctcct catctatggt gcttccagca ggaccactgg catcccagac 180
aggttcagtg gcagtgggtc tgggacagac ttcactctca ccatcagtag actggagcct 240
gaagattttg cagtgtatta ctgtcaacat tatagtaagt caccgatcac cttcggccaa 300
gggacacgac tggagattaa tc 322

<210> SEQ ID NO 60
<211> LENGTH: 107
<212> TYPE: PRT
<213> ORGANISM: Artificial Sequence
<220> FEATURE:
<223> OTHER INFORMATION: Synthetic

<400> SEQUENCE: 60

Glu Ile Met Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser His
20 25 30

Leu Ala Trp Tyr Gln Gln Thr Ser Gly Gln Ala Pro Arg Leu Leu Ile
35 40 45

```
Tyr Gly Ala Ser Ser Arg Thr Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln His Tyr Ser Lys Ser Pro Ile
                85                  90                  95

Thr Phe Gly Gln Gly Thr Arg Leu Glu Ile Asn
            100                 105


<210> SEQ ID NO 61
<211> LENGTH: 18
<212> TYPE: DNA
<213> ORGANISM: Artificial Sequence
<220> FEATURE:
<223> OTHER INFORMATION: Synthetic

<400> SEQUENCE: 61

cagagtgtta gcagtcac                                                   18


<210> SEQ ID NO 62
<211> LENGTH: 6
<212> TYPE: PRT
<213> ORGANISM: Artificial Sequence
<220> FEATURE:
<223> OTHER INFORMATION: Synthetic

<400> SEQUENCE: 62

Gln Ser Val Ser Ser His
 1               5


<210> SEQ ID NO 63
<211> LENGTH: 9
<212> TYPE: DNA
<213> ORGANISM: Artificial Sequence
<220> FEATURE:
<223> OTHER INFORMATION: Synthetic

<400> SEQUENCE: 63

ggtgcttcc                                                              9


<210> SEQ ID NO 64
<211> LENGTH: 3
<212> TYPE: PRT
<213> ORGANISM: Artificial Sequence
<220> FEATURE:
<223> OTHER INFORMATION: Synthetic

<400> SEQUENCE: 64

Gly Ala Ser
 1


<210> SEQ ID NO 65
<211> LENGTH: 27
<212> TYPE: DNA
<213> ORGANISM: Artificial Sequence
<220> FEATURE:
<223> OTHER INFORMATION: Synthetic

<400> SEQUENCE: 65

caacattata gtaagtcacc gatcacc                                         27


<210> SEQ ID NO 66
<211> LENGTH: 9
<212> TYPE: PRT
<213> ORGANISM: Artificial Sequence
```

<220> FEATURE:
<223> OTHER INFORMATION: Synthetic

<400> SEQUENCE: 66

```
Gln His Tyr Ser Lys Ser Pro Ile Thr
 1               5
```

<210> SEQ ID NO 67
<211> LENGTH: 367
<212> TYPE: DNA
<213> ORGANISM: Artificial Sequence
<220> FEATURE:
<223> OTHER INFORMATION: Synthetic

<400> SEQUENCE: 67

```
gaggtgcagc tggtggagtc tgggggaggc ttggaacagc ctggggggtc cctgagactc     60

tcctgtgtag cctctggatt caccttcagt aactacgaca tgcactgggt ccgccaagcc    120

acaggaaaag gtctggagtg ggtctcagct attggtgctg ctggtgacac atactattca    180

ggctccgtga agggccgatt caccatcgcc agagaaaatg gcaagaactc cctgtatctt    240

caaatgaatg gcctgagagc cggggacacg gctgtgtatt actgtgcaag agagggaact    300

ggaactacga actactacta cggtatggac gtctggggcc aagggaccac ggtcaccgtc    360

tcctctg                                                              367
```

<210> SEQ ID NO 68
<211> LENGTH: 122
<212> TYPE: PRT
<213> ORGANISM: Artificial Sequence
<220> FEATURE:
<223> OTHER INFORMATION: Synthetic

<400> SEQUENCE: 68

```
Glu Val Gln Leu Val Glu Ser Gly Gly Gly Leu Glu Gln Pro Gly Gly
 1               5                  10                  15

Ser Leu Arg Leu Ser Cys Val Ala Ser Gly Phe Thr Phe Ser Asn Tyr
            20                  25                  30

Asp Met His Trp Val Arg Gln Ala Thr Gly Lys Gly Leu Glu Trp Val
        35                  40                  45

Ser Ala Ile Gly Ala Ala Gly Asp Thr Tyr Tyr Ser Gly Ser Val Lys
    50                  55                  60

Gly Arg Phe Thr Ile Ala Arg Glu Asn Gly Lys Asn Ser Leu Tyr Leu
65                  70                  75                  80

Gln Met Asn Gly Leu Arg Ala Gly Asp Thr Ala Val Tyr Tyr Cys Ala
                85                  90                  95

Arg Glu Gly Thr Gly Thr Thr Asn Tyr Tyr Tyr Gly Met Asp Val Trp
            100                 105                 110

Gly Gln Gly Thr Thr Val Thr Val Ser Ser
        115                 120
```

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69

```
ggattcacct tcagtaacta cgac                                            24
```

<210> SEQ ID NO 70

<211> LENGTH: 8
<212> TYPE: PRT
<213> ORGANISM: Artificial Sequence
<220> FEATURE:
<223> OTHER INFORMATION: Synthetic

<400> SEQUENCE: 70

Gly Phe Thr Phe Ser Asn Tyr Asp
1 5

<210> SEQ ID NO 71
<211> LENGTH: 21
<212> TYPE: DNA
<213> ORGANISM: Artificial Sequence
<220> FEATURE:
<223> OTHER INFORMATION: Synthetic

<400> SEQUENCE: 71
attggtgctg ctggtgacac a 21

<210> SEQ ID NO 72
<211> LENGTH: 7
<212> TYPE: PRT
<213> ORGANISM: Artificial Sequence
<220> FEATURE:
<223> OTHER INFORMATION: Synthetic

<400> SEQUENCE: 72

Ile Gly Ala Ala Gly Asp Thr
1 5

<210> SEQ ID NO 73
<211> LENGTH: 48
<212> TYPE: DNA
<213> ORGANISM: Artificial Sequence
<220> FEATURE:
<223> OTHER INFORMATION: Synthetic

<400> SEQUENCE: 73
gcaagagagg gaactggaac tacgaactac tactacggta tggacgtc 48

<210> SEQ ID NO 74
<211> LENGTH: 16
<212> TYPE: PRT
<213> ORGANISM: Artificial Sequence
<220> FEATURE:
<223> OTHER INFORMATION: Synthetic

<400> SEQUENCE: 74

Ala Arg Glu Gly Thr Gly Thr Thr Asn Tyr Tyr Tyr Gly Met Asp Val
1 5 10 15

<210> SEQ ID NO 75
<211> LENGTH: 322
<212> TYPE: DNA
<213> ORGANISM: Artificial Sequence
<220> FEATURE:
<223> OTHER INFORMATION: Synthetic

<400> SEQUENCE: 75
gaaattgtgt tgacgcagtc tccagacacc ctgtcgttgt ctctagggga gagagccatc 60
ctctcctgca gggccagtca gagtgttagc agctacttag cctggtacca gcagacctct 120
ggccaggctc ccaggctcct catctttggt gcgtccagca gggccactgg catcccagac 180
aggttcagtg gcagtgggtc tgggacagac ttcactctca ccatcaacag actggaacct 240
ggagattttg cagtgtatta ctgtcagcag tatgctagtt caccgatcac cttcggccaa 300

```
gggacacgac tggatattaa tc                                          322


<210> SEQ ID NO 76
<211> LENGTH: 107
<212> TYPE: PRT
<213> ORGANISM: Artificial Sequence
<220> FEATURE:
<223> OTHER INFORMATION: Synthetic

<400> SEQUENCE: 76

Glu Ile Val Leu Thr Gln Ser Pro Asp Thr Leu Ser Leu Ser Leu Gly
 1               5                  10                  15

Glu Arg Ala Ile Leu Ser Cys Arg Ala Ser Gln Ser Val Ser Ser Tyr
            20                  25                  30

Leu Ala Trp Tyr Gln Gln Thr Ser Gly Gln Ala Pro Arg Leu Leu Ile
        35                  40                  45

Phe Gly Ala Ser Ser Arg Ala Thr Gly Ile Pro Asp Arg Phe Ser Gly
    50                  55                  60

Ser Gly Ser Gly Thr Asp Phe Thr Leu Thr Ile Asn Arg Leu Glu Pro
65                  70                  75                  80

Gly Asp Phe Ala Val Tyr Tyr Cys Gln Gln Tyr Ala Ser Ser Pro Ile
                85                  90                  95

Thr Phe Gly Gln Gly Thr Arg Leu Asp Ile Asn
            100                 105


<210> SEQ ID NO 77
<211> LENGTH: 18
<212> TYPE: DNA
<213> ORGANISM: Artificial Sequence
<220> FEATURE:
<223> OTHER INFORMATION: Synthetic

<400> SEQUENCE: 77

cagagtgtta gcagctac                                                18


<210> SEQ ID NO 78
<211> LENGTH: 6
<212> TYPE: PRT
<213> ORGANISM: Artificial Sequence
<220> FEATURE:
<223> OTHER INFORMATION: Synthetic

<400> SEQUENCE: 78

Gln Ser Val Ser Ser Tyr
 1               5


<210> SEQ ID NO 79
<211> LENGTH: 9
<212> TYPE: DNA
<213> ORGANISM: Artificial Sequence
<220> FEATURE:
<223> OTHER INFORMATION: Synthetic

<400> SEQUENCE: 79

ggtgcgtcc                                                           9


<210> SEQ ID NO 80
<211> LENGTH: 3
<212> TYPE: PRT
<213> ORGANISM: Artificial Sequence
<220> FEATURE:
<223> OTHER INFORMATION: Synthetic

<400> SEQUENCE: 80
```

```
Gly Ala Ser
 1


<210> SEQ ID NO 81
<211> LENGTH: 27
<212> TYPE: DNA
<213> ORGANISM: Artificial Sequence
<220> FEATURE:
<223> OTHER INFORMATION: Synthetic

<400> SEQUENCE: 81

cagcagtatg ctagttcacc gatcacc                                          27


<210> SEQ ID NO 82
<211> LENGTH: 9
<212> TYPE: PRT
<213> ORGANISM: Artificial Sequence
<220> FEATURE:
<223> OTHER INFORMATION: Synthetic

<400> SEQUENCE: 82

Gln Gln Tyr Ala Ser Ser Pro Ile Thr
 1               5


<210> SEQ ID NO 83
<211> LENGTH: 357
<212> TYPE: DNA
<213> ORGANISM: Artificial Sequence
<220> FEATURE:
<223> OTHER INFORMATION: Synthetic

<400> SEQUENCE: 83

caggtgcagc tggtacagtc tggggctgag gtgaagaagc ctggggcctc agtgaaggtc     60

tcctgcaagg tttccggatt caccctcact gaattatcca ttcactgggt gcgacaggct    120

cctggaaaag ggcttgagtg gatgggaggt tttgatcctg aagatggtga aacaatctac    180

gcacagaagt tccagggcag agtcaccatg accgaggaca catctacaga cacagcctac    240

atggagctga ccagcctgag atcggaagac acggccgtgt attactgttc aacgattttt    300

ggagtggtta ccaactttga caactggggc cagggaaccc tggtcaccgt ctcctca       357


<210> SEQ ID NO 84
<211> LENGTH: 119
<212> TYPE: PRT
<213> ORGANISM: Artificial Sequence
<220> FEATURE:
<223> OTHER INFORMATION: Synthetic

<400> SEQUENCE: 84

Gln Val Gln Leu Val Gln Ser Gly Ala Glu Val Lys Lys Pro Gly Ala
 1               5                  10                  15

Ser Val Lys Val Ser Cys Lys Val Ser Gly Phe Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Thr Ser Leu Arg Ser Glu Asp Thr Ala Val Tyr Tyr Cys
                85                  90                  95

Ser Thr Ile Phe Gly Val Val Thr Asn Phe Asp Asn Trp Gly Gln Gly
```

```
        100                 105                 110

Thr Leu Val Thr Val Ser Ser
        115


<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85

ggattcaccc tcactgaatt atcc                                            24


<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Gly Phe Thr Leu Thr Glu Leu Ser
 1               5


<210> SEQ ID NO 87
<211> LENGTH: 24
<212> TYPE: DNA
<213> ORGANISM: Artificial Sequence
<220> FEATURE:
<223> OTHER INFORMATION: Synthetic

<400> SEQUENCE: 87

tttgatcctg aagatggtga aaca                                            24


<210> SEQ ID NO 88
<211> LENGTH: 8
<212> TYPE: PRT
<213> ORGANISM: Artificial Sequence
<220> FEATURE:
<223> OTHER INFORMATION: Synthetic

<400> SEQUENCE: 88

Phe Asp Pro Glu Asp Gly Glu Thr
 1               5


<210> SEQ ID NO 89
<211> LENGTH: 36
<212> TYPE: DNA
<213> ORGANISM: Artificial Sequence
<220> FEATURE:
<223> OTHER INFORMATION: Synthetic

<400> SEQUENCE: 89

tcaacgattt ttggagtggt taccaacttt gacaac                               36


<210> SEQ ID NO 90
<211> LENGTH: 12
<212> TYPE: PRT
<213> ORGANISM: Artificial Sequence
<220> FEATURE:
<223> OTHER INFORMATION: Synthetic

<400> SEQUENCE: 90

Ser Thr Ile Phe Gly Val Val Thr Asn Phe Asp Asn
 1               5                   10
```

<210> SEQ ID NO 91
<211> LENGTH: 324
<212> TYPE: DNA
<213> ORGANISM: Artificial Sequence
<220> FEATURE:
<223> OTHER INFORMATION: Synthetic

<400> SEQUENCE: 91

```
gacatccgga tgacccagtc tccatcctcc ctgtctgcat ctgcaggaga cagagtcacc     60

atcacttgcc gggcaagtca ggccattaga aatgatttag gctggtatca gcagaaacca    120

gggaaagccc ctaagcgcct gatctatgct gcattcaatt tgcaaagtgg ggtcccatca    180

agattcagcg gcagtggatc tgggacagaa ttcactctca caatcagtag cctgcagcct    240

gaagatcttg caagttatta ctgtcaacag tataatagat acccgtggac gttcggccaa    300

gggaccaagc tggagatcaa acga                                           324
```

<210> SEQ ID NO 92
<211> LENGTH: 107
<212> TYPE: PRT
<213> ORGANISM: Artificial Sequence
<220> FEATURE:
<223> OTHER INFORMATION: Synthetic

<400> SEQUENCE: 92

```
Asp Ile Arg Met Thr Gln Ser Pro Ser Ser Leu Ser Ala Ser Ala Gly
 1               5                  10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Phe Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Leu Ala Ser Tyr Tyr Cys Gln Gln Tyr Asn Arg Tyr Pro Trp
                85                  90                  95

Thr Phe Gly Gln Gly Thr Lys Leu Glu Ile Lys
            100                 105
```

<210> SEQ ID NO 93
<211> LENGTH: 18
<212> TYPE: DNA
<213> ORGANISM: Artificial Sequence
<220> FEATURE:
<223> OTHER INFORMATION: Synthetic

<400> SEQUENCE: 93

```
caggccatta gaaatgat                                                   18
```

<210> SEQ ID NO 94
<211> LENGTH: 6
<212> TYPE: PRT
<213> ORGANISM: Artificial Sequence
<220> FEATURE:
<223> OTHER INFORMATION: Synthetic

<400> SEQUENCE: 94

```
Gln Ala Ile Arg Asn Asp
 1               5
```

<210> SEQ ID NO 95

<211> LENGTH: 9
<212> TYPE: DNA
<213> ORGANISM: Artificial Sequence
<220> FEATURE:
<223> OTHER INFORMATION: Synthetic

<400> SEQUENCE: 95 gctgcattc 9

<210> SEQ ID NO 96
<211> LENGTH: 3
<212> TYPE: PRT
<213> ORGANISM: Artificial Sequence
<220> FEATURE:
<223> OTHER INFORMATION: Synthetic

<400> SEQUENCE: 96

Ala Ala Phe
1

<210> SEQ ID NO 97
<211> LENGTH: 27
<212> TYPE: DNA
<213> ORGANISM: Artificial Sequence
<220> FEATURE:
<223> OTHER INFORMATION: Synthetic

<400> SEQUENCE: 97
caacagtata atagataccc gtggacg 27

<210> SEQ ID NO 98
<211> LENGTH: 9
<212> TYPE: PRT
<213> ORGANISM: Artificial Sequence
<220> FEATURE:
<223> OTHER INFORMATION: Synthetic

<400> SEQUENCE: 98

Gln Gln Tyr Asn Arg Tyr Pro Trp Thr
1 5

<210> SEQ ID NO 99
<211> LENGTH: 357
<212> TYPE: DNA
<213> ORGANISM: Artificial Sequence
<220> FEATURE:
<223> OTHER INFORMATION: Synthetic

<400> SEQUENCE: 99
caggtgcagc tggtgcagtc cggcgccgag gtgaagaagc ccggcgcctc cgtgaaggtg 60
tcctgcaagg tgtccggctt caccctgacc gagctgtcca tgcactgggt gcggcaggcc 120
cccggcaagg gcctggagtg gatgggcggc ttcgaccccg aggacggcga gaccatctac 180
gcccagaagt tccagggccg ggtgaccatg accgaggaca cctccaccga caccgcctac 240
atggagctgt cctccctgcg gtccgaggac accgccgtgt actactgctc caccatcttc 300
ggcgtggtga ccaacttcga caactggggc cagggcaccc tggtgaccgt gtcctcc 357

<210> SEQ ID NO 100
<211> LENGTH: 119
<212> TYPE: PRT
<213> ORGANISM: Artificial Sequence
<220> FEATURE:
<223> OTHER INFORMATION: Synthetic

<400> SEQUENCE: 100

```
Gln Val Gln Leu Val Gln Ser Gly Ala Glu Val Lys Lys Pro Gly Ala
 1               5                  10                  15

Ser Val Lys Val Ser Cys Lys Val Ser Gly Phe Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ser Thr Ile Phe Gly Val Val Thr Asn Phe Asp Asn Trp Gly Gln Gly
            100                 105                 110

Thr Leu Val Thr Val Ser Ser
        115


<210> SEQ ID NO 101
<211> LENGTH: 324
<212> TYPE: DNA
<213> ORGANISM: Artificial Sequence
<220> FEATURE:
<223> OTHER INFORMATION: Synthetic

<400> SEQUENCE: 101

gacatccaga tgacccagtc cccctcctcc ctgtccgcct ccgtgggcga ccgggtgacc      60

atcacctgcc gggcctccca ggccatccgg aacgacctgg gctggtacca gcagaagccc     120

ggcaaggccc ccaagcggct gatctacgcc gccttcaacc tgcagtccgg cgtgccctcc     180

cggttctccg gctccggctc cggcaccgag ttcaccctga ccatctcctc cctgcagccc     240

gaggacttcg ccacctacta ctgccagcag tacaaccggt acccctggac cttcggccag     300

ggcaccaagg tggagatcaa gcgg                                            324


<210> SEQ ID NO 102
<211> LENGTH: 108
<212> TYPE: PRT
<213> ORGANISM: Artificial Sequence
<220> FEATURE:
<223> OTHER INFORMATION: Synthetic

<400> SEQUENCE: 102

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Phe Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Arg Tyr Pro Trp
                85                  90                  95

Thr Phe Gly Gln Gly Thr Lys Val Glu Ile Lys Arg
            100                 105


<210> SEQ ID NO 103
<211> LENGTH: 357
```

<212> TYPE: DNA
<213> ORGANISM: Artificial Sequence
<220> FEATURE:
<223> OTHER INFORMATION: Synthetic

<400> SEQUENCE: 103

```
caggtgcagc tggtgcagtc cggcgccgag gtgaagaagc ccggcgcctc cgtgaaggtg     60

tcctgcaagg tgtccggctt caccctgacc gagctgtcca tgcactgggt gcggcaggcc    120

cccggcaagg gcctggagtg gatgggcggc ttcgaccccg aggacggcga gaccatctac    180

gcccagaagt tccagggccg ggtgaccatg accgaggaca cctccaccga caccgcctac    240

atggagctgt cctccctgcg gtccgaggac accgccgtgt actactgctc caccatcttc    300

ggcgtggtga ccaacttcga caactggggc cagggcaccc tggtgaccgt gtcctcc       357
```

<210> SEQ ID NO 104
<211> LENGTH: 119
<212> TYPE: PRT
<213> ORGANISM: Artificial Sequence
<220> FEATURE:
<223> OTHER INFORMATION: Synthetic

<400> SEQUENCE: 104

```
Gln Val Gln Leu Val Gln Ser Gly Ala Glu Val Lys Lys Pro Gly Ala
 1               5                  10                  15

Ser Val Lys Val Ser Cys Lys Val Ser Gly Phe Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ser Thr Ile Phe Gly Val Val Thr Asn Phe Asp Asn Trp Gly Gln Gly
            100                 105                 110

Thr Leu Val Thr Val Ser Ser
        115
```

<210> SEQ ID NO 105
<211> LENGTH: 324
<212> TYPE: DNA
<213> ORGANISM: Artificial Sequence
<220> FEATURE:
<223> OTHER INFORMATION: Synthetic

<400> SEQUENCE: 105

```
gacatccaga tgacccagtc cccctcctcc ctgtccgcct ccgtgggcga ccgggtgacc     60

atcacctgcc gggcctccca ggccatccgg aacgacctgg gctggtacca gcagaagccc    120

ggcaaggccc ccaagcggct gatctacgcc gccttctccc tgcagtccgg cgtgccctcc    180

cggttctccg gctccggctc cggcaccgag ttcaccctga ccatctcctc cctgcagccc    240

gaggacttcg ccacctacta ctgccagcag tacaaccggt accccctggac cttcggccag    300

ggcaccaagg tggagatcaa gcgg                                           324
```

<210> SEQ ID NO 106
<211> LENGTH: 108
<212> TYPE: PRT
<213> ORGANISM: Artificial Sequence
<220> FEATURE:
<223> OTHER INFORMATION: Synthetic

<400> SEQUENCE: 106

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Phe Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Arg Tyr Pro Trp
                85                  90                  95

Thr Phe Gly Gln Gly Thr Lys Val Glu Ile Lys Arg
            100                 105
```

<210> SEQ ID NO 107
<211> LENGTH: 357
<212> TYPE: DNA
<213> ORGANISM: Artificial Sequence
<220> FEATURE:
<223> OTHER INFORMATION: Synthetic

<400> SEQUENCE: 107

```
caggtgcagc tggtgcagtc tggggctgag gtgaagaagc ctggggcctc agtgaaggtc     60

tcctgcaagg tttccggatt caccctcact gaattatcca ttcactgggt gcgacaggct    120

cctggaaaag ggcttgagtg gatgggaggt tttgatcctg aagatggtga aacaatctac    180

gcacagaagt tccagggcag agtcaccatg accgaggaca catctacaga cacagcctac    240

atggagctga ccagcctgag atcggaagac acggccgtgt attactgttc aacgattttt    300

ggagtggtta ccaactttga caactggggc cagggaaccc tggtcaccgt ctcctca       357
```

<210> SEQ ID NO 108
<211> LENGTH: 119
<212> TYPE: PRT
<213> ORGANISM: Artificial Sequence
<220> FEATURE:
<223> OTHER INFORMATION: Synthetic

<400> SEQUENCE: 108

```
Gln Val Gln Leu Val Gln Ser Gly Ala Glu Val Lys Lys Pro Gly Ala
 1               5                  10                  15

Ser Val Lys Val Ser Cys Lys Val Ser Gly Phe Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Thr Ser Leu Arg Ser Glu Asp Thr Ala Val Tyr Tyr Cys
                85                  90                  95

Ser Thr Ile Phe Gly Val Val Thr Asn Phe Asp Asn Trp Gly Gln Gly
            100                 105                 110

Thr Leu Val Thr Val Ser Ser
```

115

<210> SEQ ID NO 109
<211> LENGTH: 324
<212> TYPE: DNA
<213> ORGANISM: Artificial Sequence
<220> FEATURE:
<223> OTHER INFORMATION: Synthetic

<400> SEQUENCE: 109
gacatccaga tgacccagtc tccatcctcc ctgtctgcat ctgcaggaga cagagtcacc 60
atcacttgcc gggcaagtca ggccattaga aatgatttag gctggtatca gcagaaacca 120
gggaaagccc ctaagcgcct gatctatgct gcattcaatt tgcaaagtgg ggtcccatca 180
agattcagcg gcagtggatc tgggacagaa ttcactctca caatcagtag cctgcagcct 240
gaagatcttg caagttatta ctgtcaacag tataatagat acccgtggac gttcggccaa 300
gggaccaagg tggaaatcaa acga 324

<210> SEQ ID NO 110
<211> LENGTH: 108
<212> TYPE: PRT
<213> ORGANISM: Artificial Sequence
<220> FEATURE:
<223> OTHER INFORMATION: Synthetic

<400> SEQUENCE: 110

Asp Ile Gln Met Thr Gln Ser Pro Ser Ser Leu Ser Ala Ser Ala Gly
1 5 10 15

Asp Arg Val Thr Ile Thr Cys Arg Ala Ser Gln Ala Ile Arg Asn Asp
20 25 30

Leu Gly Trp Tyr Gln Gln Lys Pro Gly Lys Ala Pro Lys Arg Leu Ile
35 40 45

Tyr Ala Ala Phe Asn Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Leu Ala Ser Tyr Tyr Cys Gln Gln Tyr Asn Arg Tyr Pro Trp
85 90 95

Thr Phe Gly Gln Gly Thr Lys Val Glu Ile Lys Arg
100 105

<210> SEQ ID NO 111
<211> LENGTH: 357
<212> TYPE: DNA
<213> ORGANISM: Artificial Sequence
<220> FEATURE:
<223> OTHER INFORMATION: Synthetic

<400> SEQUENCE: 111
caggtgcagc tggtgcagtc tggggctgag gtgaagaagc ctggggcctc agtgaaggtc 60
tcctgcaagg tttccggatt caccctcact gaattatcca ttcactgggt gcgacaggct 120
cctggaaaag ggcttgagtg gatgggaggt tttgatcctg aagatggtga aacaatctac 180
gcacagaagt tccagggcag agtcaccatg accgaggaca catctacaga cacagcctac 240
atggagctga ccagcctgag atcggaagac acggccgtgt attactgttc aacgattttt 300
ggagtggtta ccaactttga caactggggc cagggaaccc tggtcaccgt ctcctca 357

<210> SEQ ID NO 112
<211> LENGTH: 119

<212> TYPE: PRT
<213> ORGANISM: Artificial Sequence
<220> FEATURE:
<223> OTHER INFORMATION: Synthetic

<400> SEQUENCE: 112

```
Gln Val Gln Leu Val Gln Ser Gly Ala Glu Val Lys Lys Pro Gly Ala
 1               5                  10                  15

Ser Val Lys Val Ser Cys Lys Val Ser Gly Phe Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Thr Ser Leu Arg Ser Glu Asp Thr Ala Val Tyr Tyr Cys
                85                  90                  95

Ser Thr Ile Phe Gly Val Val Thr Asn Phe Asp Asn Trp Gly Gln Gly
            100                 105                 110

Thr Leu Val Thr Val Ser Ser
        115
```

<210> SEQ ID NO 113
<211> LENGTH: 324
<212> TYPE: DNA
<213> ORGANISM: Artificial Sequence
<220> FEATURE:
<223> OTHER INFORMATION: Synthetic

<400> SEQUENCE: 113

```
gacatccaga tgacccagtc tccatcctcc ctgtctgcat ctgcaggaga cagagtcacc      60

atcacttgcc gggcaagtca ggccattaga aatgatttag gctggtatca gcagaaacca     120

gggaaagccc ctaagcgcct gatctatgct gcattctcct tgcaaagtgg ggtcccatca     180

agattcagcg gcagtggatc tgggacagaa ttcactctca caatcagtag cctgcagcct     240

gaagatcttg caagttatta ctgtcaacag tataatagat acccgtggac gttcggccaa     300

gggaccaagg tggaaatcaa acga                                            324
```

<210> SEQ ID NO 114
<211> LENGTH: 108
<212> TYPE: PRT
<213> ORGANISM: Artificial Sequence
<220> FEATURE:
<223> OTHER INFORMATION: Synthetic

<400> SEQUENCE: 114

```
Asp Ile Gln Met Thr Gln Ser Pro Ser Ser Leu Ser Ala Ser Ala Gly
 1               5                  10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Phe Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Leu Ala Ser Tyr Tyr Cys Gln Gln Tyr Asn Arg Tyr Pro Trp
                85                  90                  95
```

```
Thr Phe Gly Gln Gly Thr Lys Val Glu Ile Lys Arg
            100                 105

<210> SEQ ID NO 115
<211> LENGTH: 357
<212> TYPE: DNA
<213> ORGANISM: Artificial Sequence
<220> FEATURE:
<223> OTHER INFORMATION: Synthetic

<400> SEQUENCE: 115

gaagtgcagc tggtgcagtc tggggctgag gtgaagaagc ctggggcctc agtgaaggtc      60

tcctgcaagg tttccggata caccctcact gaattatcca tacactgggt gcgacaggct     120

cctggaaaag ggcttgaatg gatgggaggt tttgatcctg aacatggtac aacaatctac     180

gcacagaagt tccagggcag agtcaccatg accgaggaca catctacaga cacagcctac     240

atggagctga gcagcctgag atctgaggac acggccgtgt attactgtgt aatgattttt     300

ggcgtggtta ccaattttga caactggggc cagggaacca cggtcaccgt ctcctca        357

<210> SEQ ID NO 116
<211> LENGTH: 119
<212> TYPE: PRT
<213> ORGANISM: Artificial Sequence
<220> FEATURE:
<223> OTHER INFORMATION: Synthetic

<400> SEQUENCE: 116

Glu Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu His Gly Thr Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Met Ile Phe Gly Val Val Thr Asn Phe Asp Asn Trp Gly Gln Gly
            100                 105                 110

Thr Thr Val Thr Val Ser Ser
        115

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117

ggatacaccc tcactgaatt atcc                                             24

<210> SEQ ID NO 118
<211> LENGTH: 8
<212> TYPE: PRT
<213> ORGANISM: Artificial Sequence
<220> FEATURE:
<223> OTHER INFORMATION: Synthetic
```

<400> SEQUENCE: 118

Gly Tyr Thr Leu Thr Glu Leu Ser
 1               5

<210> SEQ ID NO 119
<211> LENGTH: 24
<212> TYPE: DNA
<213> ORGANISM: Artificial Sequence
<220> FEATURE:
<223> OTHER INFORMATION: Synthetic

<400> SEQUENCE: 119
tttgatcctg aacatggtac aaca 24

<210> SEQ ID NO 120
<211> LENGTH: 8
<212> TYPE: PRT
<213> ORGANISM: Artificial Sequence
<220> FEATURE:
<223> OTHER INFORMATION: Synthetic

<400> SEQUENCE: 120

Phe Asp Pro Glu His Gly Thr Thr
 1               5

<210> SEQ ID NO 121
<211> LENGTH: 36
<212> TYPE: DNA
<213> ORGANISM: Artificial Sequence
<220> FEATURE:
<223> OTHER INFORMATION: Synthetic

<400> SEQUENCE: 121
gtaatgattt ttggcgtggt taccaatttt gacaac 36

<210> SEQ ID NO 122
<211> LENGTH: 12
<212> TYPE: PRT
<213> ORGANISM: Artificial Sequence
<220> FEATURE:
<223> OTHER INFORMATION: Synthetic

<400> SEQUENCE: 122

Val Met Ile Phe Gly Val Val Thr Asn Phe Asp Asn
 1               5                   10

<210> SEQ ID NO 123
<211> LENGTH: 321
<212> TYPE: DNA
<213> ORGANISM: Artificial Sequence
<220> FEATURE:
<223> OTHER INFORMATION: Synthetic

<400> SEQUENCE: 123
gacatcgtga tgacccagtc tccatcctcc ctgtctgcat ccgtgagaga cagagtcacc 60
atcacttgcc gggcaagtca gggcattaga aatgatttag gctggtatca gcagaaacca 120
gggaaagccc ctaagcgcct gatctatgct gcatccagtt tgcaaagtgg ggtcccatca 180
aggttcagcg gcagtggatc tgggacagaa ttcactctca cactcagcag cctgcagcct 240
gaagattttg caacttatta ttgttcacag tataataatt acccgtggac gttcggccaa 300
gggaccaagg tggagatcaa a 321

<210> SEQ ID NO 124
<211> LENGTH: 107

```
<212> TYPE: PRT
<213> ORGANISM: Artificial Sequence
<220> FEATURE:
<223> OTHER INFORMATION: Synthetic

<400> SEQUENCE: 124

Asp Ile Val Met Thr Gln Ser Pro Ser Ser Leu Ser Ala Ser Val Arg
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Leu Ser Ser Leu Gln Pro
65                  70                  75                  80

Glu Asp Phe Ala Thr Tyr Tyr Cys Ser Gln Tyr Asn Asn Tyr Pro Trp
                85                  90                  95

Thr Phe Gly Gln Gly Thr Lys Val Glu Ile Lys
            100                 105


<210> SEQ ID NO 125
<211> LENGTH: 18
<212> TYPE: DNA
<213> ORGANISM: Artificial Sequence
<220> FEATURE:
<223> OTHER INFORMATION: Synthetic

<400> SEQUENCE: 125

cagggcatta gaaatgat                                                    18


<210> SEQ ID NO 126
<211> LENGTH: 6
<212> TYPE: PRT
<213> ORGANISM: Artificial Sequence
<220> FEATURE:
<223> OTHER INFORMATION: Synthetic

<400> SEQUENCE: 126

Gln Gly Ile Arg Asn Asp
 1               5


<210> SEQ ID NO 127
<211> LENGTH: 9
<212> TYPE: DNA
<213> ORGANISM: Artificial Sequence
<220> FEATURE:
<223> OTHER INFORMATION: Synthetic

<400> SEQUENCE: 127

gctgcatcc                                                               9


<210> SEQ ID NO 128
<211> LENGTH: 3
<212> TYPE: PRT
<213> ORGANISM: Artificial Sequence
<220> FEATURE:
<223> OTHER INFORMATION: Synthetic

<400> SEQUENCE: 128

Ala Ala Ser
 1


<210> SEQ ID NO 129
```

<211> LENGTH: 27
<212> TYPE: DNA
<213> ORGANISM: Artificial Sequence
<220> FEATURE:
<223> OTHER INFORMATION: Synthetic

<400> SEQUENCE: 129
tcacagtata ataattaccc gtggacg 27

<210> SEQ ID NO 130
<211> LENGTH: 9
<212> TYPE: PRT
<213> ORGANISM: Artificial Sequence
<220> FEATURE:
<223> OTHER INFORMATION: Synthetic

<400> SEQUENCE: 130

Ser Gln Tyr Asn Asn Tyr Pro Trp Thr
1 5

<210> SEQ ID NO 131
<211> LENGTH: 357
<212> TYPE: DNA
<213> ORGANISM: Artificial Sequence
<220> FEATURE:
<223> OTHER INFORMATION: Synthetic

<400> SEQUENCE: 131
caggtgcagc tggtgcagtc cggcgccgag gtgaagaagc ccggcgcctc cgtgaaggtg 60
tcctgcaagg tgtccggcta caccctgacc gagctgtcca tgcactgggt gcggcaggcc 120
cccggcaagg gcctggagtg gatgggcggc ttcgaccccg agcacggcac caccatctac 180
gcccagaagt tccagggccg ggtgaccatg accgaggaca cctccaccga caccgcctac 240
atggagctgt cctccctgcg gtccgaggac accgccgtgt actactgcgt gatgatcttc 300
ggcgtggtga ccaacttcga caactggggc cagggcaccc tggtgaccgt gtcctcc 357

<210> SEQ ID NO 132
<211> LENGTH: 119
<212> TYPE: PRT
<213> ORGANISM: Artificial Sequence
<220> FEATURE:
<223> OTHER INFORMATION: Synthetic

<400> SEQUENCE: 132

Gln Val Gln Leu Val Gln Ser Gly Ala Glu Val Lys Lys Pro Gly Ala
1 5 10 15

Ser Val Lys Val Ser Cys Lys Val Ser Gly Tyr Thr Leu Thr Glu Leu
20 25 30

Ser Met His Trp Val Arg Gln Ala Pro Gly Lys Gly Leu Glu Trp Met
35 40 45

Gly Gly Phe Asp Pro Glu His Gly Thr Thr Ile Tyr Ala Gln Lys Phe
50 55 60

Gln Gly Arg Val Thr Met Thr Glu Asp Thr Ser Thr Asp Thr Ala Tyr
65 70 75 80

Met Glu Leu Ser Ser Leu Arg Ser Glu Asp Thr Ala Val Tyr Tyr Cys
85 90 95

Val Met Ile Phe Gly Val Val Thr Asn Phe Asp Asn Trp Gly Gln Gly
100 105 110

Thr Leu Val Thr Val Ser Ser
115

<210> SEQ ID NO 133
<211> LENGTH: 321
<212> TYPE: DNA
<213> ORGANISM: Artificial Sequence
<220> FEATURE:
<223> OTHER INFORMATION: Synthetic

<400> SEQUENCE: 133

```
gacatccaga tgacccagtc cccctcctcc ctgtccgcct ccgtgggcga ccgggtgacc      60

atcacctgcc gggcctccca gggcatccgg aacgacctgg gctggtacca gcagaagccc     120

ggcaaggccc ccaagcggct gatctacgcc gcctcctccc tgcagtccgg cgtgccctcc     180

cggttctccg gctccggctc cggcaccgag ttcaccctga ccatctcctc cctgcagccc     240

gaggacttcg ccacctacta ctgctcccag tacaacaact acccctggac cttcggccag     300

ggcaccaagg tggagatcaa g                                               321
```

<210> SEQ ID NO 134
<211> LENGTH: 107
<212> TYPE: PRT
<213> ORGANISM: Artificial Sequence
<220> FEATURE:
<223> OTHER INFORMATION: Synthetic

<400> SEQUENCE: 134

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Ser Gln Tyr Asn Asn Tyr Pro Trp
                85                  90                  95

Thr Phe Gly Gln Gly Thr Lys Val Glu Ile Lys
            100                 105
```

<210> SEQ ID NO 135
<211> LENGTH: 357
<212> TYPE: DNA
<213> ORGANISM: Artificial Sequence
<220> FEATURE:
<223> OTHER INFORMATION: Synthetic

<400> SEQUENCE: 135

```
caggtgcagc tggtgcagtc tggggctgag gtgaagaagc ctggggcctc agtgaaggtc      60

tcctgcaagg tttccggata caccctcact gaattatcca tacactgggt gcgacaggct     120

cctggaaaag ggcttgaatg gatgggaggt tttgatcctg aacatggtac aacaatctac     180

gcacagaagt tccagggcag agtcaccatg accgaggaca catctacaga cacagcctac     240

atggagctga gcagcctgag atctgaggac acggccgtgt attactgtgt aatgattttt     300

ggcgtggtta ccaattttga caactggggc cagggtaccc tggtcaccgt ctcctca        357
```

<210> SEQ ID NO 136
<211> LENGTH: 119
<212> TYPE: PRT
<213> ORGANISM: Artificial Sequence
<220> FEATURE:

<223> OTHER INFORMATION: Synthetic

<400> SEQUENCE: 136

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu His Gly Thr Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Met Ile Phe Gly Val Val Thr Asn Phe Asp Asn Trp Gly Gln Gly
            100                 105                 110

Thr Leu Val Thr Val Ser Ser
        115
```

<210> SEQ ID NO 137
<211> LENGTH: 321
<212> TYPE: DNA
<213> ORGANISM: Artificial Sequence
<220> FEATURE:
<223> OTHER INFORMATION: Synthetic

<400> SEQUENCE: 137

```
gacatccaga tgacccagtc tccatcctcc ctgtctgcat ccgtgagaga cagagtcacc      60

atcacttgcc gggcaagtca gggcattaga aatgatttag gctggtatca gcagaaacca     120

gggaaagccc ctaagcgcct gatctatgct gcatccagtt tgcaaagtgg ggtcccatca     180

aggttcagcg gcagtggatc tgggacagaa ttcactctca cactcagcag cctgcagcct     240

gaagattttg caacttatta ttgttcacag tataataatt acccgtggac gttcggccaa     300

gggaccaagg tggagatcaa a                                               321
```

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

```
Asp Ile Gln Met Thr Gln Ser Pro Ser Ser Leu Ser Ala Ser Val Arg
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Leu Ser Ser Leu Gln Pro
65                  70                  75                  80

Glu Asp Phe Ala Thr Tyr Tyr Cys Ser Gln Tyr Asn Asn Tyr Pro Trp
                85                  90                  95

Thr Phe Gly Gln Gly Thr Lys Val Glu Ile Lys
            100                 105
```

<210> SEQ ID NO 139
<211> LENGTH: 357
<212> TYPE: DNA
<213> ORGANISM: Artificial Sequence
<220> FEATURE:
<223> OTHER INFORMATION: Synthetic

<400> SEQUENCE: 139
gaggtgcagc tggtgcagtc tggggctgag gtgaagaagc ctggggcctc agtgaaggtc 60
tcctgcaagg tttccggatt caccctcact gaattatcca ttcactgggt gcgacaggct 120
cctggaaaag ggcttgagtg gatgggaggt tttgatcctg aagatggtga aacaatctac 180
gcacagaagt tccagggcag agtcaccatg accgaggaca catctacaga cacagcctgc 240
atggaactga gcagtctgag atctgaagac acggccgtgt attactgttc aacgattttt 300
ggagtggtta ccaactttga caactggggc cagggaaccc tggtcaccgt ctcctca 357

<210> SEQ ID NO 140
<211> LENGTH: 119
<212> TYPE: PRT
<213> ORGANISM: Artificial Sequence
<220> FEATURE:
<223> OTHER INFORMATION: Synthetic

<400> SEQUENCE: 140

Glu Val Gln Leu Val Gln Ser Gly Ala Glu Val Lys Lys Pro Gly Ala
1 5 10 15

Ser Val Lys Val Ser Cys Lys Val Ser Gly Phe Thr Leu Thr Glu Leu
20 25 30

Ser Ile His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Phe
50 55 60

Gln Gly Arg Val Thr Met Thr Glu Asp Thr Ser Thr Asp Thr Ala Cys
65 70 75 80

Met Glu Leu Ser Ser Leu Arg Ser Glu Asp Thr Ala Val Tyr Tyr Cys
85 90 95

Ser Thr Ile Phe Gly Val Val Thr Asn Phe Asp Asn Trp Gly Gln Gly
100 105 110

Thr Leu Val Thr Val Ser Ser
115

<210> SEQ ID NO 141
<211> LENGTH: 24
<212> TYPE: DNA
<213> ORGANISM: Artificial Sequence
<220> FEATURE:
<223> OTHER INFORMATION: Synthetic

<400> SEQUENCE: 141
ggattcaccc tcactgaatt atcc 24

<210> SEQ ID NO 142
<211> LENGTH: 8
<212> TYPE: PRT
<213> ORGANISM: Artificial Sequence
<220> FEATURE:
<223> OTHER INFORMATION: Synthetic

<400> SEQUENCE: 142

Gly Phe Thr Leu Thr Glu Leu Ser 1 5

<210> SEQ ID NO 143
<211> LENGTH: 24
<212> TYPE: DNA
<213> ORGANISM: Artificial Sequence
<220> FEATURE:
<223> OTHER INFORMATION: Synthetic

<400> SEQUENCE: 143
tttgatcctg aagatggtga aaca 24

<210> SEQ ID NO 144
<211> LENGTH: 8
<212> TYPE: PRT
<213> ORGANISM: Artificial Sequence
<220> FEATURE:
<223> OTHER INFORMATION: Synthetic

<400> SEQUENCE: 144

Phe Asp Pro Glu Asp Gly Glu Thr
1 5

<210> SEQ ID NO 145
<211> LENGTH: 36
<212> TYPE: DNA
<213> ORGANISM: Artificial Sequence
<220> FEATURE:
<223> OTHER INFORMATION: Synthetic

<400> SEQUENCE: 145
tcaacgattt ttggagtggt taccaacttt gacaac 36

<210> SEQ ID NO 146
<211> LENGTH: 12
<212> TYPE: PRT
<213> ORGANISM: Artificial Sequence
<220> FEATURE:
<223> OTHER INFORMATION: Synthetic

<400> SEQUENCE: 146

Ser Thr Ile Phe Gly Val Val Thr Asn Phe Asp Asn
1 5 10

<210> SEQ ID NO 147
<211> LENGTH: 321
<212> TYPE: DNA
<213> ORGANISM: Artificial Sequence
<220> FEATURE:
<223> OTHER INFORMATION: Synthetic

<400> SEQUENCE: 147
gatgttgtga tgactcagtc tccatcctcc ctgtctgcat ctgcaggaga cagagtcacc 60
atcacttgcc gggcaagtca ggccattaga aatgatttag gctggtatca gcagaaacca 120
gggaaagccc ctaaacgcct gatctatgct gcattcaatt tgcaaagtgg ggtcccatca 180
agattcagcg gcagtggatc tgggacagaa ttcactctca caatcagtag cctgcagcct 240
gaagatcttg caagttatta ctgtcaacag tataatagat acccgtggac gttcggccaa 300
gggaccaagc tggagatcaa a 321

<210> SEQ ID NO 148
<211> LENGTH: 107
<212> TYPE: PRT
<213> ORGANISM: Artificial Sequence
<220> FEATURE:

<223> OTHER INFORMATION: Synthetic

<400> SEQUENCE: 148

Asp Val Val Met Thr Gln Ser Pro Ser Ser Leu Ser Ala Ser Ala Gly
1 5 10 15

Asp Arg Val Thr Ile Thr Cys Arg Ala Ser Gln Ala Ile Arg Asn Asp
20 25 30

Leu Gly Trp Tyr Gln Gln Lys Pro Gly Lys Ala Pro Lys Arg Leu Ile
35 40 45

Tyr Ala Ala Phe Asn Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Leu Ala Ser Tyr Tyr Cys Gln Gln Tyr Asn Arg Tyr Pro Trp
85 90 95

Thr Phe Gly Gln Gly Thr Lys Leu Glu Ile Lys
100 105

<210> SEQ ID NO 149
<211> LENGTH: 18
<212> TYPE: DNA
<213> ORGANISM: Artificial Sequence
<220> FEATURE:
<223> OTHER INFORMATION: Synthetic

<400> SEQUENCE: 149
caggccatta gaaatgat 18

<210> SEQ ID NO 150
<211> LENGTH: 6
<212> TYPE: PRT
<213> ORGANISM: Artificial Sequence
<220> FEATURE:
<223> OTHER INFORMATION: Synthetic

<400> SEQUENCE: 150

Gln Ala Ile Arg Asn Asp
1 5

<210> SEQ ID NO 151
<211> LENGTH: 9
<212> TYPE: DNA
<213> ORGANISM: Artificial Sequence
<220> FEATURE:
<223> OTHER INFORMATION: Synthetic

<400> SEQUENCE: 151 gctgcattc 9

<210> SEQ ID NO 152
<211> LENGTH: 3
<212> TYPE: PRT
<213> ORGANISM: Artificial Sequence
<220> FEATURE:
<223> OTHER INFORMATION: Synthetic

<400> SEQUENCE: 152

Ala Ala Phe
1

<210> SEQ ID NO 153
<211> LENGTH: 27
<212> TYPE: DNA
<213> ORGANISM: Artificial Sequence
<220> FEATURE:
<223> OTHER INFORMATION: Synthetic

<400> SEQUENCE: 153
caacagtata atagataccc gtggacg 27

<210> SEQ ID NO 154
<211> LENGTH: 9
<212> TYPE: PRT
<213> ORGANISM: Artificial Sequence
<220> FEATURE:
<223> OTHER INFORMATION: Synthetic

<400> SEQUENCE: 154

```
Gln Gln Tyr Asn Arg Tyr Pro Trp Thr
 1               5
```

<210> SEQ ID NO 155
<211> LENGTH: 357
<212> TYPE: DNA
<213> ORGANISM: Artificial Sequence
<220> FEATURE:
<223> OTHER INFORMATION: Synthetic

<400> SEQUENCE: 155

```
caggtgcagc tggtgcagtc tggggctgag gtgaagaagc ctggggcctc agtgaaggtc     60

tcctgcaagg tttccggatt caccctcact gaattatcca ttcactgggt gcgacaggct    120

cctggaaaag ggcttgagtg gatgggaggt tttgatcctg aagatggtga aacaatctac    180

gcacagaagt tccagggcag agtcaccatg accgaggaca catctacaga cacagcctgc    240

atggaactga gcagtctgag atctgaagac acggccgtgt attactgttc aacgattttt    300

ggagtggtta ccaactttga caactggggc cagggaaccc tggtcaccgt ctcctca       357
```

<210> SEQ ID NO 156
<211> LENGTH: 119
<212> TYPE: PRT
<213> ORGANISM: Artificial Sequence
<220> FEATURE:
<223> OTHER INFORMATION: Synthetic

<400> SEQUENCE: 156

```
Gln Val Gln Leu Val Gln Ser Gly Ala Glu Val Lys Lys Pro Gly Ala
 1               5                  10                  15

Ser Val Lys Val Ser Cys Lys Val Ser Gly Phe Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Cys
65                  70                  75                  80

Met Glu Leu Ser Ser Leu Arg Ser Glu Asp Thr Ala Val Tyr Tyr Cys
                85                  90                  95

Ser Thr Ile Phe Gly Val Val Thr Asn Phe Asp Asn Trp Gly Gln Gly
            100                 105                 110

Thr Leu Val Thr Val Ser Ser
        115
```

<210> SEQ ID NO 157
<211> LENGTH: 321
<212> TYPE: DNA

<213> ORGANISM: Artificial Sequence
<220> FEATURE:
<223> OTHER INFORMATION: Synthetic

<400> SEQUENCE: 157
gacatccaga tgacccagtc tccatcctcc ctgtctgcat ctgcaggaga cagagtcacc 60
atcacttgcc gggcaagtca ggccattaga aatgatttag gctggtatca gcagaaacca 120
gggaaagccc ctaaacgcct gatctatgct gcattcaatt tgcaaagtgg ggtcccatca 180
agattcagcg gcagtggatc tgggacagaa ttcactctca caatcagtag cctgcagcct 240
gaagatcttg caagttatta ctgtcaacag tataatagat acccgtggac gttcggccaa 300
gggaccaagg tggagatcaa a 321

<210> SEQ ID NO 158
<211> LENGTH: 107
<212> TYPE: PRT
<213> ORGANISM: Artificial Sequence
<220> FEATURE:
<223> OTHER INFORMATION: Synthetic

<400> SEQUENCE: 158

Asp Ile Gln Met Thr Gln Ser Pro Ser Ser Leu Ser Ala Ser Ala Gly
1 5 10 15

Asp Arg Val Thr Ile Thr Cys Arg Ala Ser Gln Ala Ile Arg Asn Asp
20 25 30

Leu Gly Trp Tyr Gln Gln Lys Pro Gly Lys Ala Pro Lys Arg Leu Ile
35 40 45

Tyr Ala Ala Phe Asn Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Leu Ala Ser Tyr Tyr Cys Gln Gln Tyr Asn Arg Tyr Pro Trp
85 90 95

Thr Phe Gly Gln Gly Thr Lys Val Glu Ile Lys
100 105

<210> SEQ ID NO 159
<211> LENGTH: 357
<212> TYPE: DNA
<213> ORGANISM: Artificial Sequence
<220> FEATURE:
<223> OTHER INFORMATION: Synthetic

<400> SEQUENCE: 159
gaggtgcagc tggtgcagtc tggggctgag gtgaagaagc ctggggcctc agtgaaggtc 60
tcctgcaagg tttccggatt caccctcaat gaattatcca ttcactgggt gcgacaggct 120
cctggaaaag ggcttgagtg gatgggaggt tttgatcctg aagatggtga agtaatttat 180
gcacagaagt tccagggcag agtcaccatg accgaggaca catctacaga cacagcctac 240
atggaactga ggagcctgag atctgaggac acggccgtgt tttattgtgt aatgattttt 300
ggagtggtta ccaactttga caattggggc cagggaacca cggtcaccgt ctcctca 357

<210> SEQ ID NO 160
<211> LENGTH: 119
<212> TYPE: PRT
<213> ORGANISM: Artificial Sequence
<220> FEATURE:
<223> OTHER INFORMATION: Synthetic

<400> SEQUENCE: 160

```
Glu Val Gln Leu Val Gln Ser Gly Ala Glu Val Lys Lys Pro Gly Ala
 1               5                  10                  15

Ser Val Lys Val Ser Cys Lys Val Ser Gly Phe Thr Leu Asn Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Val Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Arg Ser Leu Arg Ser Glu Asp Thr Ala Val Phe Tyr Cys
                85                  90                  95

Val Met Ile Phe Gly Val Val Thr Asn Phe Asp Asn Trp Gly Gln Gly
            100                 105                 110

Thr Thr Val Thr Val Ser Ser
        115
```

<210> SEQ ID NO 161
<211> LENGTH: 24
<212> TYPE: DNA
<213> ORGANISM: Artificial Sequence
<220> FEATURE:
<223> OTHER INFORMATION: Synthetic

<400> SEQUENCE: 161

```
ggattcaccc tcaatgaatt atcc                                            24
```

<210> SEQ ID NO 162
<211> LENGTH: 8
<212> TYPE: PRT
<213> ORGANISM: Artificial Sequence
<220> FEATURE:
<223> OTHER INFORMATION: Synthetic

<400> SEQUENCE: 162

```
Gly Phe Thr Leu Asn Glu Leu Ser
 1               5
```

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163

```
tttgatcctg aagatggtga agta                                            24
```

<210> SEQ ID NO 164
<211> LENGTH: 9
<212> TYPE: PRT
<213> ORGANISM: Artificial Sequence
<220> FEATURE:
<223> OTHER INFORMATION: Synthetic

<400> SEQUENCE: 164

```
Gly Phe Asp Pro Glu Asp Gly Glu Val
 1               5
```

<210> SEQ ID NO 165
<211> LENGTH: 36
<212> TYPE: DNA
<213> ORGANISM: Artificial Sequence
<220> FEATURE:
<223> OTHER INFORMATION: Synthetic

<400> SEQUENCE: 165
gtaatgattt ttggagtggt taccaacttt gacaat 36

<210> SEQ ID NO 166
<211> LENGTH: 12
<212> TYPE: PRT
<213> ORGANISM: Artificial Sequence
<220> FEATURE:
<223> OTHER INFORMATION: Synthetic

<400> SEQUENCE: 166

Val Met Ile Phe Gly Val Val Thr Asn Phe Asp Asn
1 5 10

<210> SEQ ID NO 167
<211> LENGTH: 321
<212> TYPE: DNA
<213> ORGANISM: Artificial Sequence
<220> FEATURE:
<223> OTHER INFORMATION: Synthetic

<400> SEQUENCE: 167
gacatccaga tgacccagtc tccatcctcc ctgtctgcat ctgtgagaga cagagtcacc 60
atcacttgcc gggcaagtca gggcattaga aatgatttag gctggtatca gcagaaacca 120
gggaaagccc ctaagcgcct gatctatggt gcattcagtt tgcaaagtgg ggtcccatca 180
aggttcagcg gcagtggatc tgggacagaa ttcactctca caatcagcag cctgcagcct 240
gaagattttg caacttatta ctgtctacag tataatactt atccgtggac gttcggccaa 300
gggaccaagg tggagatcaa a 321

<210> SEQ ID NO 168
<211> LENGTH: 107
<212> TYPE: PRT
<213> ORGANISM: Artificial Sequence
<220> FEATURE:
<223> OTHER INFORMATION: Synthetic

<400> SEQUENCE: 168

Asp Ile Gln Met Thr Gln Ser Pro Ser Ser Leu Ser Ala Ser Val Arg
1 5 10 15

Asp Arg Val Thr Ile Thr Cys Arg Ala Ser Gln Gly Ile Arg Asn Asp
20 25 30

Leu Gly Trp Tyr Gln Gln Lys Pro Gly Lys Ala Pro Lys Arg Leu Ile
35 40 45

Tyr Gly Ala Phe Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Leu Gln Tyr Asn Thr Tyr Pro Trp
85 90 95

Thr Phe Gly Gln Gly Thr Lys Val Glu Ile Lys
100 105

<210> SEQ ID NO 169
<211> LENGTH: 18
<212> TYPE: DNA
<213> ORGANISM: Artificial Sequence
<220> FEATURE:
<223> OTHER INFORMATION: Synthetic

<400> SEQUENCE: 169
cagggcatta gaaatgat 18

<210> SEQ ID NO 170
<211> LENGTH: 6
<212> TYPE: PRT
<213> ORGANISM: Artificial Sequence
<220> FEATURE:
<223> OTHER INFORMATION: Synthetic

<400> SEQUENCE: 170

Gln Gly Ile Arg Asn Asp
1 5

<210> SEQ ID NO 171
<211> LENGTH: 9
<212> TYPE: DNA
<213> ORGANISM: Artificial Sequence
<220> FEATURE:
<223> OTHER INFORMATION: Synthetic

<400> SEQUENCE: 171 ggtgcattc 9

<210> SEQ ID NO 172
<211> LENGTH: 3
<212> TYPE: PRT
<213> ORGANISM: Artificial Sequence
<220> FEATURE:
<223> OTHER INFORMATION: Synthetic

<400> SEQUENCE: 172

Gly Ala Phe
1

<210> SEQ ID NO 173
<211> LENGTH: 27
<212> TYPE: DNA
<213> ORGANISM: Artificial Sequence
<220> FEATURE:
<223> OTHER INFORMATION: Synthetic

<400> SEQUENCE: 173
ctacagtata atacttatcc gtggacg 27

<210> SEQ ID NO 174
<211> LENGTH: 9
<212> TYPE: PRT
<213> ORGANISM: Artificial Sequence
<220> FEATURE:
<223> OTHER INFORMATION: Synthetic

<400> SEQUENCE: 174

Leu Gln Tyr Asn Thr Tyr Pro Trp Thr
1 5

<210> SEQ ID NO 175
<211> LENGTH: 357
<212> TYPE: DNA
<213> ORGANISM: Artificial Sequence
<220> FEATURE:
<223> OTHER INFORMATION: Synthetic

<400> SEQUENCE: 175
caggtgcagc tggtgcagtc cggcgccgag gtgaagaagc ccggcgcctc cgtgaaggtg 60

```
tcctgcaagg tgtccggctt caccctgaac gagctgtcca tgcactgggt gcggcaggcc    120

cccggcaagg gcctggagtg gatgggcggc ttcgaccccg aggacggcga ggtgatctac    180

gcccagaagt tccagggccg ggtgaccatg accgaggaca cctccaccga caccgcctac    240

atggagctgt cctccctgcg gtccgaggac accgccgtgt actactgcgt gatgatcttc    300

ggcgtggtga ccaacttcga caactggggc cagggcaccc tggtgaccgt gtcctcc       357
```

<210> SEQ ID NO 176
<211> LENGTH: 119
<212> TYPE: PRT
<213> ORGANISM: Artificial Sequence
<220> FEATURE:
<223> OTHER INFORMATION: Synthetic

<400> SEQUENCE: 176

```
Gln Val Gln Leu Val Gln Ser Gly Ala Glu Val Lys Lys Pro Gly Ala
 1               5                  10                  15

Ser Val Lys Val Ser Cys Lys Val Ser Gly Phe Thr Leu Asn Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Val Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Met Ile Phe Gly Val Val Thr Asn Phe Asp Asn Trp Gly Gln Gly
            100                 105                 110

Thr Leu Val Thr Val Ser Ser
        115
```

<210> SEQ ID NO 177
<211> LENGTH: 321
<212> TYPE: DNA
<213> ORGANISM: Artificial Sequence
<220> FEATURE:
<223> OTHER INFORMATION: Synthetic

<400> SEQUENCE: 177

```
gacatccaga tgacccagtc cccctcctcc ctgtccgcct ccgtgggcga ccgggtgacc     60

atcacctgcc gggcctccca gggcatccgg aacgacctgg gctggtacca gcagaagccc    120

ggcaaggccc ccaagcggct gatctacggc gccttctccc tgcagtccgg cgtgccctcc    180

cggttctccg gctccggctc cggcaccgag ttcaccctga ccatctcctc cctgcagccc    240

gaggacttcg ccacctacta ctgcctgcag tacaacacct acccctggac cttcggccag    300

ggcaccaagg tggagatcaa g                                              321
```

<210> SEQ ID NO 178
<211> LENGTH: 107
<212> TYPE: PRT
<213> ORGANISM: Artificial Sequence
<220> FEATURE:
<223> OTHER INFORMATION: Synthetic

<400> SEQUENCE: 178

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
```

```
            20                  25                  30

Leu Gly Trp Tyr Gln Gln Lys Pro Gly Lys Ala Pro Lys Arg Leu Ile
        35                  40                  45

Tyr Gly Ala Phe Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Thr Tyr Pro Trp
                85                  90                  95

Thr Phe Gly Gln Gly Thr Lys Val Glu Ile Lys
            100                 105


<210> SEQ ID NO 179
<211> LENGTH: 357
<212> TYPE: DNA
<213> ORGANISM: Artificial Sequence
<220> FEATURE:
<223> OTHER INFORMATION: Synthetic

<400> SEQUENCE: 179

caggtgcagc tggtgcagtc tggggctgag gtgaagaagc ctggggcctc agtgaaggtc      60

tcctgcaagg tttccggatt caccctcaat gaattatcca ttcactgggt gcgacaggct     120

cctggaaaag ggcttgagtg gatgggaggt tttgatcctg aagatggtga agtaatttat     180

gcacagaagt tccagggcag agtcaccatg accgaggaca catctacaga cacagcctac     240

atggaactga ggagcctgag atctgaggac acggccgtgt tttattgtgt aatgattttt     300

ggagtggtta ccaactttga caattggggc cagggaaccc tggtcaccgt ctcctca        357


<210> SEQ ID NO 180
<211> LENGTH: 119
<212> TYPE: PRT
<213> ORGANISM: Artificial Sequence
<220> FEATURE:
<223> OTHER INFORMATION: Synthetic

<400> SEQUENCE: 180

Gln Val Gln Leu Val Gln Ser Gly Ala Glu Val Lys Lys Pro Gly Ala
 1               5                  10                  15

Ser Val Lys Val Ser Cys Lys Val Ser Gly Phe Thr Leu Asn Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Val Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Arg Ser Leu Arg Ser Glu Asp Thr Ala Val Phe Tyr Cys
                85                  90                  95

Val Met Ile Phe Gly Val Val Thr Asn Phe Asp Asn Trp Gly Gln Gly
            100                 105                 110

Thr Leu Val Thr Val Ser Ser
        115


<210> SEQ ID NO 181
<211> LENGTH: 321
<212> TYPE: DNA
<213> ORGANISM: Artificial Sequence
<220> FEATURE:
<223> OTHER INFORMATION: Synthetic
```

<400> SEQUENCE: 181

```
gacatccaga tgacccagtc tccatcctcc ctgtctgcat ctgtgagaga cagagtcacc     60

atcacttgcc gggcaagtca gggcattaga aatgatttag gctggtatca gcagaaacca    120

gggaaagccc ctaagcgcct gatctatggt gcattcagtt tgcaaagtgg ggtcccatca    180

aggttcagcg gcagtggatc tgggacagaa ttcactctca caatcagcag cctgcagcct    240

gaagattttg caacttatta ctgtctacag tataatactt atccgtggac gttcggccaa    300

gggaccaagg tggagatcaa a                                              321
```

<210> SEQ ID NO 182
<211> LENGTH: 107
<212> TYPE: PRT
<213> ORGANISM: Artificial Sequence
<220> FEATURE:
<223> OTHER INFORMATION: Synthetic

<400> SEQUENCE: 182

```
Asp Ile Gln Met Thr Gln Ser Pro Ser Ser Leu Ser Ala Ser Val Arg
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Gly Ala Phe Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Thr Tyr Pro Trp
                85                  90                  95

Thr Phe Gly Gln Gly Thr Lys Val Glu Ile Lys
            100                 105
```

<210> SEQ ID NO 183
<211> LENGTH: 357
<212> TYPE: DNA
<213> ORGANISM: Artificial Sequence
<220> FEATURE:
<223> OTHER INFORMATION: Synthetic

<400> SEQUENCE: 183

```
gaggtgcagc tggtgcagtc tgggactgag gtgaagaagc ctggggcctc agtgaaggtc     60

tcctgcaagg tttccggata caccctcact gaattatcca tgtactgggt gcgacaggct    120

cctggaaaag ggcttgagtg gatgggaggt tttgatcctg aacatggtga aacaatctac    180

gcacagaagt tccagggcag agtcaccatg accgaggact catctacaga cacagcctac    240

atggagctga gcagcctgag atctgaggac acggccgtgt attactgtgc aatgattttt    300

ggagtggtta ccaactttga ctcctggggc ctgggaaccc tggtcactgt ctcctca       357
```

<210> SEQ ID NO 184
<211> LENGTH: 119
<212> TYPE: PRT
<213> ORGANISM: Artificial Sequence
<220> FEATURE:
<223> OTHER INFORMATION: Synthetic

<400> SEQUENCE: 184

```
Glu Val Gln Leu Val Gln Ser Gly Thr Glu Val Lys Lys Pro Gly Ala
 1               5                  10                  15
```

```
Ser Val Lys Val Ser Cys Lys Val Ser Gly Tyr Thr Leu Thr Glu Leu
            20                  25                  30

Ser Met Tyr Trp Val Arg Gln Ala Pro Gly Lys Gly Leu Glu Trp Met
        35                  40                  45

Gly Gly Phe Asp Pro Glu His Gly Glu Thr Ile Tyr Ala Gln Lys Phe
    50                  55                  60

Gln Gly Arg Val Thr Met Thr Glu Asp Ser Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Met Ile Phe Gly Val Val Thr Asn Phe Asp Ser Trp Gly Leu Gly
            100                 105                 110

Thr Leu Val Thr Val Ser Ser
        115


<210> SEQ ID NO 185
<211> LENGTH: 24
<212> TYPE: DNA
<213> ORGANISM: Artificial Sequence
<220> FEATURE:
<223> OTHER INFORMATION: Synthetic

<400> SEQUENCE: 185

ggatacaccc tcactgaatt atcc                                            24


<210> SEQ ID NO 186
<211> LENGTH: 8
<212> TYPE: PRT
<213> ORGANISM: Artificial Sequence
<220> FEATURE:
<223> OTHER INFORMATION: Synthetic

<400> SEQUENCE: 186

Gly Tyr Thr Leu Thr Glu Leu Ser
 1               5


<210> SEQ ID NO 187
<211> LENGTH: 24
<212> TYPE: DNA
<213> ORGANISM: Artificial Sequence
<220> FEATURE:
<223> OTHER INFORMATION: Synthetic

<400> SEQUENCE: 187

tttgatcctg aacatggtga aaca                                            24


<210> SEQ ID NO 188
<211> LENGTH: 8
<212> TYPE: PRT
<213> ORGANISM: Artificial Sequence
<220> FEATURE:
<223> OTHER INFORMATION: Synthetic

<400> SEQUENCE: 188

Phe Asp Pro Glu His Gly Glu Thr
 1               5


<210> SEQ ID NO 189
<211> LENGTH: 36
<212> TYPE: DNA
<213> ORGANISM: Artificial Sequence
<220> FEATURE:
<223> OTHER INFORMATION: Synthetic
```

<400> SEQUENCE: 189
gcaatgattt ttggagtggt taccaacttt gactcc 36

<210> SEQ ID NO 190
<211> LENGTH: 12
<212> TYPE: PRT
<213> ORGANISM: Artificial Sequence
<220> FEATURE:
<223> OTHER INFORMATION: Synthetic

<400> SEQUENCE: 190

```
Ala Met Ile Phe Gly Val Val Thr Asn Phe Asp Ser
 1               5                  10
```

<210> SEQ ID NO 191
<211> LENGTH: 321
<212> TYPE: DNA
<213> ORGANISM: Artificial Sequence
<220> FEATURE:
<223> OTHER INFORMATION: Synthetic

<400> SEQUENCE: 191

```
gaaattgtgt tgacacagtc tccatcctcc ctgtctgcat ctgtaggaga cagagtcacc     60

atcacttgcc gggcaagtca gggcattaga aatgatttag gctggtatca gcagaaacca    120

gggaaagccc ctaagcgcct gatctatgct gcatccagtt tgcaaagtgg ggtcccatca    180

aggttcagcg gcagtggatc tgggacagaa ttcactctca caatcagcag cctgcagcct    240

gaagattttg caacttatta ctgtctacag tataatagtt acccgtggac gttcggccaa    300

gggaccaagc tggagatcaa a                                              321
```

<210> SEQ ID NO 192
<211> LENGTH: 107
<212> TYPE: PRT
<213> ORGANISM: Artificial Sequence
<220> FEATURE:
<223> OTHER INFORMATION: Synthetic

<400> SEQUENCE: 192

```
Glu Ile Val Leu Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Tyr Pro Trp
                85                  90                  95

Thr Phe Gly Gln Gly Thr Lys Leu Glu Ile Lys
            100                 105
```

<210> SEQ ID NO 193
<211> LENGTH: 18
<212> TYPE: DNA
<213> ORGANISM: Artificial Sequence
<220> FEATURE:
<223> OTHER INFORMATION: Synthetic

<400> SEQUENCE: 193
cagggcatta gaaatgat 18

<210> SEQ ID NO 194
<211> LENGTH: 6
<212> TYPE: PRT
<213> ORGANISM: Artificial Sequence
<220> FEATURE:
<223> OTHER INFORMATION: Synthetic

<400> SEQUENCE: 194

Gln Gly Ile Arg Asn Asp
1 5

<210> SEQ ID NO 195
<211> LENGTH: 9
<212> TYPE: DNA
<213> ORGANISM: Artificial Sequence
<220> FEATURE:
<223> OTHER INFORMATION: Synthetic

<400> SEQUENCE: 195 gctgcatcc 9

<210> SEQ ID NO 196
<211> LENGTH: 3
<212> TYPE: PRT
<213> ORGANISM: Artificial Sequence
<220> FEATURE:
<223> OTHER INFORMATION: Synthetic

<400> SEQUENCE: 196

Ala Ala Ser
1

<210> SEQ ID NO 197
<211> LENGTH: 27
<212> TYPE: DNA
<213> ORGANISM: Artificial Sequence
<220> FEATURE:
<223> OTHER INFORMATION: Synthetic

<400> SEQUENCE: 197
ctacagtata atagttaccc gtggacg 27

<210> SEQ ID NO 198
<211> LENGTH: 9
<212> TYPE: PRT
<213> ORGANISM: Artificial Sequence
<220> FEATURE:
<223> OTHER INFORMATION: Synthetic

<400> SEQUENCE: 198

Leu Gln Tyr Asn Ser Tyr Pro Trp Thr
1 5

<210> SEQ ID NO 199
<211> LENGTH: 357
<212> TYPE: DNA
<213> ORGANISM: Artificial Sequence
<220> FEATURE:
<223> OTHER INFORMATION: Synthetic

<400> SEQUENCE: 199
caggtgcagc tggtgcagtc cggcgccgag gtgaagaagc ccggcgcctc cgtgaaggtg 60
tcctgcaagg tgtccggcta caccctgacc gagctgtcca tgcactgggt gcggcaggcc 120
cccggcaagg gcctggagtg gatgggcggc ttcgaccccg agcacggcga gaccatctac 180

```
gcccagaagt tccagggccg ggtgaccatg accgaggaca cctccaccga caccgcctac    240

atggagctgt cctccctgcg gtccgaggac accgccgtgt actactgcgc catgatcttc    300

ggcgtggtga ccaacttcga ctcctggggc cagggcaccc tggtgaccgt gtcctcc       357


<210> SEQ ID NO 200
<211> LENGTH: 119
<212> TYPE: PRT
<213> ORGANISM: Artificial Sequence
<220> FEATURE:
<223> OTHER INFORMATION: Synthetic

<400> SEQUENCE: 200

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu His Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Met Ile Phe Gly Val Val Thr Asn Phe Asp Ser Trp Gly Gln Gly
            100                 105                 110

Thr Leu Val Thr Val Ser Ser
        115


<210> SEQ ID NO 201
<211> LENGTH: 321
<212> TYPE: DNA
<213> ORGANISM: Artificial Sequence
<220> FEATURE:
<223> OTHER INFORMATION: Synthetic

<400> SEQUENCE: 201

gacatccaga tgacccagtc cccctcctcc ctgtccgcct ccgtgggcga ccgggtgacc     60

atcacctgcc gggcctccca gggcatccgg aacgacctgg gctggtacca gcagaagccc    120

ggcaaggccc ccaagcggct gatctacgcc gcctcctccc tgcagtccgg cgtgccctcc    180

cggttctccg gctccggctc cggcaccgag ttcaccctga ccatctcctc cctgcagccc    240

gaggacttcg ccacctacta ctgcctgcag tacaactcct acccctggac cttcggccag    300

ggcaccaagg tggagatcaa g                                              321


<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
```

```
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Tyr Pro Trp
                85                  90                  95

Thr Phe Gly Gln Gly Thr Lys Val Glu Ile Lys
            100                 105


<210> SEQ ID NO 203
<211> LENGTH: 357
<212> TYPE: DNA
<213> ORGANISM: Artificial Sequence
<220> FEATURE:
<223> OTHER INFORMATION: Synthetic

<400> SEQUENCE: 203

caggtgcagc tggtgcagtc tgggactgag gtgaagaagc ctggggcctc agtgaaggtc     60

tcctgcaagg tttccggata caccctcact gaattatcca tgtactgggt gcgacaggct    120

cctggaaaag ggcttgagtg gatgggaggt tttgatcctg aacatggtga aacaatctac    180

gcacagaagt tccagggcag agtcaccatg accgaggact catctacaga cacagcctac    240

atggagctga gcagcctgag atctgaggac acggccgtgt attactgtgc aatgattttt    300

ggagtggtta ccaactttga ctcctggggc ctgggaaccc tggtcactgt ctcctca       357


<210> SEQ ID NO 204
<211> LENGTH: 119
<212> TYPE: PRT
<213> ORGANISM: Artificial Sequence
<220> FEATURE:
<223> OTHER INFORMATION: Synthetic

<400> SEQUENCE: 204

Gln Val Gln Leu Val Gln Ser Gly Thr Glu Val Lys Lys Pro Gly Ala
 1               5                  10                  15

Ser Val Lys Val Ser Cys Lys Val Ser Gly Tyr Thr Leu Thr Glu Leu
            20                  25                  30

Ser Met Tyr Trp Val Arg Gln Ala Pro Gly Lys Gly Leu Glu Trp Met
        35                  40                  45

Gly Gly Phe Asp Pro Glu His Gly Glu Thr Ile Tyr Ala Gln Lys Phe
    50                  55                  60

Gln Gly Arg Val Thr Met Thr Glu Asp Ser Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Met Ile Phe Gly Val Val Thr Asn Phe Asp Ser Trp Gly Leu Gly
            100                 105                 110

Thr Leu Val Thr Val Ser Ser
        115


<210> SEQ ID NO 205
<211> LENGTH: 321
<212> TYPE: DNA
<213> ORGANISM: Artificial Sequence
<220> FEATURE:
<223> OTHER INFORMATION: Synthetic

<400> SEQUENCE: 205
```

gacatccaga tgacccagtc tccatcctcc ctgtctgcat ctgtaggaga cagagtcacc 60
atcacttgcc gggcaagtca gggcattaga aatgatttag gctggtatca gcagaaacca 120
gggaaagccc ctaagcgcct gatctatgct gcatccagtt tgcaaagtgg ggtcccatca 180
aggttcagcg gcagtggatc tgggacagaa ttcactctca caatcagcag cctgcagcct 240
gaagattttg caacttatta ctgtctacag tataatagtt acccgtggac gttcggccaa 300
gggaccaagg tggagatcaa a 321

<210> SEQ ID NO 206
<211> LENGTH: 107
<212> TYPE: PRT
<213> ORGANISM: Artificial Sequence
<220> FEATURE:
<223> OTHER INFORMATION: Synthetic

<400> SEQUENCE: 206

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Asp
20 25 30

Leu Gly Trp Tyr Gln Gln Lys Pro Gly Lys Ala Pro Lys Arg Leu Ile
35 40 45

Tyr Ala Ala Ser Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Leu Gln Tyr Asn Ser Tyr Pro Trp
85 90 95

Thr Phe Gly Gln Gly Thr Lys Val Glu Ile Lys
100 105

<210> SEQ ID NO 207
<211> LENGTH: 375
<212> TYPE: DNA
<213> ORGANISM: Artificial Sequence
<220> FEATURE:
<223> OTHER INFORMATION: Synthetic

<400> SEQUENCE: 207
gaagtgcagc tggtgcagtc tgggggcggc ttggtacagc ctggcaggtc cctgagactc 60
tcctgtgcag cccctggatt caactttgat gattatgcca tgcactgggt ccggcaaact 120
ccagggaagg gcctggagtg ggtctcaggt attagttgga atagtggtac tataggctat 180
gcggactctg tgaagggccg atttaccatc tccagagaca acgccaagaa ctccctgtat 240
cttcaaatga acagtctgag acctgaggac acggccttgt attactgtgc aaaagaaggg 300
gtatggttcg gaaaattgtt ctcatcctac ggtatggacg tctggggcca agggaccacg 360
gtcaccgtct cctca 375

<210> SEQ ID NO 208
<211> LENGTH: 125
<212> TYPE: PRT
<213> ORGANISM: Artificial Sequence
<220> FEATURE:
<223> OTHER INFORMATION: Synthetic

<400> SEQUENCE: 208

Glu Val Gln Leu Val Gln Ser Gly Gly Gly Leu Val Gln Pro Gly Arg
1 5 10 15

```
Ser Leu Arg Leu Ser Cys Ala Ala Pro Gly Phe Asn Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Leu Tyr Tyr Cys
                85                  90                  95

Ala Lys Glu Gly Val Trp Phe Gly Lys Leu Phe Ser Ser Tyr Gly Met
            100                 105                 110

Asp Val Trp Gly Gln Gly Thr Thr Val Thr Val Ser Ser
        115                 120                 125


<210> SEQ ID NO 209
<211> LENGTH: 24
<212> TYPE: DNA
<213> ORGANISM: Artificial Sequence
<220> FEATURE:
<223> OTHER INFORMATION: Synthetic

<400> SEQUENCE: 209

ggattcaact ttgatgatta tgcc                                            24


<210> SEQ ID NO 210
<211> LENGTH: 8
<212> TYPE: PRT
<213> ORGANISM: Artificial Sequence
<220> FEATURE:
<223> OTHER INFORMATION: Synthetic

<400> SEQUENCE: 210

Gly Phe Asn Phe Asp Asp Tyr Ala
 1               5


<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211

attagttgga atagtggtac tata                                            24


<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Ile Ser Trp Asn Ser Gly Thr Ile
 1               5


<210> SEQ ID NO 213
<211> LENGTH: 54
<212> TYPE: DNA
<213> ORGANISM: Artificial Sequence
<220> FEATURE:
<223> OTHER INFORMATION: Synthetic

<400> SEQUENCE: 213
```

gcaaaagaag gggtatggtt cggaaaattg ttctcatcct acggtatgga cgtc 54

<210> SEQ ID NO 214
<211> LENGTH: 18
<212> TYPE: PRT
<213> ORGANISM: Artificial Sequence
<220> FEATURE:
<223> OTHER INFORMATION: Synthetic

<400> SEQUENCE: 214

Ala Lys Glu Gly Val Trp Phe Gly Lys Leu Phe Ser Ser Tyr Gly Met
1 5 10 15

Asp Val

<210> SEQ ID NO 215
<211> LENGTH: 321
<212> TYPE: DNA
<213> ORGANISM: Artificial Sequence
<220> FEATURE:
<223> OTHER INFORMATION: Synthetic

<400> SEQUENCE: 215
gacatccgga tgacccagtc tccagccacc ctgtctgtgt ctccagggga aagagccacc 60
ctctcctgca gggccagtca gagtgttact tacaacttag actggtacca gcagaaacct 120
ggccaggctc ccaggctcct catctttggt gcatccacca gggccactgg tatcccagcc 180
aggttcagtg gcagtgggtc tgggacagag ttcactctca ccatcaccag cctgcagtct 240
gaagattttg cagtttatta ctgtcagcag tataataact ggccgtacac ttttggccag 300
gggaccaagg tggaaatcaa a 321

<210> SEQ ID NO 216
<211> LENGTH: 107
<212> TYPE: PRT
<213> ORGANISM: Artificial Sequence
<220> FEATURE:
<223> OTHER INFORMATION: Synthetic

<400> SEQUENCE: 216

Asp Ile Arg Met Thr Gln Ser Pro Ala Thr Leu Ser Val Ser Pro Gly
1 5 10 15

Glu Arg Ala Thr Leu Ser Cys Arg Ala Ser Gln Ser Val Thr Tyr Asn
20 25 30

Leu Asp Trp Tyr Gln Gln Lys Pro Gly Gln Ala Pro Arg Leu Leu Ile
35 40 45

Phe Gly Ala Ser Thr Arg Ala Thr Gly Ile Pro Ala Arg Phe Ser Gly
50 55 60

Ser Gly Ser Gly Thr Glu Phe Thr Leu Thr Ile Thr Ser Leu Gln Ser
65 70 75 80

Glu Asp Phe Ala Val Tyr Tyr Cys Gln Gln Tyr Asn Asn Trp Pro Tyr
85 90 95

Thr Phe Gly Gln Gly Thr Lys Val Glu Ile Lys
100 105

<210> SEQ ID NO 217
<211> LENGTH: 18
<212> TYPE: DNA
<213> ORGANISM: Artificial Sequence
<220> FEATURE:
<223> OTHER INFORMATION: Synthetic

<400> SEQUENCE: 217

```
cagagtgtta cttacaac                                                    18


<210> SEQ ID NO 218
<211> LENGTH: 6
<212> TYPE: PRT
<213> ORGANISM: Artificial Sequence
<220> FEATURE:
<223> OTHER INFORMATION: Synthetic

<400> SEQUENCE: 218

Gln Ser Val Thr Tyr Asn
1               5


<210> SEQ ID NO 219
<211> LENGTH: 9
<212> TYPE: DNA
<213> ORGANISM: Artificial Sequence
<220> FEATURE:
<223> OTHER INFORMATION: Synthetic

<400> SEQUENCE: 219

ggtgcatcc                                                               9


<210> SEQ ID NO 220
<211> LENGTH: 3
<212> TYPE: PRT
<213> ORGANISM: Artificial Sequence
<220> FEATURE:
<223> OTHER INFORMATION: Synthetic

<400> SEQUENCE: 220

Gly Ala Ser
1


<210> SEQ ID NO 221
<211> LENGTH: 27
<212> TYPE: DNA
<213> ORGANISM: Artificial Sequence
<220> FEATURE:
<223> OTHER INFORMATION: Synthetic

<400> SEQUENCE: 221

cagcagtata ataactggcc gtacact                                          27


<210> SEQ ID NO 222
<211> LENGTH: 9
<212> TYPE: PRT
<213> ORGANISM: Artificial Sequence
<220> FEATURE:
<223> OTHER INFORMATION: Synthetic

<400> SEQUENCE: 222

Gln Gln Tyr Asn Asn Trp Pro Tyr Thr
1               5


<210> SEQ ID NO 223
<211> LENGTH: 375
<212> TYPE: DNA
<213> ORGANISM: Artificial Sequence
<220> FEATURE:
<223> OTHER INFORMATION: Synthetic

<400> SEQUENCE: 223

gaggtgcagc tggtggagtc cggcggcggc ctggtgcagc ccggccggtc cctgcggctg      60

tcctgcgccg cccccggctt caacttcgac gactacgcca tgcactgggt gcggcaggcc     120
```

```
cccggcaagg gcctggagtg ggtgtccggc atctcctgga actccggcac catcggctac    180

gccgactccg tgaagggccg gttcaccatc tcccgggaca acgccaagaa ctccctgtac    240

ctgcagatga actccctgcg ggccgaggac accgccctgt actactgcgc caaggagggc    300

gtgtggttcg gcaagctgtt ctcctcctac ggcatggacg tgtggggcca gggcaccacc    360

gtgaccgtgt cctcc                                                     375


<210> SEQ ID NO 224
<211> LENGTH: 125
<212> TYPE: PRT
<213> ORGANISM: Artificial Sequence
<220> FEATURE:
<223> OTHER INFORMATION: Synthetic

<400> SEQUENCE: 224

Glu Val Gln Leu Val Glu Ser Gly Gly Gly Leu Val Gln Pro Gly Arg
 1               5                  10                  15

Ser Leu Arg Leu Ser Cys Ala Ala Pro Gly Phe Asn Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Val Trp Phe Gly Lys Leu Phe Ser Ser Tyr Gly Met
            100                 105                 110

Asp Val Trp Gly Gln Gly Thr Thr Val Thr Val Ser Ser
        115                 120                 125


<210> SEQ ID NO 225
<211> LENGTH: 324
<212> TYPE: DNA
<213> ORGANISM: Artificial Sequence
<220> FEATURE:
<223> OTHER INFORMATION: Synthetic

<400> SEQUENCE: 225

gagatcgtga tgacccagtc ccccgccacc ctgtccgtgt cccccggcga gcgggccacc     60

ctgtcctgcc gggcctccca gtccgtgacc tacaacctgg actggtacca gcagaagccc    120

ggccaggccc cccggctgct gatctacggc gcctccaccc gggccaccgg catccccgcc    180

cggttctccg gctccggctc cggcaccgag ttcaccctga ccatctcctc cctgcagtcc    240

gaggacttcg ccgtgtacta ctgccagcag tacaacaact ggccctacac cttcggccag    300

ggcaccaagc tggagatcaa gcgg                                           324


<210> SEQ ID NO 226
<211> LENGTH: 108
<212> TYPE: PRT
<213> ORGANISM: Artificial Sequence
<220> FEATURE:
<223> OTHER INFORMATION: Synthetic

<400> SEQUENCE: 226

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Thr Tyr Asn
```

```
            20                  25                  30

Leu Asp Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys Arg
            100                 105


<210> SEQ ID NO 227
<211> LENGTH: 375
<212> TYPE: DNA
<213> ORGANISM: Artificial Sequence
<220> FEATURE:
<223> OTHER INFORMATION: Synthetic

<400> SEQUENCE: 227

gaggtgcagc tggtggagtc cggcggcggc ctggtgcagc ccggccggtc cctgcggctg      60

tcctgcgccg cctccggctt caacttcgac gactacgcca tgcactgggt gcggcaggcc     120

cccggcaagg gcctggagtg ggtgtccggc atctcctgga actccggcac catcggctac     180

gccgactccg tgaagggccg gttcaccatc tcccgggaca acgccaagaa ctccctgtac     240

ctgcagatga actccctgcg ggccgaggac accgccctgt actactgcgc caaggagggc     300

gtgtggttcg gcaagctgtt ctcctcctac ggcatggacg tgtggggcca gggcaccacc     360

gtgaccgtgt cctcc                                                      375


<210> SEQ ID NO 228
<211> LENGTH: 125
<212> TYPE: PRT
<213> ORGANISM: Artificial Sequence
<220> FEATURE:
<223> OTHER INFORMATION: Synthetic

<400> SEQUENCE: 228

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Asn Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Val Trp Phe Gly Lys Leu Phe Ser Ser Tyr Gly Met
            100                 105                 110

Asp Val Trp Gly Gln Gly Thr Thr Val Thr Val Ser Ser
        115                 120                 125


<210> SEQ ID NO 229
<211> LENGTH: 324
<212> TYPE: DNA
<213> ORGANISM: Artificial Sequence
```

<220> FEATURE:
<223> OTHER INFORMATION: Synthetic

<400> SEQUENCE: 229
gagatcgtga tgacccagtc ccccgccacc ctgtccgtgt cccccggcga gcgggccacc 60
ctgtcctgcc gggcctccca gtccgtgacc tacaacctgg cctggtacca gcagaagccc 120
ggccaggccc cccggctgct gatctacggc gcctccaccc gggccaccgg catccccgcc 180
cggttctccg gctccggctc cggcaccgag ttcaccctga ccatctcctc cctgcagtcc 240
gaggacttcg ccgtgtacta ctgccagcag tacaacaact ggccctacac cttcggccag 300
ggcaccaagc tggagatcaa gcgg 324

<210> SEQ ID NO 230
<211> LENGTH: 108
<212> TYPE: PRT
<213> ORGANISM: Artificial Sequence
<220> FEATURE:
<223> OTHER INFORMATION: Synthetic

<400> SEQUENCE: 230

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Thr Tyr Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Tyr
85 90 95

Thr Phe Gly Gln Gly Thr Lys Leu Glu Ile Lys Arg
100 105

<210> SEQ ID NO 231
<211> LENGTH: 375
<212> TYPE: DNA
<213> ORGANISM: Artificial Sequence
<220> FEATURE:
<223> OTHER INFORMATION: Synthetic

<400> SEQUENCE: 231
gaagtgcagc tggtggagtc tgggggcggc ttggtacagc ctggcaggtc cctgagactc 60
tcctgtgcag cccctggatt caactttgat gattatgcca tgcactgggt ccggcaaact 120
ccagggaagg gcctggagtg ggtctcaggt attagttgga atagtggtac tataggctat 180
gcggactctg tgaagggccg atttaccatc tccagagaca acgccaagaa ctccctgtat 240
cttcaaatga acagtctgag acctgaggac acggccttgt attactgtgc aaaagaaggg 300
gtatggttcg gaaaattgtt ctcatcctac ggtatggacg tctggggcca agggaccacg 360
gtcaccgtct cctca 375

<210> SEQ ID NO 232
<211> LENGTH: 125
<212> TYPE: PRT
<213> ORGANISM: Artificial Sequence
<220> FEATURE:
<223> OTHER INFORMATION: Synthetic

<400> SEQUENCE: 232

```
Glu Val Gln Leu Val Glu Ser Gly Gly Gly Leu Val Gln Pro Gly Arg
 1               5                  10                  15

Ser Leu Arg Leu Ser Cys Ala Ala Pro Gly Phe Asn Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Leu Tyr Tyr Cys
                85                  90                  95

Ala Lys Glu Gly Val Trp Phe Gly Lys Leu Phe Ser Ser Tyr Gly Met
            100                 105                 110

Asp Val Trp Gly Gln Gly Thr Thr Val Thr Val Ser Ser
        115                 120                 125
```

<210> SEQ ID NO 233
<211> LENGTH: 324
<212> TYPE: DNA
<213> ORGANISM: Artificial Sequence
<220> FEATURE:
<223> OTHER INFORMATION: Synthetic

<400> SEQUENCE: 233

```
gaaatagtga tgacgcagtc tccagccacc ctgtctgtgt ctccagggga aagagccacc      60

ctctcctgca gggccagtca gagtgttact tacaacttag actggtacca gcagaaacct     120

ggccaggctc ccaggctcct catctttggt gcatccacca gggccactgg tatcccagcc     180

aggttcagtg gcagtgggtc tgggacagag ttcactctca ccatcaccag cctgcagtct     240

gaagattttg cagtttatta ctgtcagcag tataataact ggccgtacac ttttggccag     300

gggaccaagc tggagatcaa acga                                            324
```

<210> SEQ ID NO 234
<211> LENGTH: 108
<212> TYPE: PRT
<213> ORGANISM: Artificial Sequence
<220> FEATURE:
<223> OTHER INFORMATION: Synthetic

<400> SEQUENCE: 234

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Thr Tyr Asn
            20                  25                  30

Leu Asp Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
    50                  55                  60

Ser Gly Ser Gly Thr Glu Phe Thr Leu Thr Ile Thr Ser Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys Arg
            100                 105
```

<210> SEQ ID NO 235
<211> LENGTH: 375
<212> TYPE: DNA
<213> ORGANISM: Artificial Sequence
<220> FEATURE:
<223> OTHER INFORMATION: Synthetic

<400> SEQUENCE: 235

```
gaagtgcagc tggtggagtc tgggggcggc ttggtacagc ctggcaggtc cctgagactc     60

tcctgtgcag cctctggatt caactttgat gattatgcca tgcactgggt ccggcaaact    120

ccagggaagg gcctggagtg ggtctcaggt attagttgga atagtggtac tataggctat    180

gcggactctg tgaagggccg atttaccatc tccagagaca acgccaagaa ctccctgtat    240

cttcaaatga acagtctgag acctgaggac acggccttgt attactgtgc aaaagaaggg    300

gtatggttcg gaaaattgtt ctcatcctac ggtatggacg tctggggcca agggaccacg    360

gtcaccgtct cctca                                                     375
```

<210> SEQ ID NO 236
<211> LENGTH: 125
<212> TYPE: PRT
<213> ORGANISM: Artificial Sequence
<220> FEATURE:
<223> OTHER INFORMATION: Synthetic

<400> SEQUENCE: 236

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Asn Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Leu Tyr Tyr Cys
                85                  90                  95

Ala Lys Glu Gly Val Trp Phe Gly Lys Leu Phe Ser Ser Tyr Gly Met
            100                 105                 110

Asp Val Trp Gly Gln Gly Thr Thr Val Thr Val Ser Ser
        115                 120                 125
```

<210> SEQ ID NO 237
<211> LENGTH: 324
<212> TYPE: DNA
<213> ORGANISM: Artificial Sequence
<220> FEATURE:
<223> OTHER INFORMATION: Synthetic

<400> SEQUENCE: 237

```
gaaatagtga tgacgcagtc tccagccacc ctgtctgtgt ctccagggga aagagccacc     60

ctctcctgca gggccagtca gagtgttact tacaacttag cctggtacca gcagaaacct    120

ggccaggctc ccaggctcct catctttggt gcatccacca gggccactgg tatcccagcc    180

aggttcagtg gcagtgggtc tgggacagag ttcactctca ccatcaccag cctgcagtct    240

gaagattttg cagtttatta ctgtcagcag tataataact ggccgtacac ttttggccag    300

gggaccaagc tggagatcaa acga                                           324
```

<210> SEQ ID NO 238
<211> LENGTH: 108
<212> TYPE: PRT
<213> ORGANISM: Artificial Sequence
<220> FEATURE:
<223> OTHER INFORMATION: Synthetic

<400> SEQUENCE: 238

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Thr Tyr Asn
            20                  25                  30

Leu Ala Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
    50                  55                  60

Ser Gly Ser Gly Thr Glu Phe Thr Leu Thr Ile Thr Ser Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys Arg
            100                 105
```

<210> SEQ ID NO 239
<211> LENGTH: 357
<212> TYPE: DNA
<213> ORGANISM: Artificial Sequence
<220> FEATURE:
<223> OTHER INFORMATION: Synthetic

<400> SEQUENCE: 239

```
gaggtgcagc tggtgcagtc tggggctgag gtgaggaagc ctggggcctc agtgaaggtc      60

tcctgcaagg tttccggata caccctcact gaattatcca tacactgggt gcgacaggct     120

cctggaaaag ggcttgagtg gatgggaggt tttgatcctg aagatggtga aacaatctac     180

gcacagaagt tccagggcag agtcatcatg accgaggaca catctacaga cacagcctat     240

atggagctga gcagcctgag atctgaggac acggccgtgt attattgtgt aatgattttt     300

ggcgtggtta ccaactttga caactggggc cagggaaccc tggtcaccgt ctcctca        357
```

<210> SEQ ID NO 240
<211> LENGTH: 119
<212> TYPE: PRT
<213> ORGANISM: Artificial Sequence
<220> FEATURE:
<223> OTHER INFORMATION: Synthetic

<400> SEQUENCE: 240

```
Glu Val Gln Leu Val Gln Ser Gly Ala Glu Val Arg Lys Pro Gly Ala
 1               5                  10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Ile Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95
```

```
Val Met Ile Phe Gly Val Val Thr Asn Phe Asp Asn Trp Gly Gln Gly
            100                 105                 110

Thr Leu Val Thr Val Ser Ser
        115


<210> SEQ ID NO 241
<211> LENGTH: 24
<212> TYPE: DNA
<213> ORGANISM: Artificial Sequence
<220> FEATURE:
<223> OTHER INFORMATION: Synthetic

<400> SEQUENCE: 241

ggatacaccc tcactgaatt atcc                                            24


<210> SEQ ID NO 242
<211> LENGTH: 8
<212> TYPE: PRT
<213> ORGANISM: Artificial Sequence
<220> FEATURE:
<223> OTHER INFORMATION: Synthetic

<400> SEQUENCE: 242

Gly Tyr Thr Leu Thr Glu Leu Ser
 1               5


<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243

tttgatcctg aagatggtga aaca                                            24


<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Phe Asp Pro Glu Asp Gly Glu Thr
 1               5


<210> SEQ ID NO 245
<211> LENGTH: 36
<212> TYPE: DNA
<213> ORGANISM: Artificial Sequence
<220> FEATURE:
<223> OTHER INFORMATION: Synthetic

<400> SEQUENCE: 245

gtaatgattt ttggcgtggt taccaacttt gacaac                               36


<210> SEQ ID NO 246
<211> LENGTH: 12
<212> TYPE: PRT
<213> ORGANISM: Artificial Sequence
<220> FEATURE:
<223> OTHER INFORMATION: Synthetic

<400> SEQUENCE: 246

Val Met Ile Phe Gly Val Val Thr Asn Phe Asp Asn
 1               5                  10
```

<210> SEQ ID NO 247
<211> LENGTH: 321
<212> TYPE: DNA
<213> ORGANISM: Artificial Sequence
<220> FEATURE:
<223> OTHER INFORMATION: Synthetic

<400> SEQUENCE: 247
gaaattgtgc tgactcagtc tccatcctcc ctgtctgcat ccgtgagaga cagagtcacc 60
atcacttgcc gggcaagtca gggcattaga aatgatttag gctggtatca gcagaaacca 120
gggaaagccc ctaagcgcct gatctatgct gcatccagtt tgcaaagtgg ggtcccatca 180
aggttcagcg gcagtggatc tgggacagaa tccactctca caatcagcag cctgcagcct 240
gaagattttg caacttatta ttgttcacag tataatagtt acccgtggac gttcggccaa 300
gggaccaagg tggagatcaa a 321

<210> SEQ ID NO 248
<211> LENGTH: 107
<212> TYPE: PRT
<213> ORGANISM: Artificial Sequence
<220> FEATURE:
<223> OTHER INFORMATION: Synthetic

<400> SEQUENCE: 248

Glu Ile Val Leu Thr Gln Ser Pro Ser Ser Leu Ser Ala Ser Val Arg
1 5 10 15

Asp Arg Val Thr Ile Thr Cys Arg Ala Ser Gln Gly Ile Arg Asn Asp
20 25 30

Leu Gly Trp Tyr Gln Gln Lys Pro Gly Lys Ala Pro Lys Arg Leu Ile
35 40 45

Tyr Ala Ala Ser Ser Leu Gln Ser Gly Val Pro Ser Arg Phe Ser Gly
50 55 60

Ser Gly Ser Gly Thr Glu Ser Thr Leu Thr Ile Ser Ser Leu Gln Pro
65 70 75 80

Glu Asp Phe Ala Thr Tyr Tyr Cys Ser Gln Tyr Asn Ser Tyr Pro Trp
85 90 95

Thr Phe Gly Gln Gly Thr Lys Val Glu Ile Lys
100 105

<210> SEQ ID NO 249
<211> LENGTH: 18
<212> TYPE: DNA
<213> ORGANISM: Artificial Sequence
<220> FEATURE:
<223> OTHER INFORMATION: Synthetic

<400> SEQUENCE: 249
cagggcatta gaaatgat 18

<210> SEQ ID NO 250
<211> LENGTH: 6
<212> TYPE: PRT
<213> ORGANISM: Artificial Sequence
<220> FEATURE:
<223> OTHER INFORMATION: Synthetic

<400> SEQUENCE: 250

Gln Gly Ile Arg Asn Asp
1 5

<210> SEQ ID NO 251
<211> LENGTH: 9
<212> TYPE: DNA
<213> ORGANISM: Artificial Sequence
<220> FEATURE:
<223> OTHER INFORMATION: Synthetic

<400> SEQUENCE: 251 gctgcatcc 9

<210> SEQ ID NO 252
<211> LENGTH: 3
<212> TYPE: PRT
<213> ORGANISM: Artificial Sequence
<220> FEATURE:
<223> OTHER INFORMATION: Synthetic

<400> SEQUENCE: 252

Ala Ala Ser
1

<210> SEQ ID NO 253
<211> LENGTH: 27
<212> TYPE: DNA
<213> ORGANISM: Artificial Sequence
<220> FEATURE:
<223> OTHER INFORMATION: Synthetic

<400> SEQUENCE: 253
tcacagtata atagttaccc gtggacg 27

<210> SEQ ID NO 254
<211> LENGTH: 9
<212> TYPE: PRT
<213> ORGANISM: Artificial Sequence
<220> FEATURE:
<223> OTHER INFORMATION: Synthetic

<400> SEQUENCE: 254

Ser Gln Tyr Asn Ser Tyr Pro Trp Thr
1 5

<210> SEQ ID NO 255
<211> LENGTH: 357
<212> TYPE: DNA
<213> ORGANISM: Artificial Sequence
<220> FEATURE:
<223> OTHER INFORMATION: Synthetic

<400> SEQUENCE: 255
caggtgcagc tggtgcagtc cggcgccgag gtgaagaagc ccggcgcctc cgtgaaggtg 60
tcctgcaagg tgtccggcta caccctgacc gagctgtcca tgcactgggt gcggcaggcc 120
cccggcaagg gcctggagtg gatgggcggc ttcgaccccg aggacggcga gaccatctac 180
gcccagaagt tccagggccg ggtgaccatg accgaggaca cctccaccga caccgcctac 240
atggagctgt cctccctgcg gtccgaggac accgccgtgt actactgcgt gatgatcttc 300
ggcgtggtga ccaacttcga caactggggc cagggcaccc tggtgaccgt gtcctcc 357

<210> SEQ ID NO 256
<211> LENGTH: 119
<212> TYPE: PRT
<213> ORGANISM: Artificial Sequence
<220> FEATURE:
<223> OTHER INFORMATION: Synthetic

<400> SEQUENCE: 256

```
Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Met Ile Phe Gly Val Val Thr Asn Phe Asp Asn Trp Gly Gln Gly
            100                 105                 110

Thr Leu Val Thr Val Ser Ser
        115
```

<210> SEQ ID NO 257
<211> LENGTH: 321
<212> TYPE: DNA
<213> ORGANISM: Artificial Sequence
<220> FEATURE:
<223> OTHER INFORMATION: Synthetic

<400> SEQUENCE: 257

```
gacatccaga tgacccagtc cccctcctcc ctgtccgcct ccgtgggcga ccgggtgacc      60

atcacctgcc gggcctccca gggcatccgg aacgacctgg gctggtacca gcagaagccc     120

ggcaaggccc ccaagcggct gatctacgcc gcctcctccc tgcagtccgg cgtgccctcc     180

cggttctccg gctccggctc cggcaccgag ttcaccctga ccatctcctc cctgcagccc     240

gaggacttcg ccacctacta ctgctcccag tacaactcct acccctggac cttcggccag     300

ggcaccaagg tggagatcaa g                                               321
```

<210> SEQ ID NO 258
<211> LENGTH: 107
<212> TYPE: PRT
<213> ORGANISM: Artificial Sequence
<220> FEATURE:
<223> OTHER INFORMATION: Synthetic

<400> SEQUENCE: 258

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Ser Gln Tyr Asn Ser Tyr Pro Trp
                85                  90                  95

Thr Phe Gly Gln Gly Thr Lys Val Glu Ile Lys
            100                 105
```

<210> SEQ ID NO 259

<211> LENGTH: 357
<212> TYPE: DNA
<213> ORGANISM: Artificial Sequence
<220> FEATURE:
<223> OTHER INFORMATION: Synthetic

<400> SEQUENCE: 259
caggtgcagc tggtgcagtc tggggctgag gtgaggaagc ctggggcctc agtgaaggtc 60
tcctgcaagg tttccggata caccctcact gaattatcca tacactgggt gcgacaggct 120
cctggaaaag ggcttgagtg gatgggaggt tttgatcctg aagatggtga aacaatctac 180
gcacagaagt tccagggcag agtcatcatg accgaggaca catctacaga cacagcctat 240
atggagctga gcagcctgag atctgaggac acggccgtgt attattgtgt aatgattttt 300
ggcgtggtta ccaactttga caactggggc cagggaaccc tggtcaccgt ctcctca 357

<210> SEQ ID NO 260
<211> LENGTH: 119
<212> TYPE: PRT
<213> ORGANISM: Artificial Sequence
<220> FEATURE:
<223> OTHER INFORMATION: Synthetic

<400> SEQUENCE: 260

Gln Val Gln Leu Val Gln Ser Gly Ala Glu Val Arg Lys Pro Gly Ala
1 5 10 15

Ser Val Lys Val Ser Cys Lys Val Ser Gly Tyr Thr Leu Thr Glu Leu
20 25 30

Ser Ile His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Phe
50 55 60

Gln Gly Arg Val Ile Met Thr Glu Asp Thr Ser Thr Asp Thr Ala Tyr
65 70 75 80

Met Glu Leu Ser Ser Leu Arg Ser Glu Asp Thr Ala Val Tyr Tyr Cys
85 90 95

Val Met Ile Phe Gly Val Val Thr Asn Phe Asp Asn Trp Gly Gln Gly
100 105 110

Thr Leu Val Thr Val Ser Ser
115

<210> SEQ ID NO 261
<211> LENGTH: 321
<212> TYPE: DNA
<213> ORGANISM: Artificial Sequence
<220> FEATURE:
<223> OTHER INFORMATION: Synthetic

<400> SEQUENCE: 261
gacatccaga tgacccagtc tccatcctcc ctgtctgcat ccgtgagaga cagagtcacc 60
atcacttgcc gggcaagtca gggcattaga aatgatttag gctggtatca gcagaaacca 120
gggaaagccc ctaagcgcct gatctatgct gcatccagtt tgcaaagtgg ggtcccatca 180
aggttcagcg gcagtggatc tgggacagaa tccactctca caatcagcag cctgcagcct 240
gaagattttg caacttatta ttgttcacag tataatagtt acccgtggac gttcggccaa 300
gggaccaagg tggaaatcaa a 321

<210> SEQ ID NO 262
<211> LENGTH: 107
<212> TYPE: PRT

<213> ORGANISM: Artificial Sequence
<220> FEATURE:
<223> OTHER INFORMATION: Synthetic

<400> SEQUENCE: 262

```
Asp Ile Gln Met Thr Gln Ser Pro Ser Ser Leu Ser Ala Ser Val Arg
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Ser Thr Leu Thr Ile Ser Ser Leu Gln Pro
65                  70                  75                  80

Glu Asp Phe Ala Thr Tyr Tyr Cys Ser Gln Tyr Asn Ser Tyr Pro Trp
                85                  90                  95

Thr Phe Gly Gln Gly Thr Lys Val Glu Ile Lys
            100                 105
```

<210> SEQ ID NO 263
<211> LENGTH: 357
<212> TYPE: DNA
<213> ORGANISM: Artificial Sequence
<220> FEATURE:
<223> OTHER INFORMATION: Synthetic

<400> SEQUENCE: 263

```
gaagtgcagc tggtgcagtc tggggctgag gtgaagaagc ctggggcctc agtgaaggtc     60

tcctgcaagg tttccggatt caccctcact gaattatcca ttcactgggt gcgacaggct    120

cctggaaaag ggcttgagtg gatgggaggt tttgatcctg aagatggtga aacaatctac    180

gcacagaagt tccagggcag agtcaccatg accgaggaca catctacaga cacagcctac    240

atggagctga gcagcctgag atctgaagac acggccgtgt attactgttc aacgattttt    300

ggagtggtta ccaactttga caactggggc cagggaaccc tggtcaccgt ctcctca       357
```

<210> SEQ ID NO 264
<211> LENGTH: 119
<212> TYPE: PRT
<213> ORGANISM: Artificial Sequence
<220> FEATURE:
<223> OTHER INFORMATION: Synthetic

<400> SEQUENCE: 264

```
Glu Val Gln Leu Val Gln Ser Gly Ala Glu Val Lys Lys Pro Gly Ala
 1               5                  10                  15

Ser Val Lys Val Ser Cys Lys Val Ser Gly Phe Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ser Thr Ile Phe Gly Val Val Thr Asn Phe Asp Asn Trp Gly Gln Gly
            100                 105                 110
```

```
Thr Leu Val Thr Val Ser Ser
        115


<210> SEQ ID NO 265
<211> LENGTH: 24
<212> TYPE: DNA
<213> ORGANISM: Artificial Sequence
<220> FEATURE:
<223> OTHER INFORMATION: Synthetic

<400> SEQUENCE: 265

ggattcaccc tcactgaatt atcc                                            24


<210> SEQ ID NO 266
<211> LENGTH: 8
<212> TYPE: PRT
<213> ORGANISM: Artificial Sequence
<220> FEATURE:
<223> OTHER INFORMATION: Synthetic

<400> SEQUENCE: 266

Gly Phe Thr Leu Thr Glu Leu Ser
 1               5


<210> SEQ ID NO 267
<211> LENGTH: 24
<212> TYPE: DNA
<213> ORGANISM: Artificial Sequence
<220> FEATURE:
<223> OTHER INFORMATION: Synthetic

<400> SEQUENCE: 267

tttgatcctg aagatggtga aaca                                            24


<210> SEQ ID NO 268
<211> LENGTH: 8
<212> TYPE: PRT
<213> ORGANISM: Artificial Sequence
<220> FEATURE:
<223> OTHER INFORMATION: Synthetic

<400> SEQUENCE: 268

Phe Asp Pro Glu Asp Gly Glu Thr
 1               5


<210> SEQ ID NO 269
<211> LENGTH: 36
<212> TYPE: DNA
<213> ORGANISM: Artificial Sequence
<220> FEATURE:
<223> OTHER INFORMATION: Synthetic

<400> SEQUENCE: 269

tcaacgattt ttggagtggt taccaacttt gacaac                               36


<210> SEQ ID NO 270
<211> LENGTH: 12
<212> TYPE: PRT
<213> ORGANISM: Artificial Sequence
<220> FEATURE:
<223> OTHER INFORMATION: Synthetic

<400> SEQUENCE: 270

Ser Thr Ile Phe Gly Val Val Thr Asn Phe Asp Asn
 1               5                  10


<210> SEQ ID NO 271
```

<211> LENGTH: 321
<212> TYPE: DNA
<213> ORGANISM: Artificial Sequence
<220> FEATURE:
<223> OTHER INFORMATION: Synthetic

<400> SEQUENCE: 271

```
gccatccagt tgacccagtc tccatcctcc ctgtctgcat ctgcaggaga cagagtcacc     60

atcacttgcc gggcaagtca ggccattaga aatgatttag gctggtatca gcagaaacca    120

gggaaagccc ctaagcgcct ggtctatgct gcattcaatt tgcaaagtgg ggtcccatca    180

agattcagcg gcagtggatc tgggacagaa ttcactctca caatcagtag cctgcagcct    240

gaagatcttg caacttatta ctgtctacag tataatagtt acccgtggac gttcggccaa    300

gggaccaaag tggatatcaa a                                              321
```

<210> SEQ ID NO 272
<211> LENGTH: 107
<212> TYPE: PRT
<213> ORGANISM: Artificial Sequence
<220> FEATURE:
<223> OTHER INFORMATION: Synthetic

<400> SEQUENCE: 272

```
Ala Ile Gln Leu Thr Gln Ser Pro Ser Ser Leu Ser Ala Ser Ala Gly
 1               5                  10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Val
        35                  40                  45

Tyr Ala Ala Phe Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Leu Ala Thr Tyr Tyr Cys Leu Gln Tyr Asn Ser Tyr Pro Trp
                85                  90                  95

Thr Phe Gly Gln Gly Thr Lys Val Asp Ile Lys
            100                 105
```

<210> SEQ ID NO 273
<211> LENGTH: 18
<212> TYPE: DNA
<213> ORGANISM: Artificial Sequence
<220> FEATURE:
<223> OTHER INFORMATION: Synthetic

<400> SEQUENCE: 273

```
caggccatta gaaatgat                                                   18
```

<210> SEQ ID NO 274
<211> LENGTH: 6
<212> TYPE: PRT
<213> ORGANISM: Artificial Sequence
<220> FEATURE:
<223> OTHER INFORMATION: Synthetic

<400> SEQUENCE: 274

```
Gln Ala Ile Arg Asn Asp
 1               5
```

<210> SEQ ID NO 275
<211> LENGTH: 9
<212> TYPE: DNA

<213> ORGANISM: Artificial Sequence
<220> FEATURE:
<223> OTHER INFORMATION: Synthetic

<400> SEQUENCE: 275 gctgcattc 9

<210> SEQ ID NO 276
<211> LENGTH: 3
<212> TYPE: PRT
<213> ORGANISM: Artificial Sequence
<220> FEATURE:
<223> OTHER INFORMATION: Synthetic

<400> SEQUENCE: 276

Ala Ala Phe
1

<210> SEQ ID NO 277
<211> LENGTH: 27
<212> TYPE: DNA
<213> ORGANISM: Artificial Sequence
<220> FEATURE:
<223> OTHER INFORMATION: Synthetic

<400> SEQUENCE: 277
ctacagtata atagttaccc gtggacg 27

<210> SEQ ID NO 278
<211> LENGTH: 9
<212> TYPE: PRT
<213> ORGANISM: Artificial Sequence
<220> FEATURE:
<223> OTHER INFORMATION: Synthetic

<400> SEQUENCE: 278

Leu Gln Tyr Asn Ser Tyr Pro Trp Thr
1 5

<210> SEQ ID NO 279
<211> LENGTH: 357
<212> TYPE: DNA
<213> ORGANISM: Artificial Sequence
<220> FEATURE:
<223> OTHER INFORMATION: Synthetic

<400> SEQUENCE: 279
caggtgcagc tggtgcagtc cggcgccgag gtgaagaagc ccggcgcctc cgtgaaggtg 60
tcctgcaagg tgtccggctt caccctgacc gagctgtcca tgcactgggt gcggcaggcc 120
cccggcaagg gcctggagtg gatgggcggc ttcgaccccg aggacggcga gaccatctac 180
gcccagaagt tccagggccg ggtgaccatg accgaggaca cctccaccga caccgcctac 240
atggagctgt cctccctgcg gtccgaggac accgccgtgt actactgctc caccatcttc 300
ggcgtggtga ccaacttcga caactggggc cagggcaccc tggtgaccgt gtcctcc 357

<210> SEQ ID NO 280
<211> LENGTH: 119
<212> TYPE: PRT
<213> ORGANISM: Artificial Sequence
<220> FEATURE:
<223> OTHER INFORMATION: Synthetic

<400> SEQUENCE: 280

Gln Val Gln Leu Val Gln Ser Gly Ala Glu Val Lys Lys Pro Gly Ala
1 5 10 15

```
Ser Val Lys Val Ser Cys Lys Val Ser Gly Phe Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ser Thr Ile Phe Gly Val Val Thr Asn Phe Asp Asn Trp Gly Gln Gly
            100                 105                 110

Thr Leu Val Thr Val Ser Ser
        115


<210> SEQ ID NO 281
<211> LENGTH: 321
<212> TYPE: DNA
<213> ORGANISM: Artificial Sequence
<220> FEATURE:
<223> OTHER INFORMATION: Synthetic

<400> SEQUENCE: 281

gacatccaga tgacccagtc cccctcctcc ctgtccgcct ccgtgggcga ccgggtgacc      60

atcacctgcc gggcctccca ggccatccgg aacgacctgg gctggtacca gcagaagccc     120

ggcaaggccc ccaagcggct gatctacgcc gccttctccc tgcagtccgg cgtgccctcc     180

cggttctccg gctccggctc cggcaccgag ttcaccctga ccatctcctc cctgcagccc     240

gaggacttcg ccacctacta ctgcctgcag tacaactcct acccctggac cttcggccag     300

ggcaccaagg tggagatcaa g                                               321


<210> SEQ ID NO 282
<211> LENGTH: 107
<212> TYPE: PRT
<213> ORGANISM: Artificial Sequence
<220> FEATURE:
<223> OTHER INFORMATION: Synthetic

<400> SEQUENCE: 282

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Phe Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Tyr Pro Trp
                85                  90                  95

Thr Phe Gly Gln Gly Thr Lys Val Glu Ile Lys
            100                 105


<210> SEQ ID NO 283
<211> LENGTH: 357
<212> TYPE: DNA
<213> ORGANISM: Artificial Sequence
```

<220> FEATURE:
<223> OTHER INFORMATION: Synthetic

<400> SEQUENCE: 283

```
caggtgcagc tggtgcagtc tggggctgag gtgaagaagc ctggggcctc agtgaaggtc     60

tcctgcaagg tttccggatt caccctcact gaattatcca ttcactgggt gcgacaggct    120

cctggaaaag ggcttgagtg gatgggaggt tttgatcctg aagatggtga aacaatctac    180

gcacagaagt tccagggcag agtcaccatg accgaggaca catctacaga cacagcctac    240

atggagctga gcagcctgag atctgaagac acggccgtgt attactgttc aacgattttt    300

ggagtggtta ccaactttga caactggggc cagggaaccc tggtcaccgt ctcctca       357
```

<210> SEQ ID NO 284
<211> LENGTH: 119
<212> TYPE: PRT
<213> ORGANISM: Artificial Sequence
<220> FEATURE:
<223> OTHER INFORMATION: Synthetic

<400> SEQUENCE: 284

```
Gln Val Gln Leu Val Gln Ser Gly Ala Glu Val Lys Lys Pro Gly Ala
1               5                   10                  15

Ser Val Lys Val Ser Cys Lys Val Ser Gly Phe Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ser Thr Ile Phe Gly Val Val Thr Asn Phe Asp Asn Trp Gly Gln Gly
            100                 105                 110

Thr Leu Val Thr Val Ser Ser
        115
```

<210> SEQ ID NO 285
<211> LENGTH: 321
<212> TYPE: DNA
<213> ORGANISM: Artificial Sequence
<220> FEATURE:
<223> OTHER INFORMATION: Synthetic

<400> SEQUENCE: 285

```
gacatccaga tgacccagtc tccatcctcc ctgtctgcat ctgcaggaga cagagtcacc     60

atcacttgcc gggcaagtca ggccattaga aatgatttag gctggtatca gcagaaacca    120

gggaaagccc ctaagcgcct ggtctatgct gcattcaatt tgcaaagtgg ggtcccatca    180

agattcagcg gcagtggatc tgggacagaa ttcactctca caatcagtag cctgcagcct    240

gaagatcttg caacttatta ctgtctacag tataatagtt acccgtggac gttcggccaa    300

gggaccaagg tggaaatcaa a                                              321
```

<210> SEQ ID NO 286
<211> LENGTH: 107
<212> TYPE: PRT
<213> ORGANISM: Artificial Sequence
<220> FEATURE:
<223> OTHER INFORMATION: Synthetic

<400> SEQUENCE: 286

```
Asp Ile Gln Met Thr Gln Ser Pro Ser Ser Leu Ser Ala Ser Ala Gly
 1               5                  10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Val
        35                  40                  45

Tyr Ala Ala Phe Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Leu Ala Thr Tyr Tyr Cys Leu Gln Tyr Asn Ser Tyr Pro Trp
                85                  90                  95

Thr Phe Gly Gln Gly Thr Lys Val Glu Ile Lys
            100                 105
```

<210> SEQ ID NO 287
<211> LENGTH: 375
<212> TYPE: DNA
<213> ORGANISM: Artificial Sequence
<220> FEATURE:
<223> OTHER INFORMATION: Synthetic

<400> SEQUENCE: 287

```
gaggtgcagc tggtgcagtc tgggggaggc tcggtacagc ctggcaggtc cctgagactc     60

tcctgtgcag cctctggatt cacttttgat gattattcca tgcactgggt ccggcaaggt    120

ccagggaagg gcctggaatg ggtctcaggt attagttgga atagtggaac tatagtctat    180

gcggactctg tgaagggccg attcaccatc tccagagaca acgtcaagaa caccctgtat    240

ctgcaaatga aaagtctgag agatgaggac acggccgtat attactgtgc aaaagaaggg    300

gtatggttcg ggagattatt ttcatcctac ggtatggacg tctggggcca agggaccctg    360

gtcaccgtct cctca                                                     375
```

<210> SEQ ID NO 288
<211> LENGTH: 125
<212> TYPE: PRT
<213> ORGANISM: Artificial Sequence
<220> FEATURE:
<223> OTHER INFORMATION: Synthetic

<400> SEQUENCE: 288

```
Glu Val Gln Leu Val Gln Ser Gly Gly Gly Ser Val Gln Pro Gly Arg
 1               5                  10                  15

Ser Leu Arg Leu Ser Cys Ala Ala Ser Gly Phe Thr Phe Asp Asp Tyr
            20                  25                  30

Ser Met His Trp Val Arg Gln Gly Pro Gly Lys Gly Leu Glu Trp Val
        35                  40                  45

Ser Gly Ile Ser Trp Asn Ser Gly Thr Ile Val Tyr Ala Asp Ser Val
    50                  55                  60

Lys Gly Arg Phe Thr Ile Ser Arg Asp Asn Val Lys Asn Thr Leu Tyr
65                  70                  75                  80

Leu Gln Met Lys Ser Leu Arg Asp Glu Asp Thr Ala Val Tyr Tyr Cys
                85                  90                  95

Ala Lys Glu Gly Val Trp Phe Gly Arg Leu Phe Ser Ser Tyr Gly Met
            100                 105                 110

Asp Val Trp Gly Gln Gly Thr Leu Val Thr Val Ser Ser
```

115 120 125

<210> SEQ ID NO 289
<211> LENGTH: 24
<212> TYPE: DNA
<213> ORGANISM: Artificial Sequence
<220> FEATURE:
<223> OTHER INFORMATION: Synthetic

<400> SEQUENCE: 289
ggattcactt ttgatgatta ttcc 24

<210> SEQ ID NO 290
<211> LENGTH: 8
<212> TYPE: PRT
<213> ORGANISM: Artificial Sequence
<220> FEATURE:
<223> OTHER INFORMATION: Synthetic

<400> SEQUENCE: 290

Gly Phe Thr Phe Asp Asp Tyr Ser
1 5

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
attagttgga atagtggaac tata 24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Ile Ser Trp Asn Ser Gly Thr Ile
1 5

<210> SEQ ID NO 293
<211> LENGTH: 54
<212> TYPE: DNA
<213> ORGANISM: Artificial Sequence
<220> FEATURE:
<223> OTHER INFORMATION: Synthetic

<400> SEQUENCE: 293
gcaaaagaag ggtatggtt cgggagatta ttttcatcct acggtatgga cgtc 54

<210> SEQ ID NO 294
<211> LENGTH: 16
<212> TYPE: PRT
<213> ORGANISM: Artificial Sequence
<220> FEATURE:
<223> OTHER INFORMATION: Synthetic

<400> SEQUENCE: 294

Ala Lys Glu Gly Val Trp Phe Gly Arg Leu Phe Ser Ser Tyr Gly Met
1 5 10 15

<210> SEQ ID NO 295
<211> LENGTH: 321

<212> TYPE: DNA
<213> ORGANISM: Artificial Sequence
<220> FEATURE:
<223> OTHER INFORMATION: Synthetic

<400> SEQUENCE: 295

```
gacatccgga tgacccagtc tccagccacc ctgtctgtgt ctccagggga aagagccacc     60

ctctcctgca gggccagtcc gagtgttagc agcaacttag cctggtacca gcagagacct    120

ggccagcctc ccaggctcct catctatggt gcatccacca gggccactgg tatcccagcc    180

aggttcagtg gcagtgggtc tgggacagag ttcactctca ccatcagcag cctgcagtct    240

gaagattttg cagtttatta ctgtcaacag tatagtaact ggccgtacac ttttggccag    300

gggaccaagg tggagatcaa a                                              321
```

<210> SEQ ID NO 296
<211> LENGTH: 107
<212> TYPE: PRT
<213> ORGANISM: Artificial Sequence
<220> FEATURE:
<223> OTHER INFORMATION: Synthetic

<400> SEQUENCE: 296

```
Asp Ile Arg Met Thr Gln Ser Pro Ala Thr Leu Ser Val Ser Pro Gly
 1               5                  10                  15

Glu Arg Ala Thr Leu Ser Cys Arg Ala Ser Pro Ser Val Ser Ser Asn
            20                  25                  30

Leu Ala Trp Tyr Gln Gln Arg Pro Gly Gln Pro Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Asn Trp Pro Tyr
                85                  90                  95

Thr Phe Gly Gln Gly Thr Lys Val Glu Ile Lys
            100                 105
```

<210> SEQ ID NO 297
<211> LENGTH: 18
<212> TYPE: DNA
<213> ORGANISM: Artificial Sequence
<220> FEATURE:
<223> OTHER INFORMATION: Synthetic

<400> SEQUENCE: 297

```
ccgagtgtta gcagcaac                                                   18
```

<210> SEQ ID NO 298
<211> LENGTH: 6
<212> TYPE: PRT
<213> ORGANISM: Artificial Sequence
<220> FEATURE:
<223> OTHER INFORMATION: Synthetic

<400> SEQUENCE: 298

```
Pro Ser Val Ser Ser Asn
 1               5
```

<210> SEQ ID NO 299
<211> LENGTH: 9
<212> TYPE: DNA
<213> ORGANISM: Artificial Sequence
<220> FEATURE:
<223> OTHER INFORMATION: Synthetic

<400> SEQUENCE: 299 ggtgcatcc 9

<210> SEQ ID NO 300
<211> LENGTH: 3
<212> TYPE: PRT
<213> ORGANISM: Artificial Sequence
<220> FEATURE:
<223> OTHER INFORMATION: Synthetic

<400> SEQUENCE: 300

Gly Ala Ser
1

<210> SEQ ID NO 301
<211> LENGTH: 27
<212> TYPE: DNA
<213> ORGANISM: Artificial Sequence
<220> FEATURE:
<223> OTHER INFORMATION: Synthetic

<400> SEQUENCE: 301
caacagtata gtaactggcc gtacact 27

<210> SEQ ID NO 302
<211> LENGTH: 9
<212> TYPE: PRT
<213> ORGANISM: Artificial Sequence
<220> FEATURE:
<223> OTHER INFORMATION: Synthetic

<400> SEQUENCE: 302

Gln Gln Tyr Ser Asn Trp Pro Tyr Thr
1 5

<210> SEQ ID NO 303
<211> LENGTH: 375
<212> TYPE: DNA
<213> ORGANISM: Artificial Sequence
<220> FEATURE:
<223> OTHER INFORMATION: Synthetic

<400> SEQUENCE: 303
gaggtgcagc tggtggagtc cggcggcggc ctggtgcagc ccggccggtc cctgcggctg 60
tcctgcgccg cctccggctt caccttcgac gactactcca tgcactgggt gcggcaggcc 120
cccggcaagg gcctggagtg ggtgtccggc atctcctgga actccggcac catcggctac 180
gccgactccg tgaagggccg gttcaccatc tcccgggaca acgccaagaa ctccctgtac 240
ctgcagatga actccctgcg ggccgaggac accgccctgt actactgcgc caaggagggc 300
gtgtggttcg gccggctgtt ctcctcctac ggcatggacg tgtggggcca gggcaccacc 360
gtgaccgtgt cctcc 375

<210> SEQ ID NO 304
<211> LENGTH: 125
<212> TYPE: PRT
<213> ORGANISM: Artificial Sequence
<220> FEATURE:
<223> OTHER INFORMATION: Synthetic

<400> SEQUENCE: 304

Glu Val Gln Leu Val Glu Ser Gly Gly Gly Leu Val Gln Pro Gly Arg

```
 1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Val Trp Phe Gly Arg Leu Phe Ser Ser Tyr Gly Met
            100                 105                 110

Asp Val Trp Gly Gln Gly Thr Thr Val Thr Val Ser Ser
        115                 120                 125
```

<210> SEQ ID NO 305
<211> LENGTH: 321
<212> TYPE: DNA
<213> ORGANISM: Artificial Sequence
<220> FEATURE:
<223> OTHER INFORMATION: Synthetic

<400> SEQUENCE: 305

```
gagatcgtga tgacccagtc ccccgccacc ctgtccgtgt cccccggcga gcgggccacc     60

ctgtcctgcc gggcctcccc ctccgtgtcc tccaacctgg cctggtacca gcagaagccc    120

ggccaggccc cccggctgct gatctacggc gcctccaccc gggccaccgg catccccgcc    180

cggttctccg gctccggctc cggcaccgag ttcaccctga ccatctcctc cctgcagtcc    240

gaggacttcg ccgtgtacta ctgccagcag tactccaact ggccctacac cttcggccag    300

ggcaccaagc tggagatcaa g                                              321
```

<210> SEQ ID NO 306
<211> LENGTH: 107
<212> TYPE: PRT
<213> ORGANISM: Artificial Sequence
<220> FEATURE:
<223> OTHER INFORMATION: Synthetic

<400> SEQUENCE: 306

```
Glu Ile Val Met Thr Gln Ser Pro Ala Thr Leu Ser Val Ser Pro Gly
 1               5                   10                  15

Glu Arg Ala Thr Leu Ser Cys Arg Ala Ser Pro Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Asn Trp Pro Tyr
                85                  90                  95

Thr Phe Gly Gln Gly Thr Lys Leu Glu Ile Lys
            100                 105
```

<210> SEQ ID NO 307
<211> LENGTH: 375
<212> TYPE: DNA

<213> ORGANISM: Artificial Sequence
<220> FEATURE:
<223> OTHER INFORMATION: Synthetic

<400> SEQUENCE: 307

```
gaggtgcagc tggtggagtc tgggggaggc tcggtacagc ctggcaggtc cctgagactc     60

tcctgtgcag cctctggatt cacttttgat gattattcca tgcactgggt ccggcaaggt    120

ccagggaagg gcctggaatg ggtctcaggt attagttgga atagtggaac tatagtctat    180

gcggactctg tgaagggccg attcaccatc tccagagaca acgtcaagaa caccctgtat    240

ctgcaaatga aaagtctgag agatgaggac acggccgtat attactgtgc aaaagaaggg    300

gtatggttcg ggagattatt ttcatcctac ggtatggacg tctggggcca agggaccacg    360

gtcaccgtct cctca                                                     375
```

<210> SEQ ID NO 308
<211> LENGTH: 125
<212> TYPE: PRT
<213> ORGANISM: Artificial Sequence
<220> FEATURE:
<223> OTHER INFORMATION: Synthetic

<400> SEQUENCE: 308

```
Glu Val Gln Leu Val Glu Ser Gly Gly Gly Ser Val Gln Pro Gly Arg
 1               5                  10                  15

Ser Leu Arg Leu Ser Cys Ala Ala Ser Gly Phe Thr Phe Asp Asp Tyr
            20                  25                  30

Ser Met His Trp Val Arg Gln Gly Pro Gly Lys Gly Leu Glu Trp Val
        35                  40                  45

Ser Gly Ile Ser Trp Asn Ser Gly Thr Ile Val Tyr Ala Asp Ser Val
    50                  55                  60

Lys Gly Arg Phe Thr Ile Ser Arg Asp Asn Val Lys Asn Thr Leu Tyr
65                  70                  75                  80

Leu Gln Met Lys Ser Leu Arg Asp Glu Asp Thr Ala Val Tyr Tyr Cys
                85                  90                  95

Ala Lys Glu Gly Val Trp Phe Gly Arg Leu Phe Ser Ser Tyr Gly Met
            100                 105                 110

Asp Val Trp Gly Gln Gly Thr Thr Val Thr Val Ser Ser
        115                 120                 125
```

<210> SEQ ID NO 309
<211> LENGTH: 321
<212> TYPE: DNA
<213> ORGANISM: Artificial Sequence
<220> FEATURE:
<223> OTHER INFORMATION: Synthetic

<400> SEQUENCE: 309

```
gaaatagtga tgacgcagtc tccagccacc ctgtctgtgt ctccagggga aagagccacc     60

ctctcctgca gggccagtcc gagtgttagc agcaacttag cctggtacca gcagagacct    120

ggccagcctc ccaggctcct catctatggt gcatccacca gggccactgg tatcccagcc    180

aggttcagtg gcagtgggtc tgggacagag ttcactctca ccatcagcag cctgcagtct    240

gaagattttg cagtttatta ctgtcaacag tatagtaact ggccgtacac ttttggccag    300

gggaccaagc tggagatcaa a                                              321
```

<210> SEQ ID NO 310
<211> LENGTH: 107
<212> TYPE: PRT

<213> ORGANISM: Artificial Sequence
<220> FEATURE:
<223> OTHER INFORMATION: Synthetic

<400> SEQUENCE: 310

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Pro Ser Val Ser Ser Asn
            20                  25                  30

Leu Ala Trp Tyr Gln Gln Arg Pro Gly Gln Pro Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Asn Trp Pro Tyr
                85                  90                  95

Thr Phe Gly Gln Gly Thr Lys Leu Glu Ile Lys
            100                 105
```

<210> SEQ ID NO 311
<211> LENGTH: 375
<212> TYPE: DNA
<213> ORGANISM: Artificial Sequence
<220> FEATURE:
<223> OTHER INFORMATION: Synthetic

<400> SEQUENCE: 311

```
caggtccagc tggtacagtc tggggaggc ttggtacagc ctggcaggtc cctgaaactc     60

tcctgtgcag cctctagatt cacctttgaa gattatgcca tgcactgggt ccggcaagct    120

ccagggaagg gcctggaatg ggtctcaggg attagttgga atagtggtag tataggttat    180

gcggactctg tgaagggccg attcaccatc tccagagaca acgccaagaa ctccctgtat    240

ctgcgaatga acagtctgag agctgatgac acggccttgt attattgtgt aaaagaaggg    300

gtatggttcg ggaagttatt ctcatcctac ggtctggacg tctggggcca agggaccacg    360

gtcaccgtct cctca                                                     375
```

<210> SEQ ID NO 312
<211> LENGTH: 125
<212> TYPE: PRT
<213> ORGANISM: Artificial Sequence
<220> FEATURE:
<223> OTHER INFORMATION: Synthetic

<400> SEQUENCE: 312

```
Gln Val Gln Leu Val Gln Ser Gly Gly Gly Leu Val Gln Pro Gly Arg
 1               5                  10                  15

Ser Leu Lys Leu Ser Cys Ala Ala Ser Arg Phe Thr Phe Glu Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Arg Met Asn Ser Leu Arg Ala Asp Asp Thr Ala Leu Tyr Tyr Cys
                85                  90                  95

Val Lys Glu Gly Val Trp Phe Gly Lys Leu Phe Ser Ser Tyr Gly Leu
```

```
            100                 105                 110

Asp Val Trp Gly Gln Gly Thr Thr Val Thr Val Ser Ser
        115                 120                 125


<210> SEQ ID NO 313
<211> LENGTH: 24
<212> TYPE: DNA
<213> ORGANISM: Artificial Sequence
<220> FEATURE:
<223> OTHER INFORMATION: Synthetic

<400> SEQUENCE: 313

agattcacct ttgaagatta tgcc                                            24


<210> SEQ ID NO 314
<211> LENGTH: 8
<212> TYPE: PRT
<213> ORGANISM: Artificial Sequence
<220> FEATURE:
<223> OTHER INFORMATION: Synthetic

<400> SEQUENCE: 314

Arg Phe Thr Phe Glu Asp Tyr Ala
 1               5


<210> SEQ ID NO 315
<211> LENGTH: 24
<212> TYPE: DNA
<213> ORGANISM: Artificial Sequence
<220> FEATURE:
<223> OTHER INFORMATION: Synthetic

<400> SEQUENCE: 315

attagttgga atagtggtag tata                                            24


<210> SEQ ID NO 316
<211> LENGTH: 8
<212> TYPE: PRT
<213> ORGANISM: Artificial Sequence
<220> FEATURE:
<223> OTHER INFORMATION: Synthetic

<400> SEQUENCE: 316

Ile Ser Trp Asn Ser Gly Ser Ile
 1               5


<210> SEQ ID NO 317
<211> LENGTH: 54
<212> TYPE: DNA
<213> ORGANISM: Artificial Sequence
<220> FEATURE:
<223> OTHER INFORMATION: Synthetic

<400> SEQUENCE: 317

gtaaaagaag ggtatggtt cgggaagtta ttctcatcct acggtctgga cgtc            54


<210> SEQ ID NO 318
<211> LENGTH: 16
<212> TYPE: PRT
<213> ORGANISM: Artificial Sequence
<220> FEATURE:
<223> OTHER INFORMATION: Synthetic

<400> SEQUENCE: 318

Glu Gly Val Trp Phe Gly Lys Leu Phe Ser Ser Tyr Gly Leu Asp Val
 1               5                  10                  15
```

<210> SEQ ID NO 319
<211> LENGTH: 321
<212> TYPE: DNA
<213> ORGANISM: Artificial Sequence
<220> FEATURE:
<223> OTHER INFORMATION: Synthetic

<400> SEQUENCE: 319
gccatccagt tgacccagtc tccagccacc ctgtctgtgt ctccagggga aagagccacc 60
ctctcttgca gggccagtca gagtgttagc agcaacttag cctggtacca gcagaaacct 120
gaccaggctc ccaggctcct catctatggt tcatccacca gggccactgg tatcccagcc 180
aggttcagtg gcagtgggtc tgggacagag ttcactctca ccatcagcag cctgcagtct 240
gaagattttg cagtttatta ctgtcagcag tataataact ggccgtacac ttttggccag 300
gggaccaagg tggagatcaa a 321

<210> SEQ ID NO 320
<211> LENGTH: 107
<212> TYPE: PRT
<213> ORGANISM: Artificial Sequence
<220> FEATURE:
<223> OTHER INFORMATION: Synthetic

<400> SEQUENCE: 320

Ala Ile Gln Leu Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Asp Gln Ala Pro Arg Leu Leu Ile
35 40 45

Tyr Gly Ser Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Tyr
85 90 95

Thr Phe Gly Gln Gly Thr Lys Val Glu Ile Lys
100 105

<210> SEQ ID NO 321
<211> LENGTH: 18
<212> TYPE: DNA
<213> ORGANISM: Artificial Sequence
<220> FEATURE:
<223> OTHER INFORMATION: Synthetic

<400> SEQUENCE: 321
cagagtgtta gcagcaac 18

<210> SEQ ID NO 322
<211> LENGTH: 6
<212> TYPE: PRT
<213> ORGANISM: Artificial Sequence
<220> FEATURE:
<223> OTHER INFORMATION: Synthetic

<400> SEQUENCE: 322

Gln Ser Val Ser Ser Asn
1 5

<210> SEQ ID NO 323

<211> LENGTH: 9
<212> TYPE: DNA
<213> ORGANISM: Artificial Sequence
<220> FEATURE:
<223> OTHER INFORMATION: Synthetic

<400> SEQUENCE: 323 ggttcatcc 9

<210> SEQ ID NO 324
<211> LENGTH: 3
<212> TYPE: PRT
<213> ORGANISM: Artificial Sequence
<220> FEATURE:
<223> OTHER INFORMATION: Synthetic

<400> SEQUENCE: 324

Gly Ser Ser
1

<210> SEQ ID NO 325
<211> LENGTH: 27
<212> TYPE: DNA
<213> ORGANISM: Artificial Sequence
<220> FEATURE:
<223> OTHER INFORMATION: Synthetic

<400> SEQUENCE: 325
cagcagtata ataactggcc gtacact 27

<210> SEQ ID NO 326
<211> LENGTH: 9
<212> TYPE: PRT
<213> ORGANISM: Artificial Sequence
<220> FEATURE:
<223> OTHER INFORMATION: Synthetic

<400> SEQUENCE: 326

Gln Gln Tyr Asn Asn Trp Pro Tyr Thr
1 5

<210> SEQ ID NO 327
<211> LENGTH: 375
<212> TYPE: DNA
<213> ORGANISM: Artificial Sequence
<220> FEATURE:
<223> OTHER INFORMATION: Synthetic

<400> SEQUENCE: 327
gaggtgcagc tggtggagtc cggcggcggc ctggtgcagc ccggccggtc cctgcggctg 60
tcctgcgccg cctcccggtt caccttcgag gactacgcca tgcactgggt gcggcaggcc 120
cccggcaagg gcctggagtg ggtgtccggc atctcctgga actccggctc catcggctac 180
gccgactccg tgaagggccg gttcaccatc tcccgggaca acgccaagaa ctccctgtac 240
ctgcagatga actccctgcg ggccgaggac accgccctgt actactgcgt gaaggagggc 300
gtgtggttcg gcaagctgtt ctcctcctac ggcctggacg tgtggggcca gggcaccacc 360
gtgaccgtgt cctcc 375

<210> SEQ ID NO 328
<211> LENGTH: 125
<212> TYPE: PRT
<213> ORGANISM: Artificial Sequence
<220> FEATURE:
<223> OTHER INFORMATION: Synthetic

<400> SEQUENCE: 328

```
Glu Val Gln Leu Val Glu Ser Gly Gly Gly Leu Val Gln Pro Gly Arg
 1               5                  10                  15

Ser Leu Arg Leu Ser Cys Ala Ala Ser Arg Phe Thr Phe Glu Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Glu Gly Val Trp Phe Gly Lys Leu Phe Ser Ser Tyr Gly Leu
            100                 105                 110

Asp Val Trp Gly Gln Gly Thr Thr Val Thr Val Ser Ser
        115                 120                 125
```

<210> SEQ ID NO 329
<211> LENGTH: 321
<212> TYPE: DNA
<213> ORGANISM: Artificial Sequence
<220> FEATURE:
<223> OTHER INFORMATION: Synthetic

<400> SEQUENCE: 329

```
gagatcgtga tgacccagtc ccccgccacc ctgtccgtgt cccccggcga gcgggccacc      60

ctgtcctgcc gggcctccca gtccgtgtcc tccaacctgg cctggtacca gcagaagccc     120

ggccaggccc cccggctgct gatctacggc tcctccaccc gggccaccgg catccccgcc     180

cggttctccg gctccggctc cggcaccgag ttcaccctga ccatctcctc cctgcagtcc     240

gaggacttcg ccgtgtacta ctgccagcag tacaacaact ggccctacac cttcggccag     300

ggcaccaagc tggagatcaa g                                                321
```

<210> SEQ ID NO 330
<211> LENGTH: 107
<212> TYPE: PRT
<213> ORGANISM: Artificial Sequence
<220> FEATURE:
<223> OTHER INFORMATION: Synthetic

<400> SEQUENCE: 330

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ser Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys
            100                 105
```

<210> SEQ ID NO 331
<211> LENGTH: 375
<212> TYPE: DNA
<213> ORGANISM: Artificial Sequence
<220> FEATURE:
<223> OTHER INFORMATION: Synthetic

<400> SEQUENCE: 331

```
gaggtgcagc tggtggagtc tgggggaggc ttggtacagc ctggcaggtc cctgaaactc     60

tcctgtgcag cctctagatt cacctttgaa gattatgcca tgcactgggt ccggcaagct    120

ccagggaagg gcctggaatg ggtctcaggg attagttgga atagtggtag tataggttat    180

gcggactctg tgaagggccg attcaccatc tccagagaca acgccaagaa ctccctgtat    240

ctgcgaatga acagtctgag agctgatgac acggccttgt attattgtgt aaaagaaggg    300

gtatggttcg ggaagttatt ctcatcctac ggtctggacg tctggggcca agggaccacg    360

gtcaccgtct cctca                                                     375
```

<210> SEQ ID NO 332
<211> LENGTH: 125
<212> TYPE: PRT
<213> ORGANISM: Artificial Sequence
<220> FEATURE:
<223> OTHER INFORMATION: Synthetic

<400> SEQUENCE: 332

```
Glu Val Gln Leu Val Glu Ser Gly Gly Gly Leu Val Gln Pro Gly Arg
 1               5                  10                  15

Ser Leu Lys Leu Ser Cys Ala Ala Ser Arg Phe Thr Phe Glu Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Arg Met Asn Ser Leu Arg Ala Asp Asp Thr Ala Leu Tyr Tyr Cys
                85                  90                  95

Val Lys Glu Gly Val Trp Phe Gly Lys Leu Phe Ser Ser Tyr Gly Leu
            100                 105                 110

Asp Val Trp Gly Gln Gly Thr Thr Val Thr Val Ser Ser
        115                 120                 125
```

<210> SEQ ID NO 333
<211> LENGTH: 321
<212> TYPE: DNA
<213> ORGANISM: Artificial Sequence
<220> FEATURE:
<223> OTHER INFORMATION: Synthetic

<400> SEQUENCE: 333

```
gaaatagtga tgacgcagtc tccagccacc ctgtctgtgt ctccagggga aagagccacc     60

ctctcttgca gggccagtca gagtgttagc agcaacttag cctggtacca gcagaaacct    120

gaccaggctc ccaggctcct catctatggt tcatccacca gggccactgg tatcccagcc    180

aggttcagtg gcagtgggtc tgggacagag ttcactctca ccatcagcag cctgcagtct    240

gaagattttg cagtttatta ctgtcagcag tataataact ggccgtacac ttttggccag    300

gggaccaagc tggagatcaa a                                              321
```

<210> SEQ ID NO 334
<211> LENGTH: 107
<212> TYPE: PRT
<213> ORGANISM: Artificial Sequence
<220> FEATURE:
<223> OTHER INFORMATION: Synthetic

<400> SEQUENCE: 334

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Asp Gln Ala Pro Arg Leu Leu Ile
35 40 45

Tyr Gly Ser Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Tyr
85 90 95

Thr Phe Gly Gln Gly Thr Lys Leu Glu Ile Lys
100 105

<210> SEQ ID NO 335
<211> LENGTH: 375
<212> TYPE: DNA
<213> ORGANISM: Artificial Sequence
<220> FEATURE:
<223> OTHER INFORMATION: Synthetic

<400> SEQUENCE: 335
gaagtgcagc tggtgcagtc tgggggcggc ttggtacagc ctggcaggtc cctgagactc 60
tcctgtgcag cccctggatt caactttgat gattatgcca tgcactgggt ccggcaagct 120
ccagggaagg gcctggagtg ggtctcaggt attagttgga atagtggtag tataggctat 180
gcggactctg tgaagggccg attcaccatc tccagagaca acgccaagaa ctccctgtat 240
ctgcaaatga acagtctgag agctgaggac acggccttgt attactgtgc aaaagaaggg 300
gtatggttcg gaaaattatt ctcatcctac ggtatggacg tctggggcca agggaccacg 360
gtcaccgtct cctca 375

<210> SEQ ID NO 336
<211> LENGTH: 125
<212> TYPE: PRT
<213> ORGANISM: Artificial Sequence
<220> FEATURE:
<223> OTHER INFORMATION: Synthetic

<400> SEQUENCE: 336

Glu Val Gln Leu Val Gln Ser Gly Gly Gly Leu Val Gln Pro Gly Arg
1 5 10 15

Ser Leu Arg Leu Ser Cys Ala Ala Pro Gly Phe Asn Phe Asp Asp Tyr
20 25 30

Ala Met His Trp Val Arg Gln Ala Pro Gly Lys Gly Leu Glu Trp Val
35 40 45

Ser Gly Ile Ser Trp Asn Ser Gly Ser Ile Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys

```
                85                  90                  95

Ala Lys Glu Gly Val Trp Phe Gly Lys Leu Phe Ser Ser Tyr Gly Met
            100                 105                 110

Asp Val Trp Gly Gln Gly Thr Thr Val Thr Val Ser Ser
        115                 120                 125


<210> SEQ ID NO 337
<211> LENGTH: 24
<212> TYPE: DNA
<213> ORGANISM: Artificial Sequence
<220> FEATURE:
<223> OTHER INFORMATION: Synthetic

<400> SEQUENCE: 337

ggattcaact ttgatgatta tgcc                                            24


<210> SEQ ID NO 338
<211> LENGTH: 8
<212> TYPE: PRT
<213> ORGANISM: Artificial Sequence
<220> FEATURE:
<223> OTHER INFORMATION: Synthetic

<400> SEQUENCE: 338

Gly Phe Asn Phe Asp Asp Tyr Ala
 1               5


<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339

attagttgga atagtggtag tata                                            24


<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

Ile Ser Trp Asn Ser Gly Ser Ile
 1               5


<210> SEQ ID NO 341
<211> LENGTH: 54
<212> TYPE: DNA
<213> ORGANISM: Artificial Sequence
<220> FEATURE:
<223> OTHER INFORMATION: Synthetic

<400> SEQUENCE: 341

gcaaaagaag ggtatggtt cggaaaatta ttctcatcct acggtatgga cgtc           54


<210> SEQ ID NO 342
<211> LENGTH: 18
<212> TYPE: PRT
<213> ORGANISM: Artificial Sequence
<220> FEATURE:
<223> OTHER INFORMATION: Synthetic

<400> SEQUENCE: 342
```

```
Ala Lys Glu Gly Val Trp Phe Gly Lys Leu Phe Ser Ser Tyr Gly Met
 1               5                  10                  15

Asp Val


<210> SEQ ID NO 343
<211> LENGTH: 321
<212> TYPE: DNA
<213> ORGANISM: Artificial Sequence
<220> FEATURE:
<223> OTHER INFORMATION: Synthetic

<400> SEQUENCE: 343

gatgttgtga tgacccagtc tccagccacc ctgtctgtgt ctccagggga aagagccacc     60

ctctcctgca gggccagtca gagtgttagc agcaacttag actggtacca gcagaaacct    120

ggccaggctc ccaggctcct catctatggt gcatccacca gggccactgg tatcccagcc    180

aggttcagtg gcagtgggtc tgggacagag ttcactctca ccatcagcag cctgcagtct    240

gaagattttg cagtttatta ctgtcagcag tataataact ggccgtacac ttttggccag    300

gggaccaagc tggagatcaa a                                              321


<210> SEQ ID NO 344
<211> LENGTH: 107
<212> TYPE: PRT
<213> ORGANISM: Artificial Sequence
<220> FEATURE:
<223> OTHER INFORMATION: Synthetic

<400> SEQUENCE: 344

Asp Val Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Asp Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys
            100                 105


<210> SEQ ID NO 345
<211> LENGTH: 18
<212> TYPE: DNA
<213> ORGANISM: Artificial Sequence
<220> FEATURE:
<223> OTHER INFORMATION: Synthetic

<400> SEQUENCE: 345

cagagtgtta gcagcaac                                                   18


<210> SEQ ID NO 346
<211> LENGTH: 7
<212> TYPE: PRT
<213> ORGANISM: Artificial Sequence
<220> FEATURE:
<223> OTHER INFORMATION: Synthetic

<400> SEQUENCE: 346
```

Ser Gln Ser Val Ser Ser Asn
 1               5

<210> SEQ ID NO 347
<211> LENGTH: 9
<212> TYPE: DNA
<213> ORGANISM: Artificial Sequence
<220> FEATURE:
<223> OTHER INFORMATION: Synthetic

<400> SEQUENCE: 347 ggtgcatcc 9

<210> SEQ ID NO 348
<211> LENGTH: 3
<212> TYPE: PRT
<213> ORGANISM: Artificial Sequence
<220> FEATURE:
<223> OTHER INFORMATION: Synthetic

<400> SEQUENCE: 348

Gly Ala Ser
 1

<210> SEQ ID NO 349
<211> LENGTH: 27
<212> TYPE: DNA
<213> ORGANISM: Artificial Sequence
<220> FEATURE:
<223> OTHER INFORMATION: Synthetic

<400> SEQUENCE: 349
cagcagtata ataactggcc gtacact 27

<210> SEQ ID NO 350
<211> LENGTH: 9
<212> TYPE: PRT
<213> ORGANISM: Artificial Sequence
<220> FEATURE:
<223> OTHER INFORMATION: Synthetic

<400> SEQUENCE: 350

Gln Gln Tyr Asn Asn Trp Pro Tyr Thr
 1               5

<210> SEQ ID NO 351
<211> LENGTH: 375
<212> TYPE: DNA
<213> ORGANISM: Artificial Sequence
<220> FEATURE:
<223> OTHER INFORMATION: Synthetic

<400> SEQUENCE: 351
gaggtgcagc tggtggagtc cggcggcggc ctggtgcagc ccggccggtc cctgcggctg 60
tcctgcgccg cctccggctt caacttcgac gactacgcca tgcactgggt gcggcaggcc 120
cccggcaagg gcctggagtg ggtgtccggc atctcctgga actccggctc catcggctac 180
gccgactccg tgaagggccg gttcaccatc tcccgggaca acgccaagaa ctccctgtac 240
ctgcagatga actccctgcg ggccgaggac accgccctgt actactgcgc caaggagggc 300
gtgtggttcg gcaagctgtt ctcctcctac ggcatggacg tgtggggcca gggcaccacc 360
gtgaccgtgt cctcc 375

<210> SEQ ID NO 352
<211> LENGTH: 125

<212> TYPE: PRT
<213> ORGANISM: Artificial Sequence
<220> FEATURE:
<223> OTHER INFORMATION: Synthetic

<400> SEQUENCE: 352

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Asn Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Val Trp Phe Gly Lys Leu Phe Ser Ser Tyr Gly Met
            100                 105                 110

Asp Val Trp Gly Gln Gly Thr Thr Val Thr Val Ser Ser
        115                 120                 125
```

<210> SEQ ID NO 353
<211> LENGTH: 321
<212> TYPE: DNA
<213> ORGANISM: Artificial Sequence
<220> FEATURE:
<223> OTHER INFORMATION: Synthetic

<400> SEQUENCE: 353

```
gagatcgtga tgacccagtc ccccgccacc ctgtccgtgt cccccggcga gcgggccacc     60

ctgtcctgcc gggcctccca gtccgtgtcc tccaacctgg cctggtacca gcagaagccc    120

ggccaggccc cccggctgct gatctacggc gcctccaccc gggccaccgg catccccgcc    180

cggttctccg gctccggctc cggcaccgag ttcaccctga ccatctcctc cctgcagtcc    240

gaggacttcg ccgtgtacta ctgccagcag tacaacaact ggccctacac cttcggccag    300

ggcaccaagc tggagatcaa g                                              321
```

<210> SEQ ID NO 354
<211> LENGTH: 107
<212> TYPE: PRT
<213> ORGANISM: Artificial Sequence
<220> FEATURE:
<223> OTHER INFORMATION: Synthetic

<400> SEQUENCE: 354

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Tyr
                85                  90                  95
```

```
Thr Phe Gly Gln Gly Thr Lys Leu Glu Ile Lys
            100                 105


<210> SEQ ID NO 355
<211> LENGTH: 375
<212> TYPE: DNA
<213> ORGANISM: Artificial Sequence
<220> FEATURE:
<223> OTHER INFORMATION: Synthetic

<400> SEQUENCE: 355

gaggtgcagc tggtggagtc tgggggcggc ttggtacagc ctggcaggtc cctgagactc      60

tcctgtgcag cccctggatt caactttgat gattatgcca tgcactgggt ccggcaagct     120

ccagggaagg gcctggagtg ggtctcaggt attagttgga atagtggtag tataggctat     180

gcggactctg tgaagggccg attcaccatc tccagagaca acgccaagaa ctccctgtat     240

ctgcaaatga acagtctgag agctgaggac acggccttgt attactgtgc aaaagaaggg     300

gtatggttcg gaaaattatt ctcatcctac ggtatggacg tctggggcca agggaccacg     360

gtcaccgtct cctca                                                      375


<210> SEQ ID NO 356
<211> LENGTH: 125
<212> TYPE: PRT
<213> ORGANISM: Artificial Sequence
<220> FEATURE:
<223> OTHER INFORMATION: Synthetic

<400> SEQUENCE: 356

Glu Val Gln Leu Val Glu Ser Gly Gly Gly Leu Val Gln Pro Gly Arg
 1               5                  10                  15

Ser Leu Arg Leu Ser Cys Ala Ala Pro Gly Phe Asn Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Val Trp Phe Gly Lys Leu Phe Ser Ser Tyr Gly Met
            100                 105                 110

Asp Val Trp Gly Gln Gly Thr Thr Val Thr Val Ser Ser
        115                 120                 125


<210> SEQ ID NO 357
<211> LENGTH: 320
<212> TYPE: DNA
<213> ORGANISM: Artificial Sequence
<220> FEATURE:
<223> OTHER INFORMATION: Synthetic

<400> SEQUENCE: 357

gaaatagtga tgacgcagtc tccagccacc ctgtctgtgt ctccagggga aagagccacc      60

ctctcctgca gggccagtca gagtgttagc agcaacttag actggtacca gcagaaacct     120

ggccaggctc ccaggctcct catctatggt gcatccacca gggccactgg tatcccagcc     180

aggttcagtg gcagtgggtc tgggacagag ttcactctca ccatcagcag cctgcagtct     240
```

```
gaagattttg cagtttatta ctgtcagcag tataataact ggccgtacac ttttggccag    300

ggaccaagct ggagatcaaa                                                320


<210> SEQ ID NO 358
<211> LENGTH: 107
<212> TYPE: PRT
<213> ORGANISM: Artificial Sequence
<220> FEATURE:
<223> OTHER INFORMATION: Synthetic

<400> SEQUENCE: 358

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Asp Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys
            100                 105


<210> SEQ ID NO 359
<211> LENGTH: 375
<212> TYPE: DNA
<213> ORGANISM: Artificial Sequence
<220> FEATURE:
<223> OTHER INFORMATION: Synthetic

<400> SEQUENCE: 359

gaggtgcagc tggtgcagtc tgggggaggc ttggtacagc ctggcaggtc cctgagactc     60

tcctgtgcag cctctggatt cacctttgat gattatgcca tgcactgggt ccggcaaggt    120

ccagggaagg gcctggagtg ggtctcaggt attagttgga atagtggtag tataggctat    180

gcggactctg tgaagggccg attcaccatc tccagagaca acgccaagaa ctccctgtat    240

ctgcaaatga acagtctgag agctgaggac acggccttgt attactgtgc aaaagaaggg    300

gtatggttcg gggagttatt ttcatcctac ggtatggacg tctggggcca agggaccctg    360

gtcaccgtct cctca                                                     375


<210> SEQ ID NO 360
<211> LENGTH: 125
<212> TYPE: PRT
<213> ORGANISM: Artificial Sequence
<220> FEATURE:
<223> OTHER INFORMATION: Synthetic

<400> SEQUENCE: 360

Glu Val Gln Leu Val Gln Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Gly Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60
```

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Val Trp Phe Gly Glu Leu Phe Ser Ser Tyr Gly Met
            100                 105                 110

Asp Val Trp Gly Gln Gly Thr Leu Val Thr Val Ser Ser
        115                 120                 125
```

<210> SEQ ID NO 361
<211> LENGTH: 24
<212> TYPE: DNA
<213> ORGANISM: Artificial Sequence
<220> FEATURE:
<223> OTHER INFORMATION: Synthetic

<400> SEQUENCE: 361
ggattcacct ttgatgatta tgcc 24

<210> SEQ ID NO 362
<211> LENGTH: 8
<212> TYPE: PRT
<213> ORGANISM: Artificial Sequence
<220> FEATURE:
<223> OTHER INFORMATION: Synthetic

<400> SEQUENCE: 362

```
Gly Phe Thr Phe Asp Asp Tyr Ala
 1               5
```

<210> SEQ ID NO 363
<211> LENGTH: 24
<212> TYPE: DNA
<213> ORGANISM: Artificial Sequence
<220> FEATURE:
<223> OTHER INFORMATION: Synthetic

<400> SEQUENCE: 363
attagttgga atagtggtag tata 24

<210> SEQ ID NO 364
<211> LENGTH: 8
<212> TYPE: PRT
<213> ORGANISM: Artificial Sequence
<220> FEATURE:
<223> OTHER INFORMATION: Synthetic

<400> SEQUENCE: 364

```
Ile Ser Trp Asn Ser Gly Ser Ile
 1               5
```

<210> SEQ ID NO 365
<211> LENGTH: 54
<212> TYPE: DNA
<213> ORGANISM: Artificial Sequence
<220> FEATURE:
<223> OTHER INFORMATION: Synthetic

<400> SEQUENCE: 365
gcaaaagaag ggtatggtt cggggagtta ttttcatcct acggtatgga cgtc 54

<210> SEQ ID NO 366
<211> LENGTH: 18
<212> TYPE: PRT
<213> ORGANISM: Artificial Sequence
<220> FEATURE:
<223> OTHER INFORMATION: Synthetic

<400> SEQUENCE: 366

```
Ala Lys Glu Gly Val Trp Phe Gly Glu Leu Phe Ser Ser Tyr Gly Met
 1               5                  10                  15

Asp Val
```

<210> SEQ ID NO 367
<211> LENGTH: 321
<212> TYPE: DNA
<213> ORGANISM: Artificial Sequence
<220> FEATURE:
<223> OTHER INFORMATION: Synthetic

<400> SEQUENCE: 367

```
gaaattgtgc tgactcagtc tccagccacc ctgtctgtgt ctccagggga aagagccacc     60

ctctcctgca gggccagtcc gagtgttagc agcaacttag cctggtacca gcagaaacct    120

ggccagcctc ccaggctcct catctatggt gcatccacca gggccactgg tatcccagcc    180

aggttcagtg gcagtgggtc tgggacagag ttcactctca ccatcagcag cctgcagtct    240

gaagattttg cagtttatta ctgtcagcag tatagtaact ggccgtacac ttttggccag    300

gggaccaagc tggagatcaa a                                              321
```

<210> SEQ ID NO 368
<211> LENGTH: 107
<212> TYPE: PRT
<213> ORGANISM: Artificial Sequence
<220> FEATURE:
<223> OTHER INFORMATION: Synthetic

<400> SEQUENCE: 368

```
Glu Ile Val Leu Thr Gln Ser Pro Ala Thr Leu Ser Val Ser Pro Gly
 1               5                  10                  15

Glu Arg Ala Thr Leu Ser Cys Arg Ala Ser Pro Ser Val Ser Ser Asn
            20                  25                  30

Leu Ala Trp Tyr Gln Gln Lys Pro Gly Gln Pro Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Asn Trp Pro Tyr
                85                  90                  95

Thr Phe Gly Gln Gly Thr Lys Leu Glu Ile Lys
            100                 105
```

<210> SEQ ID NO 369
<211> LENGTH: 18
<212> TYPE: DNA
<213> ORGANISM: Artificial Sequence
<220> FEATURE:
<223> OTHER INFORMATION: Synthetic

<400> SEQUENCE: 369

```
ccgagtgtta gcagcaac                                                   18
```

<210> SEQ ID NO 370
<211> LENGTH: 6
<212> TYPE: PRT
<213> ORGANISM: Artificial Sequence
<220> FEATURE:
<223> OTHER INFORMATION: Synthetic

<400> SEQUENCE: 370

Pro Ser Val Ser Ser Asn
1 5

<210> SEQ ID NO 371
<211> LENGTH: 9
<212> TYPE: DNA
<213> ORGANISM: Artificial Sequence
<220> FEATURE:
<223> OTHER INFORMATION: Synthetic

<400> SEQUENCE: 371 ggtgcatcc 9

<210> SEQ ID NO 372
<211> LENGTH: 3
<212> TYPE: PRT
<213> ORGANISM: Artificial Sequence
<220> FEATURE:
<223> OTHER INFORMATION: Synthetic

<400> SEQUENCE: 372

Gly Ala Ser
1

<210> SEQ ID NO 373
<211> LENGTH: 27
<212> TYPE: DNA
<213> ORGANISM: Artificial Sequence
<220> FEATURE:
<223> OTHER INFORMATION: Synthetic

<400> SEQUENCE: 373
cagcagtata gtaactggcc gtacact 27

<210> SEQ ID NO 374
<211> LENGTH: 9
<212> TYPE: PRT
<213> ORGANISM: Artificial Sequence
<220> FEATURE:
<223> OTHER INFORMATION: Synthetic

<400> SEQUENCE: 374

Gln Gln Tyr Ser Asn Trp Pro Tyr Thr
1 5

<210> SEQ ID NO 375
<211> LENGTH: 375
<212> TYPE: DNA
<213> ORGANISM: Artificial Sequence
<220> FEATURE:
<223> OTHER INFORMATION: Synthetic

<400> SEQUENCE: 375
gaggtgcagc tggtggagtc cggcggcggc ctggtgcagc ccggccggtc cctgcggctg 60
tcctgcgccg cctccggctt caccttcgac gactacgcca tgcactgggt gcggcaggcc 120
cccggcaagg gcctggagtg ggtgtccggc atctcctgga actccggctc catcggctac 180
gccgactccg tgaagggccg gttcaccatc tcccgggaca acgccaagaa ctccctgtac 240
ctgcagatga actccctgcg ggccgaggac accgccctgt actactgcgc caaggagggc 300
gtgtggttcg gcgagctgtt ctcctcctac ggcatggacg tgtggggcca gggcaccacc 360

```
gtgaccgtgt cctcc                                                  375


<210> SEQ ID NO 376
<211> LENGTH: 125
<212> TYPE: PRT
<213> ORGANISM: Artificial Sequence
<220> FEATURE:
<223> OTHER INFORMATION: Synthetic

<400> SEQUENCE: 376

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Val Trp Phe Gly Glu Leu Phe Ser Ser Tyr Gly Met
            100                 105                 110

Asp Val Trp Gly Gln Gly Thr Thr Val Thr Val Ser Ser
        115                 120                 125


<210> SEQ ID NO 377
<211> LENGTH: 321
<212> TYPE: DNA
<213> ORGANISM: Artificial Sequence
<220> FEATURE:
<223> OTHER INFORMATION: Synthetic

<400> SEQUENCE: 377

gagatcgtga tgacccagtc ccccgccacc ctgtccgtgt cccccggcga gcgggccacc     60

ctgtcctgcc gggcctcccc ctccgtgtcc tccaacctgg cctggtacca gcagaagccc    120

ggccaggccc cccggctgct gatctacggc gcctccaccc gggccaccgg catccccgcc    180

cggttctccg gctccggctc cggcaccgag ttcaccctga ccatctcctc cctgcagtcc    240

gaggacttcg ccgtgtacta ctgccagcag tactccaact ggccctacac cttcggccag    300

ggcaccaagc tggagatcaa g                                              321


<210> SEQ ID NO 378
<211> LENGTH: 107
<212> TYPE: PRT
<213> ORGANISM: Artificial Sequence
<220> FEATURE:
<223> OTHER INFORMATION: Synthetic

<400> SEQUENCE: 378

Glu Ile Val Met Thr Gln Ser Pro Ala Thr Leu Ser Val Ser Pro Gly
 1               5                  10                  15

Glu Arg Ala Thr Leu Ser Cys Arg Ala Ser Pro Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60
```

```
Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Asn Trp Pro Tyr
                85                  90                  95

Thr Phe Gly Gln Gly Thr Lys Leu Glu Ile Lys
            100                 105


<210> SEQ ID NO 379
<211> LENGTH: 375
<212> TYPE: DNA
<213> ORGANISM: Artificial Sequence
<220> FEATURE:
<223> OTHER INFORMATION: Synthetic

<400> SEQUENCE: 379

gaggtgcagc tggtggagtc tgggggaggc ttggtacagc ctggcaggtc cctgagactc      60

tcctgtgcag cctctggatt cacctttgat gattatgcca tgcactgggt ccggcaaggt     120

ccagggaagg gcctggagtg ggtctcaggt attagttgga atagtggtag tataggctat     180

gcggactctg tgaagggccg attcaccatc tccagagaca acgccaagaa ctccctgtat     240

ctgcaaatga acagtctgag agctgaggac acggccttgt attactgtgc aaaagaaggg     300

gtatggttcg ggagttatt ttcatcctac ggtatggacg tctggggcca agggaccacg     360

gtcaccgtct cctca                                                      375


<210> SEQ ID NO 380
<211> LENGTH: 125
<212> TYPE: PRT
<213> ORGANISM: Artificial Sequence
<220> FEATURE:
<223> OTHER INFORMATION: Synthetic

<400> SEQUENCE: 380

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Gly Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Val Trp Phe Gly Glu Leu Phe Ser Ser Tyr Gly Met
            100                 105                 110

Asp Val Trp Gly Gln Gly Thr Thr Val Thr Val Ser Ser
        115                 120                 125


<210> SEQ ID NO 381
<211> LENGTH: 321
<212> TYPE: DNA
<213> ORGANISM: Artificial Sequence
<220> FEATURE:
<223> OTHER INFORMATION: Synthetic

<400> SEQUENCE: 381

gaaatagtga tgacgcagtc tccagccacc ctgtctgtgt ctccagggga aagagccacc      60

ctctcctgca gggccagtcc gagtgttagc agcaacttag cctggtacca gcagaaacct     120
```

```
ggccagcctc ccaggctcct catctatggt gcatccacca gggccactgg tatcccagcc    180

aggttcagtg gcagtgggtc tgggacagag ttcactctca ccatcagcag cctgcagtct    240

gaagattttg cagtttatta ctgtcagcag tatagtaact ggccgtacac ttttggccag    300

gggaccaagc tggagatcaa a                                               321
```

```
<210> SEQ ID NO 382
<211> LENGTH: 107
<212> TYPE: PRT
<213> ORGANISM: Artificial Sequence
<220> FEATURE:
<223> OTHER INFORMATION: Synthetic

<400> SEQUENCE: 382

Glu Ile Val Met Thr Gln Ser Pro Ala Thr Leu Ser Val Ser Pro Gly
1               5                   10                  15

Glu Arg Ala Thr Leu Ser Cys Arg Ala Ser Pro Ser Val Ser Ser Asn
            20                  25                  30

Leu Ala Trp Tyr Gln Gln Lys Pro Gly Gln Pro Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Asn Trp Pro Tyr
                85                  90                  95

Thr Phe Gly Gln Gly Thr Lys Leu Glu Ile Lys
            100                 105
```

```
<210> SEQ ID NO 383
<211> LENGTH: 375
<212> TYPE: DNA
<213> ORGANISM: Artificial Sequence
<220> FEATURE:
<223> OTHER INFORMATION: Synthetic

<400> SEQUENCE: 383

caggtccagc tggtacagtc tgggggaggc ttggtacagc ctggcaggtc cctgagactc     60

tcctgtgcag cctctggatt cacctttgat gattatgcca tgcactgggt ccggcaaggt    120

ccagggaagg gcctggagtg ggtctcaggt attagttgga atagtggtag tataggctat    180

gcggactctg tgaagggccg attcaccatc tccagagaca acgccaagaa ctccctgtat    240

ctgcaaatga acagtctgag agctgaggac acggccttgt attactgtgc aaaagaaggg    300

gtatggttcg gggagttatt ttcatcctac ggtatggacg tctggggcca agggaccacg    360

gtcaccgtct cctca                                                      375
```

```
<210> SEQ ID NO 384
<211> LENGTH: 125
<212> TYPE: PRT
<213> ORGANISM: Artificial Sequence
<220> FEATURE:
<223> OTHER INFORMATION: Synthetic

<400> SEQUENCE: 384

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30
```

```
Ala Met His Trp Val Arg Gln Gly Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Val Trp Phe Gly Glu Leu Phe Ser Ser Tyr Gly Met
            100                 105                 110

Asp Val Trp Gly Gln Gly Thr Thr Val Thr Val Ser Ser
        115                 120                 125


<210> SEQ ID NO 385
<211> LENGTH: 24
<212> TYPE: DNA
<213> ORGANISM: Artificial Sequence
<220> FEATURE:
<223> OTHER INFORMATION: Synthetic

<400> SEQUENCE: 385

ggattcacct ttgatgatta tgcc                                              24


<210> SEQ ID NO 386
<211> LENGTH: 8
<212> TYPE: PRT
<213> ORGANISM: Artificial Sequence
<220> FEATURE:
<223> OTHER INFORMATION: Synthetic

<400> SEQUENCE: 386

Gly Phe Thr Phe Asp Asp Tyr Ala
 1               5


<210> SEQ ID NO 387
<211> LENGTH: 24
<212> TYPE: DNA
<213> ORGANISM: Artificial Sequence
<220> FEATURE:
<223> OTHER INFORMATION: Synthetic

<400> SEQUENCE: 387

attagttgga atagtggtag tata                                              24


<210> SEQ ID NO 388
<211> LENGTH: 8
<212> TYPE: PRT
<213> ORGANISM: Artificial Sequence
<220> FEATURE:
<223> OTHER INFORMATION: Synthetic

<400> SEQUENCE: 388

Ile Ser Trp Asn Ser Gly Ser Ile
 1               5


<210> SEQ ID NO 389
<211> LENGTH: 54
<212> TYPE: DNA
<213> ORGANISM: Artificial Sequence
<220> FEATURE:
<223> OTHER INFORMATION: Synthetic

<400> SEQUENCE: 389

gcaaaagaag ggtatggtt cggggagtta ttttcatcct acggtatgga cgtc              54
```

<210> SEQ ID NO 390
<211> LENGTH: 18
<212> TYPE: PRT
<213> ORGANISM: Artificial Sequence
<220> FEATURE:
<223> OTHER INFORMATION: Synthetic

<400> SEQUENCE: 390

```
Ala Lys Glu Gly Val Trp Phe Gly Glu Leu Phe Ser Ser Tyr Gly Met
 1               5                  10                  15

Asp Val
```

<210> SEQ ID NO 391
<211> LENGTH: 321
<212> TYPE: DNA
<213> ORGANISM: Artificial Sequence
<220> FEATURE:
<223> OTHER INFORMATION: Synthetic

<400> SEQUENCE: 391

```
gaaatagtga tgacgcagtc tccagccacc ctgtctgtgt ctccagggga aagagccacc     60

ctctcctgca gggccagtcc gagtgttagc agcaacttag cctggtacca gcagaaacct    120

ggccagcctc ccaggctcct catctatggt gcatccacca gggccactgg tatcccagcc    180

aggttcagtg gcagtgggtc tgggacagag ttcactctca ccatcagcag cctgcagtct    240

gaagattttg cagtttatta ctgtcagcag tatagtaact ggccgtacac ttttggccag    300

gggaccaagg tggagatcaa a                                              321
```

<210> SEQ ID NO 392
<211> LENGTH: 107
<212> TYPE: PRT
<213> ORGANISM: Artificial Sequence
<220> FEATURE:
<223> OTHER INFORMATION: Synthetic

<400> SEQUENCE: 392

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Pro Ser Val Ser Ser Asn
            20                  25                  30

Leu Ala Trp Tyr Gln Gln Lys Pro Gly Gln Pro Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Asn Trp Pro Tyr
                85                  90                  95

Thr Phe Gly Gln Gly Thr Lys Val Glu Ile Lys
            100                 105
```

<210> SEQ ID NO 393
<211> LENGTH: 18
<212> TYPE: DNA
<213> ORGANISM: Artificial Sequence
<220> FEATURE:
<223> OTHER INFORMATION: Synthetic

<400> SEQUENCE: 393

```
ccgagtgtta gcagcaac                                                   18
```

<210> SEQ ID NO 394
<211> LENGTH: 6
<212> TYPE: PRT
<213> ORGANISM: Artificial Sequence
<220> FEATURE:
<223> OTHER INFORMATION: Synthetic

<400> SEQUENCE: 394

Pro Ser Val Ser Ser Asn
1 5

<210> SEQ ID NO 395
<211> LENGTH: 9
<212> TYPE: DNA
<213> ORGANISM: Artificial Sequence
<220> FEATURE:
<223> OTHER INFORMATION: Synthetic

<400> SEQUENCE: 395 ggtgcatcc 9

<210> SEQ ID NO 396
<211> LENGTH: 3
<212> TYPE: PRT
<213> ORGANISM: Artificial Sequence
<220> FEATURE:
<223> OTHER INFORMATION: Synthetic

<400> SEQUENCE: 396

Gly Ala Ser
1

<210> SEQ ID NO 397
<211> LENGTH: 27
<212> TYPE: DNA
<213> ORGANISM: Artificial Sequence
<220> FEATURE:
<223> OTHER INFORMATION: Synthetic

<400> SEQUENCE: 397
cagcagtata gtaactggcc gtacact 27

<210> SEQ ID NO 398
<211> LENGTH: 9
<212> TYPE: PRT
<213> ORGANISM: Artificial Sequence
<220> FEATURE:
<223> OTHER INFORMATION: Synthetic

<400> SEQUENCE: 398

Gln Gln Tyr Ser Asn Trp Pro Tyr Thr
1 5

<210> SEQ ID NO 399
<211> LENGTH: 375
<212> TYPE: DNA
<213> ORGANISM: Artificial Sequence
<220> FEATURE:
<223> OTHER INFORMATION: Synthetic

<400> SEQUENCE: 399
gaggtgcagc tggtggagtc tgggggaggc ttggtacagc ctggcaggtc cctgagactc 60
tcctgtgcag cctctggatt cacctttgat gattatgcca tgcactgggt ccggcaaggt 120
ccagggaagg gcctggagtg ggtctcaggt attagttgga atagtggtag tataggctat 180
gcggactctg tgaagggccg attcaccatc tccagagaca acgccaagaa ctccctgtat 240

```
ctgcaaatga acagtctgag agctgaggac acggccttgt attactgtgc aaaagaaggg    300

gtatggttcg gggagttatt ttcatcctac ggtatggacg tctggggcca agggaccacg    360

gtcaccgtct cctca                                                     375


<210> SEQ ID NO 400
<211> LENGTH: 125
<212> TYPE: PRT
<213> ORGANISM: Artificial Sequence
<220> FEATURE:
<223> OTHER INFORMATION: Synthetic

<400> SEQUENCE: 400

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Gly Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Val Trp Phe Gly Glu Leu Phe Ser Ser Tyr Gly Met
            100                 105                 110

Asp Val Trp Gly Gln Gly Thr Thr Val Thr Val Ser Ser
        115                 120                 125


<210> SEQ ID NO 401
<211> LENGTH: 321
<212> TYPE: DNA
<213> ORGANISM: Artificial Sequence
<220> FEATURE:
<223> OTHER INFORMATION: Synthetic

<400> SEQUENCE: 401

gaaatagtga tgacgcagtc tccagccacc ctgtctgtgt ctccagggga aagagccacc     60

ctctcctgca gggccagtcc gagtgttagc agcaacttag cctggtacca gcagaaacct    120

ggccagcctc ccaggctcct catctatggt gcatccacca gggccactgg tatcccagcc    180

aggttcagtg gcagtgggtc tgggacagag ttcactctca ccatcagcag cctgcagtct    240

gaagattttg cagtttatta ctgtcagcag tatagtaact ggccgtacac ttttggccag    300

gggaccaagc tggagatcaa a                                              321


<210> SEQ ID NO 402
<211> LENGTH: 107
<212> TYPE: PRT
<213> ORGANISM: Artificial Sequence
<220> FEATURE:
<223> OTHER INFORMATION: Synthetic

<400> SEQUENCE: 402

Glu Ile Val Met Thr Gln Ser Pro Ala Thr Leu Ser Val Ser Pro Gly
1               5                   10                  15

Glu Arg Ala Thr Leu Ser Cys Arg Ala Ser Pro Ser Val Ser Ser Asn
            20                  25                  30

Leu Ala Trp Tyr Gln Gln Lys Pro Gly Gln Pro Pro Arg Leu Leu Ile
```

```
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Asn Trp Pro Tyr
                85                  90                  95

Thr Phe Gly Gln Gly Thr Lys Leu Glu Ile Lys
            100                 105


<210> SEQ ID NO 403
<211> LENGTH: 357
<212> TYPE: DNA
<213> ORGANISM: Artificial Sequence
<220> FEATURE:
<223> OTHER INFORMATION: Synthetic

<400> SEQUENCE: 403

gaggtgcagc tggtgcagtc tggggctgag gtgaagaagc ctggggcctc agtgaaggtc      60

tcctgcaagg tttccggatt cactctcact gaattatcca ttcactgggt gcgacaggct     120

cctggaaaag ggcttgagtg gatgggaggt tttgatcctg aagatggtga aacaatctcc     180

gcacagaagt tccagggcag agtcaccatg accgaggaca catctacaga cacagcctac     240

atggaactga gcagcctgag atctgaagac acggccatat attactgttc aacgattttt     300

ggagtggtta ccaactttga caactggggc cagggaacca cggtcaccgt ctcctca        357


<210> SEQ ID NO 404
<211> LENGTH: 119
<212> TYPE: PRT
<213> ORGANISM: Artificial Sequence
<220> FEATURE:
<223> OTHER INFORMATION: Synthetic

<400> SEQUENCE: 404

Glu Val Gln Leu Val Gln Ser Gly Ala Glu Val Lys Lys Pro Gly Ala
1               5                   10                  15

Ser Val Lys Val Ser Cys Lys Val Ser Gly Phe Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Ser Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Ile Tyr Tyr Cys
                85                  90                  95

Ser Thr Ile Phe Gly Val Val Thr Asn Phe Asp Asn Trp Gly Gln Gly
            100                 105                 110

Thr Thr Val Thr Val Ser Ser
        115


<210> SEQ ID NO 405
<211> LENGTH: 24
<212> TYPE: DNA
<213> ORGANISM: Artificial Sequence
<220> FEATURE:
<223> OTHER INFORMATION: Synthetic

<400> SEQUENCE: 405
```

ggattcactc tcactgaatt atcc 24

<210> SEQ ID NO 406
<211> LENGTH: 8
<212> TYPE: PRT
<213> ORGANISM: Artificial Sequence
<220> FEATURE:
<223> OTHER INFORMATION: Synthetic

<400> SEQUENCE: 406

Gly Phe Thr Leu Thr Glu Leu Ser
1 5

<210> SEQ ID NO 407
<211> LENGTH: 24
<212> TYPE: DNA
<213> ORGANISM: Artificial Sequence
<220> FEATURE:
<223> OTHER INFORMATION: Synthetic

<400> SEQUENCE: 407
tttgatcctg aagatggtga aaca 24

<210> SEQ ID NO 408
<211> LENGTH: 8
<212> TYPE: PRT
<213> ORGANISM: Artificial Sequence
<220> FEATURE:
<223> OTHER INFORMATION: Synthetic

<400> SEQUENCE: 408

Phe Asp Pro Glu Asp Gly Glu Thr
1 5

<210> SEQ ID NO 409
<211> LENGTH: 36
<212> TYPE: DNA
<213> ORGANISM: Artificial Sequence
<220> FEATURE:
<223> OTHER INFORMATION: Synthetic

<400> SEQUENCE: 409
tcaacgattt ttggagtggt taccaacttt gacaac 36

<210> SEQ ID NO 410
<211> LENGTH: 12
<212> TYPE: PRT
<213> ORGANISM: Artificial Sequence
<220> FEATURE:
<223> OTHER INFORMATION: Synthetic

<400> SEQUENCE: 410

Ser Thr Ile Phe Gly Val Val Thr Asn Phe Asp Asn
1 5 10

<210> SEQ ID NO 411
<211> LENGTH: 321
<212> TYPE: DNA
<213> ORGANISM: Artificial Sequence
<220> FEATURE:
<223> OTHER INFORMATION: Synthetic

<400> SEQUENCE: 411
gatattgtga tgacccagtc tccatcctcc ctgtctgcat ctgcaggaga cagagtcacc 60
atcacttgcc gggcaagtca ggccattaga aatgatttag gctggtatca gcagaaacca 120
gggaaagccc ctaagcgcct gatctatgct gcattcaatt tgcaaagtgg ggtcccatca 180

```
agattcagcg gcagtggatc tgggacagaa ttcactctca caatcagtag cctgcagcct    240

gaagatcttg caagttatta ctgtcaacag tataatagat acccgtggac gttcggccaa    300

gggaccaagc tggagatcaa a                                              321


<210> SEQ ID NO 412
<211> LENGTH: 107
<212> TYPE: PRT
<213> ORGANISM: Artificial Sequence
<220> FEATURE:
<223> OTHER INFORMATION: Synthetic

<400> SEQUENCE: 412

Asp Ile Val Met Thr Gln Ser Pro Ser Ser Leu Ser Ala Ser Ala Gly
 1               5                  10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Phe Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Leu Ala Ser Tyr Tyr Cys Gln Gln Tyr Asn Arg Tyr Pro Trp
                85                  90                  95

Thr Phe Gly Gln Gly Thr Lys Leu Glu Ile Lys
            100                 105


<210> SEQ ID NO 413
<211> LENGTH: 18
<212> TYPE: DNA
<213> ORGANISM: Artificial Sequence
<220> FEATURE:
<223> OTHER INFORMATION: Synthetic

<400> SEQUENCE: 413

caggccatta gaaatgat                                                   18


<210> SEQ ID NO 414
<211> LENGTH: 6
<212> TYPE: PRT
<213> ORGANISM: Artificial Sequence
<220> FEATURE:
<223> OTHER INFORMATION: Synthetic

<400> SEQUENCE: 414

Gln Ala Ile Arg Asn Asp
 1               5


<210> SEQ ID NO 415
<211> LENGTH: 9
<212> TYPE: DNA
<213> ORGANISM: Artificial Sequence
<220> FEATURE:
<223> OTHER INFORMATION: Synthetic

<400> SEQUENCE: 415

gctgcattc                                                              9


<210> SEQ ID NO 416
<211> LENGTH: 3
<212> TYPE: PRT
<213> ORGANISM: Artificial Sequence
```

<220> FEATURE:
<223> OTHER INFORMATION: Synthetic

<400> SEQUENCE: 416

```
Ala Ala Phe
 1
```

<210> SEQ ID NO 417
<211> LENGTH: 27
<212> TYPE: DNA
<213> ORGANISM: Artificial Sequence
<220> FEATURE:
<223> OTHER INFORMATION: Synthetic

<400> SEQUENCE: 417

```
caacagtata atagataccc gtggacg                                          27
```

<210> SEQ ID NO 418
<211> LENGTH: 9
<212> TYPE: PRT
<213> ORGANISM: Artificial Sequence
<220> FEATURE:
<223> OTHER INFORMATION: Synthetic

<400> SEQUENCE: 418

```
Gln Gln Tyr Asn Arg Tyr Pro Trp Thr
 1               5
```

<210> SEQ ID NO 419
<211> LENGTH: 357
<212> TYPE: DNA
<213> ORGANISM: Artificial Sequence
<220> FEATURE:
<223> OTHER INFORMATION: Synthetic

<400> SEQUENCE: 419

```
caggtgcagc tggtgcagtc tggggctgag gtgaagaagc ctggggcctc agtgaaggtc     60

tcctgcaagg tttccggatt cactctcact gaattatcca ttcactgggt gcgacaggct    120

cctggaaaag ggcttgagtg gatgggaggt tttgatcctg aagatggtga aacaatctcc    180

gcacagaagt tccagggcag agtcaccatg accgaggaca catctacaga cacagcctac    240

atggaactga gcagcctgag atctgaagac acggccatat attactgttc aacgattttt    300

ggagtggtta ccaactttga caactggggc cagggaaccc tggtcaccgt ctcctca       357
```

<210> SEQ ID NO 420
<211> LENGTH: 119
<212> TYPE: PRT
<213> ORGANISM: Artificial Sequence
<220> FEATURE:
<223> OTHER INFORMATION: Synthetic

<400> SEQUENCE: 420

```
Gln Val Gln Leu Val Gln Ser Gly Ala Glu Val Lys Lys Pro Gly Ala
 1               5                  10                  15

Ser Val Lys Val Ser Cys Lys Val Ser Gly Phe Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Ser Ala Gln Lys Phe
    50                  55                  60

Gln Gly Arg Val Thr Met Thr Glu Asp Thr Ser Thr Asp Thr Ala Tyr
65                  70                  75                  80
```

```
Met Glu Leu Ser Ser Leu Arg Ser Glu Asp Thr Ala Ile Tyr Tyr Cys
                85                  90                  95

Ser Thr Ile Phe Gly Val Val Thr Asn Phe Asp Asn Trp Gly Gln Gly
            100                 105                 110

Thr Leu Val Thr Val Ser Ser
        115


<210> SEQ ID NO 421
<211> LENGTH: 321
<212> TYPE: DNA
<213> ORGANISM: Artificial Sequence
<220> FEATURE:
<223> OTHER INFORMATION: Synthetic

<400> SEQUENCE: 421

gacatccaga tgacccagtc tccatcctcc ctgtctgcat ctgcaggaga cagagtcacc     60

atcacttgcc gggcaagtca ggccattaga aatgatttag gctggtatca gcagaaacca    120

gggaaagccc ctaagcgcct gatctatgct gcattcaatt tgcaaagtgg ggtcccatca    180

agattcagcg gcagtggatc tgggacagaa ttcactctca caatcagtag cctgcagcct    240

gaagatcttg caagttatta ctgtcaacag tataatagat acccgtggac gttcggccaa    300

gggaccaagg tggaaatcaa a                                              321


<210> SEQ ID NO 422
<211> LENGTH: 107
<212> TYPE: PRT
<213> ORGANISM: Artificial Sequence
<220> FEATURE:
<223> OTHER INFORMATION: Synthetic

<400> SEQUENCE: 422

Asp Ile Gln Met Thr Gln Ser Pro Ser Ser Leu Ser Ala Ser Ala Gly
 1               5                  10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Phe Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Leu Ala Ser Tyr Tyr Cys Gln Gln Tyr Asn Arg Tyr Pro Trp
                85                  90                  95

Thr Phe Gly Gln Gly Thr Lys Val Glu Ile Lys
            100                 105


<210> SEQ ID NO 423
<211> LENGTH: 375
<212> TYPE: DNA
<213> ORGANISM: Artificial Sequence
<220> FEATURE:
<223> OTHER INFORMATION: Synthetic

<400> SEQUENCE: 423

caggtgcagc tggtacagtc gggggcggc ttggtacagc ctggcaggtc cctgagactc     60

tcctgtgcag cccctggatt caactttgat gattatgcca tgcactgggt ccggcaaact    120

ccagggaagg gcctggagtg ggtctcaggt attagttgga atagtggtac tataggctat    180

gcggactctg tgaagggccg atttaccatc tccagagaca acgccaagaa ctccctgtat    240
```

```
cttcaaatga acagtctgag agctgaggac acggccttgt attactgtgc aaaagaaggg    300

gtatggttcg gaaaattgtt ctcatcctac ggtatggacg tctggggcca agggaccacg    360

gtcaccgtct cctca                                                     375


<210> SEQ ID NO 424
<211> LENGTH: 125
<212> TYPE: PRT
<213> ORGANISM: Artificial Sequence
<220> FEATURE:
<223> OTHER INFORMATION: Synthetic

<400> SEQUENCE: 424

Gln Val Gln Leu Val Gln Ser Gly Gly Gly Leu Val Gln Pro Gly Arg
 1               5                  10                  15

Ser Leu Arg Leu Ser Cys Ala Ala Pro Gly Phe Asn Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Val Trp Phe Gly Lys Leu Phe Ser Ser Tyr Gly Met
            100                 105                 110

Asp Val Trp Gly Gln Gly Thr Thr Val Thr Val Ser Ser
        115                 120                 125


<210> SEQ ID NO 425
<211> LENGTH: 24
<212> TYPE: DNA
<213> ORGANISM: Artificial Sequence
<220> FEATURE:
<223> OTHER INFORMATION: Synthetic

<400> SEQUENCE: 425

ggattcaact ttgatgatta tgcc                                            24


<210> SEQ ID NO 426
<211> LENGTH: 8
<212> TYPE: PRT
<213> ORGANISM: Artificial Sequence
<220> FEATURE:
<223> OTHER INFORMATION: Synthetic

<400> SEQUENCE: 426

Gly Phe Asn Phe Asp Asp Tyr Ala
 1               5


<210> SEQ ID NO 427
<211> LENGTH: 24
<212> TYPE: DNA
<213> ORGANISM: Artificial Sequence
<220> FEATURE:
<223> OTHER INFORMATION: Synthetic

<400> SEQUENCE: 427

attagttgga atagtggtac tata                                            24


<210> SEQ ID NO 428
<211> LENGTH: 8
```

<212> TYPE: PRT
<213> ORGANISM: Artificial Sequence
<220> FEATURE:
<223> OTHER INFORMATION: Synthetic

<400> SEQUENCE: 428

Ile Ser Trp Asn Ser Gly Thr Ile
1 5

<210> SEQ ID NO 429
<211> LENGTH: 54
<212> TYPE: DNA
<213> ORGANISM: Artificial Sequence
<220> FEATURE:
<223> OTHER INFORMATION: Synthetic

<400> SEQUENCE: 429
gcaaaagaag ggtatggtt cggaaaattg ttctcatcct acggtatgga cgtc 54

<210> SEQ ID NO 430
<211> LENGTH: 18
<212> TYPE: PRT
<213> ORGANISM: Artificial Sequence
<220> FEATURE:
<223> OTHER INFORMATION: Synthetic

<400> SEQUENCE: 430

Ala Lys Glu Gly Val Trp Phe Gly Lys Leu Phe Ser Ser Tyr Gly Met
1 5 10 15

Asp Val

<210> SEQ ID NO 431
<211> LENGTH: 321
<212> TYPE: DNA
<213> ORGANISM: Artificial Sequence
<220> FEATURE:
<223> OTHER INFORMATION: Synthetic

<400> SEQUENCE: 431
gaaatagtga tgacgcagtc tccagccacc ctgtctgtgt ctccagggga aagagccacc 60
ctctcctgca gggccagtcg gactgttact tacaacttag actggtacca gcagaagcct 120
ggccaggctc ccaggctcct catctttggt gcatccacca gggccactgg tatcccagcc 180
aggttcagtg gcagtgggtc tgggacagag ttcactctca ccatcaccag cctgcagtct 240
gaagattttg cagtttatta ctgtcaacag tataataact ggccgtacac ttttggccag 300
gggaccaagc tggagatcaa a 321

<210> SEQ ID NO 432
<211> LENGTH: 107
<212> TYPE: PRT
<213> ORGANISM: Artificial Sequence
<220> FEATURE:
<223> OTHER INFORMATION: Synthetic

<400> SEQUENCE: 432

Glu Ile Val Met Thr Gln Ser Pro Ala Thr Leu Ser Val Ser Pro Gly
1 5 10 15

Glu Arg Ala Thr Leu Ser Cys Arg Ala Ser Arg Thr Val Thr Tyr Asn
20 25 30

Leu Asp Trp Tyr Gln Gln Lys Pro Gly Gln Ala Pro Arg Leu Leu Ile
35 40 45

Phe Gly Ala Ser Thr Arg Ala Thr Gly Ile Pro Ala Arg Phe Ser Gly
50 55 60

```
Ser Gly Ser Gly Thr Glu Phe Thr Leu Thr Ile Thr Ser Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys
            100                 105
```

```
<210> SEQ ID NO 433
<211> LENGTH: 18
<212> TYPE: DNA
<213> ORGANISM: Artificial Sequence
<220> FEATURE:
<223> OTHER INFORMATION: Synthetic

<400> SEQUENCE: 433

cggactgtta cttacaac                                                  18


<210> SEQ ID NO 434
<211> LENGTH: 6
<212> TYPE: PRT
<213> ORGANISM: Artificial Sequence
<220> FEATURE:
<223> OTHER INFORMATION: Synthetic

<400> SEQUENCE: 434

Arg Thr Val Thr Tyr Asn
 1               5


<210> SEQ ID NO 435
<211> LENGTH: 9
<212> TYPE: DNA
<213> ORGANISM: Artificial Sequence
<220> FEATURE:
<223> OTHER INFORMATION: Synthetic

<400> SEQUENCE: 435

ggtgcatcc                                                             9


<210> SEQ ID NO 436
<211> LENGTH: 3
<212> TYPE: PRT
<213> ORGANISM: Artificial Sequence
<220> FEATURE:
<223> OTHER INFORMATION: Synthetic

<400> SEQUENCE: 436

Gly Ala Ser
 1


<210> SEQ ID NO 437
<211> LENGTH: 27
<212> TYPE: DNA
<213> ORGANISM: Artificial Sequence
<220> FEATURE:
<223> OTHER INFORMATION: Synthetic

<400> SEQUENCE: 437

caacagtata ataactggcc gtacact                                        27


<210> SEQ ID NO 438
<211> LENGTH: 9
<212> TYPE: PRT
<213> ORGANISM: Artificial Sequence
<220> FEATURE:
<223> OTHER INFORMATION: Synthetic
```

<400> SEQUENCE: 438

Gln Gln Tyr Asn Asn Trp Pro Tyr Thr
 1               5

<210> SEQ ID NO 439
<211> LENGTH: 375
<212> TYPE: DNA
<213> ORGANISM: Artificial Sequence
<220> FEATURE:
<223> OTHER INFORMATION: Synthetic

<400> SEQUENCE: 439
gaagtgcagc tggtgcagtc tgggggcggc ttggttcagc ctggcgggtc cctgagactc 60
tcctgtgcag cccctggatt caactttgat gattatgcca tgcactgggt ccggcaagct 120
ccagggaagg gcctggagtg ggtctcaggt attagttgga atagtggtag tattggctat 180
gcggactctg tgaagggccg attcaccatc tccagagaca acgccaagaa ctccctgtat 240
ctgcaaatga acagtctgag agctgaggac tcggccttgt atttctgtgc aaaagaaggg 300
gtatggttcg gaaaattatt ttcatcctac ggtatggacg tctggggcca agggaccacg 360
gtcaccgtct cctca 375

<210> SEQ ID NO 440
<211> LENGTH: 125
<212> TYPE: PRT
<213> ORGANISM: Artificial Sequence
<220> FEATURE:
<223> OTHER INFORMATION: Synthetic

<400> SEQUENCE: 440

Glu Val Gln Leu Val Gln Ser Gly Gly Gly Leu Val Gln Pro Gly Gly
 1               5                  10                  15

Ser Leu Arg Leu Ser Cys Ala Ala Pro Gly Phe Asn Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Ser Ala Leu Tyr Phe Cys
                85                  90                  95

Ala Lys Glu Gly Val Trp Phe Gly Lys Leu Phe Ser Ser Tyr Gly Met
            100                 105                 110

Asp Val Trp Gly Gln Gly Thr Thr Val Thr Val Ser Ser
        115                 120                 125

<210> SEQ ID NO 441
<211> LENGTH: 24
<212> TYPE: DNA
<213> ORGANISM: Artificial Sequence
<220> FEATURE:
<223> OTHER INFORMATION: Synthetic

<400> SEQUENCE: 441
ggattcaact ttgatgatta tgcc 24

<210> SEQ ID NO 442
<211> LENGTH: 8
<212> TYPE: PRT
<213> ORGANISM: Artificial Sequence
<220> FEATURE:
<223> OTHER INFORMATION: Synthetic

<400> SEQUENCE: 442

Gly Phe Asn Phe Asp Asp Tyr Ala
 1               5

<210> SEQ ID NO 443
<211> LENGTH: 24
<212> TYPE: DNA
<213> ORGANISM: Artificial Sequence
<220> FEATURE:
<223> OTHER INFORMATION: Synthetic

<400> SEQUENCE: 443
attagttgga atagtggtag tatt 24

<210> SEQ ID NO 444
<211> LENGTH: 8
<212> TYPE: PRT
<213> ORGANISM: Artificial Sequence
<220> FEATURE:
<223> OTHER INFORMATION: Synthetic

<400> SEQUENCE: 444

Ile Ser Trp Asn Ser Gly Ser Ile
 1               5

<210> SEQ ID NO 445
<211> LENGTH: 54
<212> TYPE: DNA
<213> ORGANISM: Artificial Sequence
<220> FEATURE:
<223> OTHER INFORMATION: Synthetic

<400> SEQUENCE: 445
gcaaaagaag ggtatggtt cggaaaatta ttttcatcct acggtatgga cgtc 54

<210> SEQ ID NO 446
<211> LENGTH: 18
<212> TYPE: PRT
<213> ORGANISM: Artificial Sequence
<220> FEATURE:
<223> OTHER INFORMATION: Synthetic

<400> SEQUENCE: 446

Ala Lys Glu Gly Val Trp Phe Gly Lys Leu Phe Ser Ser Tyr Gly Met
 1               5                   10                  15

Asp Val

<210> SEQ ID NO 447
<211> LENGTH: 321
<212> TYPE: DNA
<213> ORGANISM: Artificial Sequence
<220> FEATURE:
<223> OTHER INFORMATION: Synthetic

<400> SEQUENCE: 447
gaaatagtgt tgacgcagtc tccagccacc ctgtctgcgt ctccagggga cagagcctcc 60
ctctcctgca gggccagtca gagtgttacc ttcaacttag actggtacca gcagaaacct 120
ggccagcctc ccaggctcct catctatggt gcatccacca gggcctctgg tatcccagcc 180
aggttcagtg gcagtgggtc tgggacagag ttcactctca ccatcagcgg cctgcagtct 240
gaagattttg cagtttatta ctgtcagcag tataataact ggccgtacac ttttggccag 300
gggaccaaag tggatatcaa a 321

<210> SEQ ID NO 448
<211> LENGTH: 107
<212> TYPE: PRT
<213> ORGANISM: Artificial Sequence
<220> FEATURE:
<223> OTHER INFORMATION: Synthetic

<400> SEQUENCE: 448

```
Glu Ile Val Leu Thr Gln Ser Pro Ala Thr Leu Ser Ala Ser Pro Gly
1               5                   10                  15

Asp Arg Ala Ser Leu Ser Cys Arg Ala Ser Gln Ser Val Thr Phe Asn
            20                  25                  30

Leu Asp Trp Tyr Gln Gln Lys Pro Gly Gln Pro Pro Arg Leu Leu Ile
        35                  40                  45

Tyr Gly Ala Ser Thr Arg Ala Ser Gly Ile Pro Ala Arg Phe Ser Gly
    50                  55                  60

Ser Gly Ser Gly Thr Glu Phe Thr Leu Thr Ile Ser Gly Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Val Asp Ile Lys
            100                 105
```

<210> SEQ ID NO 449
<211> LENGTH: 18
<212> TYPE: DNA
<213> ORGANISM: Artificial Sequence
<220> FEATURE:
<223> OTHER INFORMATION: Synthetic

<400> SEQUENCE: 449
cagagtgtta ccttcaac 18

<210> SEQ ID NO 450
<211> LENGTH: 6
<212> TYPE: PRT
<213> ORGANISM: Artificial Sequence
<220> FEATURE:
<223> OTHER INFORMATION: Synthetic

<400> SEQUENCE: 450

```
Gln Ser Val Thr Phe Asn
1               5
```

<210> SEQ ID NO 451
<211> LENGTH: 9
<212> TYPE: DNA
<213> ORGANISM: Artificial Sequence
<220> FEATURE:
<223> OTHER INFORMATION: Synthetic

<400> SEQUENCE: 451 ggtgcatcc 9

<210> SEQ ID NO 452
<211> LENGTH: 3
<212> TYPE: PRT
<213> ORGANISM: Artificial Sequence
<220> FEATURE:
<223> OTHER INFORMATION: Synthetic

<400> SEQUENCE: 452

```
Gly Ala Ser
 1


<210> SEQ ID NO 453
<211> LENGTH: 27
<212> TYPE: DNA
<213> ORGANISM: Artificial Sequence
<220> FEATURE:
<223> OTHER INFORMATION: Synthetic

<400> SEQUENCE: 453

cagcagtata ataactggcc gtacact                                          27


<210> SEQ ID NO 454
<211> LENGTH: 9
<212> TYPE: PRT
<213> ORGANISM: Artificial Sequence
<220> FEATURE:
<223> OTHER INFORMATION: Synthetic

<400> SEQUENCE: 454

Gln Gln Tyr Asn Asn Trp Pro Tyr Thr
 1               5


<210> SEQ ID NO 455
<211> LENGTH: 375
<212> TYPE: DNA
<213> ORGANISM: Artificial Sequence
<220> FEATURE:
<223> OTHER INFORMATION: Synthetic

<400> SEQUENCE: 455

gaggtgcagc tggtggagtc cggcggcggc ctggtgcagc ccggccggtc cctgcggctg      60

tcctgcgccg cctccggctt caacttcgac gactacgcca tgcactgggt gcggcaggcc     120

cccggcaagg gcctggagtg ggtgtccggc atctcctgga actccggctc catcggctac     180

gccgactccg tgaagggccg gttcaccatc tcccgggaca acgccaagaa ctccctgtac     240

ctgcagatga actccctgcg ggccgaggac accgccctgt actactgcgc caaggagggc     300

gtgtggttcg gcaagctgtt ctcctcctac ggcatggacg tgtggggcca gggcaccacc     360

gtgaccgtgt cctcc                                                      375


<210> SEQ ID NO 456
<211> LENGTH: 125
<212> TYPE: PRT
<213> ORGANISM: Artificial Sequence
<220> FEATURE:
<223> OTHER INFORMATION: Synthetic

<400> SEQUENCE: 456

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Asn Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95
```

```
Ala Lys Glu Gly Val Trp Phe Gly Lys Leu Phe Ser Ser Tyr Gly Met
            100                 105                 110

Asp Val Trp Gly Gln Gly Thr Thr Val Thr Val Ser Ser
        115                 120                 125


<210> SEQ ID NO 457
<211> LENGTH: 321
<212> TYPE: DNA
<213> ORGANISM: Artificial Sequence
<220> FEATURE:
<223> OTHER INFORMATION: Synthetic

<400> SEQUENCE: 457

gagatcgtga tgacccagtc ccccgccacc ctgtccgtgt cccccggcga gcgggccacc      60

ctgtcctgcc gggcctccca gtccgtgacc ttcaacctgg cctggtacca gcagaagccc     120

ggccagcccg cccggctgct gatctacggc gcctccaccc gggccaccgg catccccgcc     180

cggttctccg gctccggctc cggcaccgag ttcaccctga ccatctcctc cctgcagtcc     240

gaggacttcg ccgtgtacta ctgccagcag tacaacaact ggccctacac cttcggccag     300

ggcaccaagc tggagatcaa g                                               321


<210> SEQ ID NO 458
<211> LENGTH: 107
<212> TYPE: PRT
<213> ORGANISM: Artificial Sequence
<220> FEATURE:
<223> OTHER INFORMATION: Synthetic

<400> SEQUENCE: 458

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Thr Phe Asn
            20                  25                  30

Leu Ala Trp Tyr Gln Gln Lys Pro Gly Gln Pro Ala Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys
            100                 105


<210> SEQ ID NO 459
<211> LENGTH: 375
<212> TYPE: DNA
<213> ORGANISM: Artificial Sequence
<220> FEATURE:
<223> OTHER INFORMATION: Synthetic

<400> SEQUENCE: 459

gaggtgcagc tggtggagtc tgggggcggc ttggttcagc ctggcgggtc cctgagactc      60

tcctgtgcag cccctggatt caactttgat gattatgcca tgcactgggt ccggcaagct     120

ccagggaagg gcctggagtg ggtctcaggt attagttgga atagtggtag tattggctat     180

gcggactctg tgaagggccg attcaccatc tccagagaca acgccaagaa ctccctgtat     240

ctgcaaatga acagtctgag agctgaggac tcggccttgt atttctgtgc aaaagaaggg     300

gtatggttcg gaaaattatt ttcatcctac ggtatggacg tctggggcca agggaccacg     360
```

```
gtcaccgtct cctca                                                375

<210> SEQ ID NO 460
<211> LENGTH: 125
<212> TYPE: PRT
<213> ORGANISM: Artificial Sequence
<220> FEATURE:
<223> OTHER INFORMATION: Synthetic

<400> SEQUENCE: 460

Glu Val Gln Leu Val Glu Ser Gly Gly Gly Leu Val Gln Pro Gly Gly
1               5                   10                  15

Ser Leu Arg Leu Ser Cys Ala Ala Pro Gly Phe Asn Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Ser Ala Leu Tyr Phe Cys
                85                  90                  95

Ala Lys Glu Gly Val Trp Phe Gly Lys Leu Phe Ser Ser Tyr Gly Met
            100                 105                 110

Asp Val Trp Gly Gln Gly Thr Thr Val Thr Val Ser Ser
        115                 120                 125


<210> SEQ ID NO 461
<211> LENGTH: 321
<212> TYPE: DNA
<213> ORGANISM: Artificial Sequence
<220> FEATURE:
<223> OTHER INFORMATION: Synthetic

<400> SEQUENCE: 461

gaaatagtga tgacgcagtc tccagccacc ctgtctgcgt ctccagggga cagagcctcc     60

ctctcctgca gggccagtca gagtgttacc ttcaacttag actggtacca gcagaaacct    120

ggccagcctc ccaggctcct catctatggt gcatccacca gggcctctgg tatcccagcc    180

aggttcagtg gcagtgggtc tgggacagag ttcactctca ccatcagcgg cctgcagtct    240

gaagattttg cagtttatta ctgtcagcag tataataact ggccgtacac ttttggccag    300

gggaccaagc tggagatcaa a                                              321


<210> SEQ ID NO 462
<211> LENGTH: 107
<212> TYPE: PRT
<213> ORGANISM: Artificial Sequence
<220> FEATURE:
<223> OTHER INFORMATION: Synthetic

<400> SEQUENCE: 462

Glu Ile Val Met Thr Gln Ser Pro Ala Thr Leu Ser Ala Ser Pro Gly
1               5                   10                  15

Asp Arg Ala Ser Leu Ser Cys Arg Ala Ser Gln Ser Val Thr Phe Asn
            20                  25                  30

Leu Asp Trp Tyr Gln Gln Lys Pro Gly Gln Pro Pro Arg Leu Leu Ile
        35                  40                  45

Tyr Gly Ala Ser Thr Arg Ala Ser Gly Ile Pro Ala Arg Phe Ser Gly
    50                  55                  60
```

```
Ser Gly Ser Gly Thr Glu Phe Thr Leu Thr Ile Ser Gly Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys
            100                 105


<210> SEQ ID NO 463
<211> LENGTH: 375
<212> TYPE: DNA
<213> ORGANISM: Artificial Sequence
<220> FEATURE:
<223> OTHER INFORMATION: Synthetic

<400> SEQUENCE: 463

caggtgcagc tggtacagtc gggggaggc ttggtacagc ctggcaggtc cctgagactc     60

tcctgtgcag cctctggatt cacctttgat gattatgcca tgcactgggt ccggcaaggt    120

ccagggaagg gcctagagtg ggtctcaggt attagttgga atagtggtta taaagactat    180

gcggactctg tgaagggccg attcaccatc tccagagaca acgccaagaa gtccctgtat    240

ctgcaaatga acagtctgag acctgaggac acggccttgt attactgtgc aaaagaaggg    300

gtatggttcg gagaattatt ttcatcctac ggtatggacg tctggggcca agggaccacg    360

gtcaccgtct cctca                                                     375


<210> SEQ ID NO 464
<211> LENGTH: 125
<212> TYPE: PRT
<213> ORGANISM: Artificial Sequence
<220> FEATURE:
<223> OTHER INFORMATION: Synthetic

<400> SEQUENCE: 464

Gln Val Gln Leu Val Gln Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Gly Pro Gly Lys Gly Leu Glu Trp Val
        35                  40                  45

Ser Gly Ile Ser Trp Asn Ser Gly Tyr Lys Asp Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Pro Glu Asp Thr Ala Leu Tyr Tyr Cys
                85                  90                  95

Ala Lys Glu Gly Val Trp Phe Gly Glu Leu Phe Ser Ser Tyr Gly Met
            100                 105                 110

Asp Val Trp Gly Gln Gly Thr Thr Val Thr Val Ser Ser
        115                 120                 125


<210> SEQ ID NO 465
<211> LENGTH: 24
<212> TYPE: DNA
<213> ORGANISM: Artificial Sequence
<220> FEATURE:
<223> OTHER INFORMATION: Synthetic

<400> SEQUENCE: 465

ggattcacct ttgatgatta tgcc                                           24
```

<210> SEQ ID NO 466
<211> LENGTH: 8
<212> TYPE: PRT
<213> ORGANISM: Artificial Sequence
<220> FEATURE:
<223> OTHER INFORMATION: Synthetic

<400> SEQUENCE: 466

Gly Phe Thr Phe Asp Asp Tyr Ala
1 5

<210> SEQ ID NO 467
<211> LENGTH: 24
<212> TYPE: DNA
<213> ORGANISM: Artificial Sequence
<220> FEATURE:
<223> OTHER INFORMATION: Synthetic

<400> SEQUENCE: 467
attagttgga atagtggtta taaa 24

<210> SEQ ID NO 468
<211> LENGTH: 8
<212> TYPE: PRT
<213> ORGANISM: Artificial Sequence
<220> FEATURE:
<223> OTHER INFORMATION: Synthetic

<400> SEQUENCE: 468

Ile Ser Trp Asn Ser Gly Tyr Lys
1 5

<210> SEQ ID NO 469
<211> LENGTH: 54
<212> TYPE: DNA
<213> ORGANISM: Artificial Sequence
<220> FEATURE:
<223> OTHER INFORMATION: Synthetic

<400> SEQUENCE: 469
gcaaaagaag ggtatggtt cggagaatta ttttcatcct acggtatgga cgtc 54

<210> SEQ ID NO 470
<211> LENGTH: 18
<212> TYPE: PRT
<213> ORGANISM: Artificial Sequence
<220> FEATURE:
<223> OTHER INFORMATION: Synthetic

<400> SEQUENCE: 470

Ala Lys Glu Gly Val Trp Phe Gly Glu Leu Phe Ser Ser Tyr Gly Met
1 5 10 15

Asp Val

<210> SEQ ID NO 471
<211> LENGTH: 321
<212> TYPE: DNA
<213> ORGANISM: Artificial Sequence
<220> FEATURE:
<223> OTHER INFORMATION: Synthetic

<400> SEQUENCE: 471
gaaattgtga tgacgcagtc tccagccacc ctgtctgtgt ctccagggga aagagccacc 60
ctctcctgca gggccagtcc gagtgttagc agcaacttag cctggtacca gcagaaacct 120
ggccagcctc ccaggctcct catctatggt acatccacca gggccactgg tatcccagcc 180

```
aggttcagtg gcagtgggtc tgggacagag ttcactctca ccatcagaag cctgcagtct    240

gaagattttg cagtttatta ctgtcagcag tatagtaact ggccatacac ttttggccag    300

gggaccaaag tggatatcaa a                                              321


<210> SEQ ID NO 472
<211> LENGTH: 107
<212> TYPE: PRT
<213> ORGANISM: Artificial Sequence
<220> FEATURE:
<223> OTHER INFORMATION: Synthetic

<400> SEQUENCE: 472

Glu Ile Val Met Thr Gln Ser Pro Ala Thr Leu Ser Val Ser Pro Gly
 1               5                  10                  15

Glu Arg Ala Thr Leu Ser Cys Arg Ala Ser Pro Ser Val Ser Ser Asn
            20                  25                  30

Leu Ala Trp Tyr Gln Gln Lys Pro Gly Gln Pro Pro Arg Leu Leu Ile
        35                  40                  45

Tyr Gly Thr Ser Thr Arg Ala Thr Gly Ile Pro Ala Arg Phe Ser Gly
    50                  55                  60

Ser Gly Ser Gly Thr Glu Phe Thr Leu Thr Ile Arg Ser Leu Gln Ser
65                  70                  75                  80

Glu Asp Phe Ala Val Tyr Tyr Cys Gln Gln Tyr Ser Asn Trp Pro Tyr
                85                  90                  95

Thr Phe Gly Gln Gly Thr Lys Val Asp Ile Lys
            100                 105


<210> SEQ ID NO 473
<211> LENGTH: 18
<212> TYPE: DNA
<213> ORGANISM: Artificial Sequence
<220> FEATURE:
<223> OTHER INFORMATION: Synthetic

<400> SEQUENCE: 473

ccgagtgtta gcagcaac                                                   18


<210> SEQ ID NO 474
<211> LENGTH: 6
<212> TYPE: PRT
<213> ORGANISM: Artificial Sequence
<220> FEATURE:
<223> OTHER INFORMATION: Synthetic

<400> SEQUENCE: 474

Pro Ser Val Ser Ser Asn
 1               5


<210> SEQ ID NO 475
<211> LENGTH: 9
<212> TYPE: DNA
<213> ORGANISM: Artificial Sequence
<220> FEATURE:
<223> OTHER INFORMATION: Synthetic

<400> SEQUENCE: 475

ggtacatcc                                                              9


<210> SEQ ID NO 476
<211> LENGTH: 3
<212> TYPE: PRT
<213> ORGANISM: Artificial Sequence
```

<220> FEATURE:
<223> OTHER INFORMATION: Synthetic

<400> SEQUENCE: 476

Gly Thr Ser
 1

<210> SEQ ID NO 477
<211> LENGTH: 27
<212> TYPE: DNA
<213> ORGANISM: Artificial Sequence
<220> FEATURE:
<223> OTHER INFORMATION: Synthetic

<400> SEQUENCE: 477
cagcagtata gtaactggcc atacact 27

<210> SEQ ID NO 478
<211> LENGTH: 9
<212> TYPE: PRT
<213> ORGANISM: Artificial Sequence
<220> FEATURE:
<223> OTHER INFORMATION: Synthetic

<400> SEQUENCE: 478

Gln Gln Tyr Ser Asn Trp Pro Tyr Thr
 1               5

<210> SEQ ID NO 479
<211> LENGTH: 375
<212> TYPE: DNA
<213> ORGANISM: Artificial Sequence
<220> FEATURE:
<223> OTHER INFORMATION: Synthetic

<400> SEQUENCE: 479
gaggtgcagc tggtggagtc cggcggcggc ctggtgcagc ccggccggtc cctgcggctg 60
tcctgcgccg cctccggctt caccttcgac gactacgcca tgcactgggt gcggcaggcc 120
cccggcaagg gcctggagtg ggtgtccggc atctcctgga actccggcta caagggctac 180
gccgactccg tgaagggccg gttcaccatc tcccgggaca acgccaagaa ctccctgtac 240
ctgcagatga actccctgcg ggccgaggac accgccctgt actactgcgc caaggagggc 300
gtgtggttcg gcgagctgtt ctcctcctac ggcatggacg tgtggggcca gggcaccacc 360
gtgaccgtgt cctcc 375

<210> SEQ ID NO 480
<211> LENGTH: 125
<212> TYPE: PRT
<213> ORGANISM: Artificial Sequence
<220> FEATURE:
<223> OTHER INFORMATION: Synthetic

<400> SEQUENCE: 480

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Tyr Lys Gly Tyr Ala Asp Ser Val
    50                  55                  60

Lys Gly Arg Phe Thr Ile Ser Arg Asp Asn Ala Lys Asn Ser Leu Tyr

```
65                  70                  75                  80

Leu Gln Met Asn Ser Leu Arg Ala Glu Asp Thr Ala Leu Tyr Tyr Cys
                85                  90                  95

Ala Lys Glu Gly Val Trp Phe Gly Glu Leu Phe Ser Ser Tyr Gly Met
            100                 105                 110

Asp Val Trp Gly Gln Gly Thr Thr Val Thr Val Ser Ser
        115                 120                 125


<210> SEQ ID NO 481
<211> LENGTH: 321
<212> TYPE: DNA
<213> ORGANISM: Artificial Sequence
<220> FEATURE:
<223> OTHER INFORMATION: Synthetic

<400> SEQUENCE: 481

gagatcgtga tgacccagtc ccccgccacc ctgtccgtgt cccccggcga gcgggccacc      60

ctgtcctgcc gggcctcccc ctccgtgtcc tccaacctgg cctggtacca gcagaagccc     120

ggccaggccc cccggctgct gatctacggc acctccaccc gggccaccgg catccccgcc     180

cggttctccg gctccggctc cggcaccgag ttcaccctga ccatctcctc cctgcagtcc     240

gaggacttcg ccgtgtacta ctgccagcag tactccaact ggccctacac cttcggccag     300

ggcaccaagc tggagatcaa g                                                321


<210> SEQ ID NO 482
<211> LENGTH: 107
<212> TYPE: PRT
<213> ORGANISM: Artificial Sequence
<220> FEATURE:
<223> OTHER INFORMATION: Synthetic

<400> SEQUENCE: 482

Glu Ile Val Met Thr Gln Ser Pro Ala Thr Leu Ser Val Ser Pro Gly
 1               5                   10                  15

Glu Arg Ala Thr Leu Ser Cys Arg Ala Ser Pro Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Thr Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Asn Trp Pro Tyr
                85                  90                  95

Thr Phe Gly Gln Gly Thr Lys Leu Glu Ile Lys
            100                 105


<210> SEQ ID NO 483
<211> LENGTH: 375
<212> TYPE: DNA
<213> ORGANISM: Artificial Sequence
<220> FEATURE:
<223> OTHER INFORMATION: Synthetic

<400> SEQUENCE: 483

gaggtgcagc tggtggagtc tgggggaggc ttggtacagc ctggcaggtc cctgagactc      60

tcctgtgcag cctctggatt cacctttgat gattatgcca tgcactgggt ccggcaaggt     120

ccagggaagg gcctagagtg ggtctcaggt attagttgga atagtggtta taaagactat     180
```

```
gcggactctg tgaagggccg attcaccatc tccagagaca acgccaagaa gtccctgtat    240

ctgcaaatga acagtctgag acctgaggac acggccttgt attactgtgc aaaagaaggg    300

gtatggttcg gagaattatt ttcatcctac ggtatggacg tctggggcca agggaccacg    360

gtcaccgtct cctca                                                     375
```

<210> SEQ ID NO 484
<211> LENGTH: 125
<212> TYPE: PRT
<213> ORGANISM: Artificial Sequence
<220> FEATURE:
<223> OTHER INFORMATION: Synthetic

<400> SEQUENCE: 484

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Gly Pro Gly Lys Gly Leu Glu Trp Val
        35                  40                  45

Ser Gly Ile Ser Trp Asn Ser Gly Tyr Lys Asp Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Pro Glu Asp Thr Ala Leu Tyr Tyr Cys
                85                  90                  95

Ala Lys Glu Gly Val Trp Phe Gly Glu Leu Phe Ser Ser Tyr Gly Met
            100                 105                 110

Asp Val Trp Gly Gln Gly Thr Thr Val Thr Val Ser Ser
        115                 120                 125
```

<210> SEQ ID NO 485
<211> LENGTH: 321
<212> TYPE: DNA
<213> ORGANISM: Artificial Sequence
<220> FEATURE:
<223> OTHER INFORMATION: Synthetic

<400> SEQUENCE: 485

```
gaaatagtga tgacgcagtc tccagccacc ctgtctgtgt ctccagggga aagagccacc     60

ctctcctgca gggccagtcc gagtgttagc agcaacttag cctggtacca gcagaaacct    120

ggccagcctc ccaggctcct catctatggt acatccacca gggccactgg tatcccagcc    180

aggttcagtg gcagtgggtc tgggacagag ttcactctca ccatcagaag cctgcagtct    240

gaagattttg cagtttatta ctgtcagcag tatagtaact ggccatacac ttttggccag    300

gggaccaagc tggagatcaa a                                              321
```

<210> SEQ ID NO 486
<211> LENGTH: 107
<212> TYPE: PRT
<213> ORGANISM: Artificial Sequence
<220> FEATURE:
<223> OTHER INFORMATION: Synthetic

<400> SEQUENCE: 486

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Pro Ser Val Ser Ser Asn
            20                  25                  30
```

```
Leu Ala Trp Tyr Gln Gln Lys Pro Gly Gln Pro Pro Arg Leu Leu Ile
        35                  40                  45

Tyr Gly Thr Ser Thr Arg Ala Thr Gly Ile Pro Ala Arg Phe Ser Gly
    50                  55                  60

Ser Gly Ser Gly Thr Glu Phe Thr Leu Thr Ile Arg Ser Leu Gln Ser
65                  70                  75                  80

Glu Asp Phe Ala Val Tyr Tyr Cys Gln Gln Tyr Ser Asn Trp Pro Tyr
                85                  90                  95

Thr Phe Gly Gln Gly Thr Lys Leu Glu Ile Lys
            100                 105
```

<210> SEQ ID NO 487
<211> LENGTH: 375
<212> TYPE: DNA
<213> ORGANISM: Artificial Sequence
<220> FEATURE:
<223> OTHER INFORMATION: Synthetic

<400> SEQUENCE: 487

```
gaggtgcagc tggtgcagtc tggggggaggc ttggtacagc ccggtaggtc cctgagactc     60

tcctgtacag cctctaaatt cacctttgaa gattatgcca tgcactgggt ccggcaagtt    120

ccagggaagg gcctggaatg ggtctcaggg attagttgga atagtggtaa cataggctat    180

gcggactctg tgaagggccg attcaccatc tccagagaca acgccaagaa ctccctgtat    240

ctgcgaatga atagtctgag agctgatgac acggccttgt attactgtgt gaaggaaggg    300

gtatggttcg ggaagtcatt ttcatcctac ggtttggacg tctggggcca agggaccacg    360

gtcaccgtct cctca                                                     375
```

<210> SEQ ID NO 488
<211> LENGTH: 125
<212> TYPE: PRT
<213> ORGANISM: Artificial Sequence
<220> FEATURE:
<223> OTHER INFORMATION: Synthetic

<400> SEQUENCE: 488

```
Glu Val Gln Leu Val Gln Ser Gly Gly Gly Leu Val Gln Pro Gly Arg
 1               5                  10                  15

Ser Leu Arg Leu Ser Cys Thr Ala Ser Lys Phe Thr Phe Glu Asp Tyr
            20                  25                  30

Ala Met His Trp Val Arg Gln Val Pro Gly Lys Gly Leu Glu Trp Val
        35                  40                  45

Ser Gly Ile Ser Trp Asn Ser Gly Asn Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Arg Met Asn Ser Leu Arg Ala Asp Asp Thr Ala Leu Tyr Tyr Cys
                85                  90                  95

Val Lys Glu Gly Val Trp Phe Gly Lys Ser Phe Ser Ser Tyr Gly Leu
            100                 105                 110

Asp Val Trp Gly Gln Gly Thr Thr Val Thr Val Ser Ser
        115                 120                 125
```

<210> SEQ ID NO 489
<211> LENGTH: 24
<212> TYPE: DNA
<213> ORGANISM: Artificial Sequence
<220> FEATURE:
<223> OTHER INFORMATION: Synthetic

<400> SEQUENCE: 489
aaattcacct ttgaagatta tgcc 24

<210> SEQ ID NO 490
<211> LENGTH: 8
<212> TYPE: PRT
<213> ORGANISM: Artificial Sequence
<220> FEATURE:
<223> OTHER INFORMATION: Synthetic

<400> SEQUENCE: 490

Lys Phe Thr Phe Glu Asp Tyr Ala
1 5

<210> SEQ ID NO 491
<211> LENGTH: 24
<212> TYPE: DNA
<213> ORGANISM: Artificial Sequence
<220> FEATURE:
<223> OTHER INFORMATION: Synthetic

<400> SEQUENCE: 491
attagttgga atagtggtaa cata 24

<210> SEQ ID NO 492
<211> LENGTH: 8
<212> TYPE: PRT
<213> ORGANISM: Artificial Sequence
<220> FEATURE:
<223> OTHER INFORMATION: Synthetic

<400> SEQUENCE: 492

Ile Ser Trp Asn Ser Gly Asn Ile
1 5

<210> SEQ ID NO 493
<211> LENGTH: 54
<212> TYPE: DNA
<213> ORGANISM: Artificial Sequence
<220> FEATURE:
<223> OTHER INFORMATION: Synthetic

<400> SEQUENCE: 493
gtgaaggaag ggtatggtt cgggaagtca ttttcatcct acggtttgga cgtc 54

<210> SEQ ID NO 494
<211> LENGTH: 18
<212> TYPE: PRT
<213> ORGANISM: Artificial Sequence
<220> FEATURE:
<223> OTHER INFORMATION: Synthetic

<400> SEQUENCE: 494

Val Lys Glu Gly Val Trp Phe Gly Lys Ser Phe Ser Ser Tyr Gly Leu
1 5 10 15

Asp Val

<210> SEQ ID NO 495
<211> LENGTH: 321
<212> TYPE: DNA
<213> ORGANISM: Artificial Sequence
<220> FEATURE:
<223> OTHER INFORMATION: Synthetic

<400> SEQUENCE: 495

```
gaaatagtga tgacacagtc tccagccacc ctgtctgtgt ctccggggga aagagccacc     60

ctctcttgca gggccagtca gagtgttagc agcaacttag cctggtatca gcagaaacct    120

ggccaggctc ccaggctcct catctatggt gcatccacca gggccactgg tgtcccagcc    180

aggttcagtg gcagtgggtc tgggacagag ttcactctca ccatcagcag cctgcagtct    240

gaagattttg cagtttatta ctgtcaacat tataattact ggccgtacac ttttggccag    300

gggaccaaag tggatatcaa a                                              321
```

<210> SEQ ID NO 496
<211> LENGTH: 107
<212> TYPE: PRT
<213> ORGANISM: Artificial Sequence
<220> FEATURE:
<223> OTHER INFORMATION: Synthetic

<400> SEQUENCE: 496

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Asn Tyr Trp Pro Tyr
                85                  90                  95

Thr Phe Gly Gln Gly Thr Lys Val Asp Ile Lys
            100                 105
```

<210> SEQ ID NO 497
<211> LENGTH: 18
<212> TYPE: DNA
<213> ORGANISM: Artificial Sequence
<220> FEATURE:
<223> OTHER INFORMATION: Synthetic

<400> SEQUENCE: 497

```
cagagtgtta gcagcaac                                                   18
```

<210> SEQ ID NO 498
<211> LENGTH: 6
<212> TYPE: PRT
<213> ORGANISM: Artificial Sequence
<220> FEATURE:
<223> OTHER INFORMATION: Synthetic

<400> SEQUENCE: 498

```
Gln Ser Val Ser Ser Asn
 1               5
```

<210> SEQ ID NO 499
<211> LENGTH: 9
<212> TYPE: DNA
<213> ORGANISM: Artificial Sequence
<220> FEATURE:
<223> OTHER INFORMATION: Synthetic

<400> SEQUENCE: 499

```
ggtgcatcc                                                              9
```

<210> SEQ ID NO 500
<211> LENGTH: 3
<212> TYPE: PRT
<213> ORGANISM: Artificial Sequence
<220> FEATURE:
<223> OTHER INFORMATION: Synthetic

<400> SEQUENCE: 500

Gly Ala Ser
1

<210> SEQ ID NO 501
<211> LENGTH: 27
<212> TYPE: DNA
<213> ORGANISM: Artificial Sequence
<220> FEATURE:
<223> OTHER INFORMATION: Synthetic

<400> SEQUENCE: 501
caacattata attactggcc gtacact 27

<210> SEQ ID NO 502
<211> LENGTH: 9
<212> TYPE: PRT
<213> ORGANISM: Artificial Sequence
<220> FEATURE:
<223> OTHER INFORMATION: Synthetic

<400> SEQUENCE: 502

Gln His Tyr Asn Tyr Trp Pro Tyr Thr
1 5

<210> SEQ ID NO 503
<211> LENGTH: 375
<212> TYPE: DNA
<213> ORGANISM: Artificial Sequence
<220> FEATURE:
<223> OTHER INFORMATION: Synthetic

<400> SEQUENCE: 503
gaggtgcagc tggtggagtc cggcggcggc ctggtgcagc ccggccggtc cctgcggctg 60
tcctgcgccg cctccaagtt caccttcgag gactacgcca tgcactgggt gcggcaggcc 120
cccggcaagg gcctggagtg ggtgtccggc atctcctgga actccggcaa catcggctac 180
gccgactccg tgaagggccg gttcaccatc tcccgggaca acgccaagaa ctccctgtac 240
ctgcagatga actccctgcg ggccgaggac accgccctgt actactgcgt gaaggagggc 300
gtgtggttcg gcaagtcctt ctcctcctac ggcctggacg tgtggggcca gggcaccacc 360
gtgaccgtgt cctcc 375

<210> SEQ ID NO 504
<211> LENGTH: 125
<212> TYPE: PRT
<213> ORGANISM: Artificial Sequence
<220> FEATURE:
<223> OTHER INFORMATION: Synthetic

<400> SEQUENCE: 504

Glu Val Gln Leu Val Glu Ser Gly Gly Gly Leu Val Gln Pro Gly Arg
1 5 10 15

Ser Leu Arg Leu Ser Cys Ala Ala Ser Lys Phe Thr Phe Glu Asp Tyr
20 25 30

Ala Met His Trp Val Arg Gln Ala Pro Gly Lys Gly Leu Glu Trp Val
35 40 45

```
Ser Gly Ile Ser Trp Asn Ser Gly Asn Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Glu Gly Val Trp Phe Gly Lys Ser Phe Ser Ser Tyr Gly Leu
            100                 105                 110

Asp Val Trp Gly Gln Gly Thr Thr Val Thr Val Ser Ser
        115                 120                 125


<210> SEQ ID NO 505
<211> LENGTH: 321
<212> TYPE: DNA
<213> ORGANISM: Artificial Sequence
<220> FEATURE:
<223> OTHER INFORMATION: Synthetic

<400> SEQUENCE: 505

gagatcgtga tgacccagtc ccccgccacc ctgtccgtgt cccccggcga gcgggccacc     60

ctgtcctgcc gggcctccca gtccgtgtcc tccaacctgg cctggtacca gcagaagccc    120

ggccaggccc cccggctgct gatctacggc gcctccaccc gggccaccgg catccccgcc    180

cggttctccg gctccggctc cggcaccgag ttcaccctga ccatctcctc cctgcagtcc    240

gaggacttcg ccgtgtacta ctgccagcac tacaactact ggccctacac cttcggccag    300

ggcaccaagc tggagatcaa g                                              321


<210> SEQ ID NO 506
<211> LENGTH: 107
<212> TYPE: PRT
<213> ORGANISM: Artificial Sequence
<220> FEATURE:
<223> OTHER INFORMATION: Synthetic

<400> SEQUENCE: 506

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Asn Tyr Trp Pro Tyr
                85                  90                  95

Thr Phe Gly Gln Gly Thr Lys Leu Glu Ile Lys
            100                 105


<210> SEQ ID NO 507
<211> LENGTH: 375
<212> TYPE: DNA
<213> ORGANISM: Artificial Sequence
<220> FEATURE:
<223> OTHER INFORMATION: Synthetic

<400> SEQUENCE: 507

gaggtgcagc tggtggagtc tgggggaggc ttggtacagc ccggtaggtc cctgagactc     60
```

```
tcctgtacag cctctaaatt cacctttgaa gattatgcca tgcactgggt ccggcaagtt    120

ccagggaagg gcctggaatg ggtctcaggg attagttgga atagtggtaa cataggctat    180

gcggactctg tgaagggccg attcaccatc tccagagaca acgccaagaa ctccctgtat    240

ctgcgaatga atagtctgag agctgatgac acggccttgt attactgtgt gaaggaaggg    300

gtatggttcg ggaagtcatt ttcatcctac ggtttggacg tctggggcca agggaccacg    360

gtcaccgtct cctca                                                      375


<210> SEQ ID NO 508
<211> LENGTH: 125
<212> TYPE: PRT
<213> ORGANISM: Artificial Sequence
<220> FEATURE:
<223> OTHER INFORMATION: Synthetic

<400> SEQUENCE: 508

Glu Val Gln Leu Val Glu Ser Gly Gly Gly Leu Val Gln Pro Gly Arg
1               5                   10                  15

Ser Leu Arg Leu Ser Cys Thr Ala Ser Lys Phe Thr Phe Glu Asp Tyr
            20                  25                  30

Ala Met His Trp Val Arg Gln Val Pro Gly Lys Gly Leu Glu Trp Val
        35                  40                  45

Ser Gly Ile Ser Trp Asn Ser Gly Asn Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Arg Met Asn Ser Leu Arg Ala Asp Asp Thr Ala Leu Tyr Tyr Cys
                85                  90                  95

Val Lys Glu Gly Val Trp Phe Gly Lys Ser Phe Ser Ser Tyr Gly Leu
            100                 105                 110

Asp Val Trp Gly Gln Gly Thr Thr Val Thr Val Ser Ser
        115                 120                 125


<210> SEQ ID NO 509
<211> LENGTH: 321
<212> TYPE: DNA
<213> ORGANISM: Artificial Sequence
<220> FEATURE:
<223> OTHER INFORMATION: Synthetic

<400> SEQUENCE: 509

gaaatagtga tgacgcagtc tccagccacc ctgtctgtgt ctccggggga aagagccacc     60

ctctcttgca gggccagtca gagtgttagc agcaacttag cctggtatca gcagaaacct    120

ggccaggctc ccaggctcct catctatggt gcatccacca gggccactgg tgtcccagcc    180

aggttcagtg gcagtgggtc tgggacagag ttcactctca ccatcagcag cctgcagtct    240

gaagattttg cagtttatta ctgtcaacat tataattact ggccgtacac ttttggccag    300

gggaccaagc tggagatcaa a                                               321


<210> SEQ ID NO 510
<211> LENGTH: 107
<212> TYPE: PRT
<213> ORGANISM: Artificial Sequence
<220> FEATURE:
<223> OTHER INFORMATION: Synthetic

<400> SEQUENCE: 510

Glu Ile Val Met Thr Gln Ser Pro Ala Thr Leu Ser Val Ser Pro Gly
```

```
 1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Asn Tyr Trp Pro Tyr
                85                  90                  95

Thr Phe Gly Gln Gly Thr Lys Leu Glu Ile Lys
            100                 105


<210> SEQ ID NO 511
<211> LENGTH: 357
<212> TYPE: DNA
<213> ORGANISM: Artificial Sequence
<220> FEATURE:
<223> OTHER INFORMATION: Synthetic

<400> SEQUENCE: 511

gaagtgcagc tggtgcagtc tggggctgat gtgaagaagc ctggggcctc agtgaaggtc     60

tcctgcaagg tttccggata caccctcact gaattatcca tacactgggt gcgacaggct    120

cctggaaaag ggcttgaatg gatgggaggt tttgatcctg aacatggtac aacaatctac    180

gcacagaagt tccagggcag agtcaccatg accgaggaca catctacaga cacagcctac    240

atggagctga gcagcctgag atctgaggac acggccgtgt attactgtgt aatgattttt    300

ggcgtggtta ccaattttga caactggggc cagggaacca cggtcaccgt ctcctca       357


<210> SEQ ID NO 512
<211> LENGTH: 119
<212> TYPE: PRT
<213> ORGANISM: Artificial Sequence
<220> FEATURE:
<223> OTHER INFORMATION: Synthetic

<400> SEQUENCE: 512

Glu Val Gln Leu Val Gln Ser Gly Ala Asp Val Lys Lys Pro Gly Ala
 1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu His Gly Thr Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Met Ile Phe Gly Val Val Thr Asn Phe Asp Asn Trp Gly Gln Gly
            100                 105                 110

Thr Thr Val Thr Val Ser Ser
        115


<210> SEQ ID NO 513
<211> LENGTH: 24
<212> TYPE: DNA
```

<213> ORGANISM: Artificial Sequence
<220> FEATURE:
<223> OTHER INFORMATION: Synthetic

<400> SEQUENCE: 513
ggatacaccc tcactgaatt atcc 24

<210> SEQ ID NO 514
<211> LENGTH: 8
<212> TYPE: PRT
<213> ORGANISM: Artificial Sequence
<220> FEATURE:
<223> OTHER INFORMATION: Synthetic

<400> SEQUENCE: 514

Gly Tyr Thr Leu Thr Glu Leu Ser
1 5

<210> SEQ ID NO 515
<211> LENGTH: 24
<212> TYPE: DNA
<213> ORGANISM: Artificial Sequence
<220> FEATURE:
<223> OTHER INFORMATION: Synthetic

<400> SEQUENCE: 515
tttgatcctg aacatggtac aaca 24

<210> SEQ ID NO 516
<211> LENGTH: 8
<212> TYPE: PRT
<213> ORGANISM: Artificial Sequence
<220> FEATURE:
<223> OTHER INFORMATION: Synthetic

<400> SEQUENCE: 516

Phe Asp Pro Glu His Gly Thr Thr
1 5

<210> SEQ ID NO 517
<211> LENGTH: 36
<212> TYPE: DNA
<213> ORGANISM: Artificial Sequence
<220> FEATURE:
<223> OTHER INFORMATION: Synthetic

<400> SEQUENCE: 517
gtaatgattt ttggcgtggt taccaatttt gacaac 36

<210> SEQ ID NO 518
<211> LENGTH: 12
<212> TYPE: PRT
<213> ORGANISM: Artificial Sequence
<220> FEATURE:
<223> OTHER INFORMATION: Synthetic

<400> SEQUENCE: 518

Val Met Ile Phe Gly Val Val Thr Asn Phe Asp Asn
1 5 10

<210> SEQ ID NO 519
<211> LENGTH: 321
<212> TYPE: DNA
<213> ORGANISM: Artificial Sequence
<220> FEATURE:
<223> OTHER INFORMATION: Synthetic

<400> SEQUENCE: 519

```
gacattgtga tgacccagtc tccatcctcc ctgtctgcat ccgtgagaga cagagtcacc     60

atcacttgcc gggcaagtca gggcattaga aatgagttag gctggtatca gcagaaacca    120

gggaaagccc ctaagctcct gatctatgct gcatccagtt tgcaaagtgg ggtcccatca    180

aggttcagcg gcagtggatc tgggacagat ttcactctca cattcagcag cctgcagcct    240

gaagattttg caacttacta ttgttcacag gataacaatt tcccgtggac gtttggccaa    300

gggaccaagg tggaaatcaa a                                              321


<210> SEQ ID NO 520
<211> LENGTH: 107
<212> TYPE: PRT
<213> ORGANISM: Artificial Sequence
<220> FEATURE:
<223> OTHER INFORMATION: Synthetic

<400> SEQUENCE: 520

Asp Ile Val Met Thr Gln Ser Pro Ser Ser Leu Ser Ala Ser Val Arg
 1               5                  10                  15

Asp Arg Val Thr Ile Thr Cys Arg Ala Ser Gln Gly Ile Arg Asn Glu
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Phe Ser Ser Leu Gln Pro
65                  70                  75                  80

Glu Asp Phe Ala Thr Tyr Tyr Cys Ser Gln Asp Asn Asn Phe Pro Trp
                85                  90                  95

Thr Phe Gly Gln Gly Thr Lys Val Glu Ile Lys
            100                 105


<210> SEQ ID NO 521
<211> LENGTH: 18
<212> TYPE: DNA
<213> ORGANISM: Artificial Sequence
<220> FEATURE:
<223> OTHER INFORMATION: Synthetic

<400> SEQUENCE: 521

cagggcatta gaaatgag                                                   18


<210> SEQ ID NO 522
<211> LENGTH: 6
<212> TYPE: PRT
<213> ORGANISM: Artificial Sequence
<220> FEATURE:
<223> OTHER INFORMATION: Synthetic

<400> SEQUENCE: 522

Gln Gly Ile Arg Asn Glu
 1               5


<210> SEQ ID NO 523
<211> LENGTH: 9
<212> TYPE: DNA
<213> ORGANISM: Artificial Sequence
<220> FEATURE:
<223> OTHER INFORMATION: Synthetic

<400> SEQUENCE: 523

gctgcatcc                                                              9
```

<210> SEQ ID NO 524
<211> LENGTH: 3
<212> TYPE: PRT
<213> ORGANISM: Artificial Sequence
<220> FEATURE:
<223> OTHER INFORMATION: Synthetic

<400> SEQUENCE: 524

Ala Ala Ser
1

<210> SEQ ID NO 525
<211> LENGTH: 27
<212> TYPE: DNA
<213> ORGANISM: Artificial Sequence
<220> FEATURE:
<223> OTHER INFORMATION: Synthetic

<400> SEQUENCE: 525
tcacaggata acaatttccc gtggacg 27

<210> SEQ ID NO 526
<211> LENGTH: 9
<212> TYPE: PRT
<213> ORGANISM: Artificial Sequence
<220> FEATURE:
<223> OTHER INFORMATION: Synthetic

<400> SEQUENCE: 526

Ser Gln Asp Asn Asn Phe Pro Trp Thr
1 5

<210> SEQ ID NO 527
<211> LENGTH: 357
<212> TYPE: DNA
<213> ORGANISM: Artificial Sequence
<220> FEATURE:
<223> OTHER INFORMATION: Synthetic

<400> SEQUENCE: 527
caggtgcagc tggtgcagtc cggcgccgag gtgaagaagc ccggcgcctc cgtgaaggtg 60
tcctgcaagg tgtccggcta caccctgacc gagctgtcca tgcactgggt gcggcaggcc 120
cccggcaagg gcctggagtg gatgggcggc ttcgaccccg agcacggcac caccatctac 180
gcccagaagt tccagggccg ggtgaccatg accgaggaca cctccaccga caccgcctac 240
atggagctgt cctccctgcg gtccgaggac accgccgtgt actactgcgt gatgatcttc 300
ggcgtggtga ccaacttcga caactggggc cagggcaccc tggtgaccgt gtcctcc 357

<210> SEQ ID NO 528
<211> LENGTH: 119
<212> TYPE: PRT
<213> ORGANISM: Artificial Sequence
<220> FEATURE:
<223> OTHER INFORMATION: Synthetic

<400> SEQUENCE: 528

Gln Val Gln Leu Val Gln Ser Gly Ala Glu Val Lys Lys Pro Gly Ala
1 5 10 15

Ser Val Lys Val Ser Cys Lys Val Ser Gly Tyr Thr Leu Thr Glu Leu
20 25 30

Ser Met His Trp Val Arg Gln Ala Pro Gly Lys Gly Leu Glu Trp Met
35 40 45

```
Gly Gly Phe Asp Pro Glu His Gly Thr Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Met Ile Phe Gly Val Val Thr Asn Phe Asp Asn Trp Gly Gln Gly
            100                 105                 110

Thr Leu Val Thr Val Ser Ser
        115


<210> SEQ ID NO 529
<211> LENGTH: 321
<212> TYPE: DNA
<213> ORGANISM: Artificial Sequence
<220> FEATURE:
<223> OTHER INFORMATION: Synthetic

<400> SEQUENCE: 529

gacatccaga tgacccagtc cccctcctcc ctgtccgcct ccgtgggcga ccgggtgacc     60

atcacctgcc gggcctccca gggcatccgg aacgagctgg gctggtacca gcagaagccc    120

ggcaaggccc ccaagcggct gatctacgcc gcctcctccc tgcagtccgg cgtgccctcc    180

cggttctccg gctccggctc cggcaccgag ttcaccctga ccatctcctc cctgcagccc    240

gaggacttcg ccacctacta ctgctcccag gacaacaact tcccctggac cttcggccag    300

ggcaccaagg tggagatcaa g                                              321


<210> SEQ ID NO 530
<211> LENGTH: 107
<212> TYPE: PRT
<213> ORGANISM: Artificial Sequence
<220> FEATURE:
<223> OTHER INFORMATION: Synthetic

<400> SEQUENCE: 530

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Glu
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Ser Gln Asp Asn Asn Phe Pro Trp
                85                  90                  95

Thr Phe Gly Gln Gly Thr Lys Val Glu Ile Lys
            100                 105


<210> SEQ ID NO 531
<211> LENGTH: 357
<212> TYPE: DNA
<213> ORGANISM: Artificial Sequence
<220> FEATURE:
<223> OTHER INFORMATION: Synthetic

<400> SEQUENCE: 531

caggtgcagc tggtgcagtc tggggctgat gtgaagaagc ctggggcctc agtgaaggtc     60
```

```
tcctgcaagg tttccggata caccctcact gaattatcca tacactgggt gcgacaggct    120

cctggaaaag ggcttgaatg gatgggaggt tttgatcctg aacatggtac aacaatctac    180

gcacagaagt tccagggcag agtcaccatg accgaggaca catctacaga cacagcctac    240

atggagctga gcagcctgag atctgaggac acggccgtgt attactgtgt aatgattttt    300

ggcgtggtta ccaattttga caactggggc cagggaaccc tggtcaccgt ctcctca       357
```

<210> SEQ ID NO 532
<211> LENGTH: 119
<212> TYPE: PRT
<213> ORGANISM: Artificial Sequence
<220> FEATURE:
<223> OTHER INFORMATION: Synthetic

<400> SEQUENCE: 532

```
Gln Val Gln Leu Val Gln Ser Gly Ala Asp Val Lys Lys Pro Gly Ala
 1               5                  10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu His Gly Thr Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Met Ile Phe Gly Val Val Thr Asn Phe Asp Asn Trp Gly Gln Gly
            100                 105                 110

Thr Leu Val Thr Val Ser Ser
        115
```

<210> SEQ ID NO 533
<211> LENGTH: 321
<212> TYPE: DNA
<213> ORGANISM: Artificial Sequence
<220> FEATURE:
<223> OTHER INFORMATION: Synthetic

<400> SEQUENCE: 533

```
gacatccaga tgacccagtc tccatcctcc ctgtctgcat ccgtgagaga cagagtcacc     60

atcacttgcc gggcaagtca gggcattaga aatgagttag gctggtatca gcagaaacca    120

gggaaagccc ctaagctcct gatctatgct gcatccagtt tgcaaagtgg ggtcccatca    180

aggttcagcg gcagtggatc tgggacagat ttcactctca cattcagcag cctgcagcct    240

gaagattttg caacttacta ttgttcacag gataacaatt tcccgtggac gtttggccaa    300

gggaccaagg tggaaatcaa a                                              321
```

<210> SEQ ID NO 534
<211> LENGTH: 107
<212> TYPE: PRT
<213> ORGANISM: Artificial Sequence
<220> FEATURE:
<223> OTHER INFORMATION: Synthetic

<400> SEQUENCE: 534

```
Asp Ile Gln Met Thr Gln Ser Pro Ser Ser Leu Ser Ala Ser Val Arg
 1               5                  10                  15

Asp Arg Val Thr Ile Thr Cys Arg Ala Ser Gln Gly Ile Arg Asn Glu
```

```
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Phe Ser Ser Leu Gln Pro
65                  70                  75                  80

Glu Asp Phe Ala Thr Tyr Tyr Cys Ser Gln Asp Asn Asn Phe Pro Trp
                85                  90                  95

Thr Phe Gly Gln Gly Thr Lys Val Glu Ile Lys
            100                 105


<210> SEQ ID NO 535
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(8)
<223> OTHER INFORMATION: Xaa = Any Amino Acid

<400> SEQUENCE: 535

Xaa Xaa Xaa Xaa Xaa Xaa Xaa Xaa
 1               5


<210> SEQ ID NO 536
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(8)
<223> OTHER INFORMATION: Xaa = Any Amino Acid

<400> SEQUENCE: 536

Xaa Xaa Xaa Xaa Xaa Xaa Xaa Xaa
 1               5


<210> SEQ ID NO 537
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(18)
<223> OTHER INFORMATION: Xaa = Any AMino Acid

<400> SEQUENCE: 537

Xaa Xaa Xaa Xaa Xaa Xaa Xaa Xaa Xaa Xaa Xaa Xaa Xaa Xaa Xaa Xaa
 1               5                  10                  15

Xaa Xaa


<210> SEQ ID NO 538
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(6)
```

<223> OTHER INFORMATION: Xaa = Any Amino Acid

<400> SEQUENCE: 538

```
Xaa Xaa Xaa Xaa Xaa Xaa
 1              5
```

<210> SEQ ID NO 539
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(3)
<223> OTHER INFORMATION: Xaa = Any Amino Acid

<400> SEQUENCE: 539

```
Xaa Xaa Xaa
 1
```

<210> SEQ ID NO 540
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(9)
<223> OTHER INFORMATION: Xaa = Any Amino Acid

<400> SEQUENCE: 540

```
Xaa Xaa Xaa Xaa Xaa Xaa Xaa Xaa Xaa
 1              5
```

<210> SEQ ID NO 541
<211> LENGTH: 330
<212> TYPE: PRT
<213> ORGANISM: Artificial Sequence
<220> FEATURE:
<223> OTHER INFORMATION: Synthetic

<400> SEQUENCE: 541

```
Ala Ser Thr Lys Gly Pro Ser Val Phe Pro Leu Ala Pro Ser Ser Lys
 1              5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 542
<211> LENGTH: 327
<212> TYPE: PRT
<213> ORGANISM: Artificial Sequence
<220> FEATURE:
<223> OTHER INFORMATION: Synthetic

<400> SEQUENCE: 542

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 543
<211> LENGTH: 327
<212> TYPE: PRT
<213> ORGANISM: Artificial Sequence
<220> FEATURE:
<223> OTHER INFORMATION: Synthetic

<400> SEQUENCE: 543

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220
```

-continued

```
Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

HIGH AFFINITY HUMAN ANTIBODIES TO HUMAN NERVE GROWTH FACTOR

CROSS-REFERENCE TO RELATED APPLICATIONS

This application is a Divisional of U.S. patent application Ser. No. 12/188,330, filed Aug. 8, 2008, which claims the benefit under 35 USC §119(e) of U.S. Provisional 60/964,224 filed 10 Aug. 2007, 60/994,526 filed 20 Sep. 2007, 61/062,860 filed 28 Jan. 2008, and 61/079,259 filed 9 Jul. 2008, which applications are herein specifically incorporated by reference in their entirety.

FIELD OF THE INVENTION

The present invention is related to human antibodies and antigen-binding fragments of human antibodies that specifically bind human nerve growth factor (NGF), and therapeutic methods of using those antibodies.

STATEMENT OF RELATED ART

Nerve growth factor (NGF) was the first neurotrophin to be identified, and its role in the development and survival of both peripheral and central neurons has been well characterized. NGF has been shown to be a critical survival and maintenance factor in the development of peripheral sympathetic and embryonic sensory neurons and of basal forebrain cholinergic neurons (Smeyne et al. (1994) Nature 368:246-249; Crowley et al. (1994) Cell 76:1001-1011). NGF upregulates expression of neuropeptides in sensory neurons (Lindsay et al. (1989) Nature 337:362-364) and its activity is mediated through two different membrane-bound receptors, the TrkA receptor and the p75 common neurotrophin receptor.

NGF is elevated in synovial fluid in patients suffering from rheumatoid arthritis and other types of arthritis. NGF antagonists have been shown to prevent hyperalgesia and allodynia in animal models of neuropathic and chronic inflammatory pain.

Anti-NGF antibodies are described in, for example, WO 01/78698, WO 02/096458, WO 2004/032870, US patent application publications 2005/0074821, 2004/0237124, and 2004/0219144.

BRIEF SUMMARY OF THE INVENTION

In a first aspect, the invention provides fully human antibodies and antigen-binding fragments thereof that specifically bind human nerve growth factor (NGF) with a $K_D$ of about 5 pM or less. In a preferred embodiment, the anti-NGF antibody or fragment thereof binds human NGF with a $K_D$ of 1.0 pM or less. These antibodies are characterized by binding to NGF with high affinity, high specificity and by the ability to neutralize NGF activity. In preferred embodiments, the antibody or fragment thereof binds human NGF about 2-10 fold higher than rat NGF and/or mouse NGF.

The antibodies can be full-length (for example, an IgG1 or IgG4 antibody) or may comprise only an antigen-binding portion (for example, a Fab, $F(ab')_2$ or scFv fragment), and may be modified to effect functionality, e.g., to eliminate residual effector functions (Glu which eliminates residual effector functions (Reddy et al. (2000) J. Immunol. 164:1925-1933).

In one embodiment, the invention comprises an antibody or antigen-binding fragment of an antibody comprising a heavy chain variable region (HCVR) selected from the group consisting of SEQ ID NO:4, 20, 36, 52, 68, 84, 100, 104, 108, 112, 116, 132, 136, 140, 156, 160, 176, 180, 184, 200, 204, 208, 224, 228, 232, 236, 240, 256, 260, 264, 280, 284, 288, 304, 308, 312, 328, 332, 336, 352, 356, 360, 376, 380, 384, 400, 404, 420, 424, 440, 456, 460, 464, 480, 484, 488, 504, 508, 512, 528 and 532 or a substantially similar sequence thereof having at least 90%, at least 95%, at least 98% or at least 99% sequence identity. In a preferred embodiment, the antibody or antigen-binding portion of an antibody comprises a HCVR having an amino acid sequence selected from the group consisting of SEQ ID NO:84, 100 and 108.

In one embodiment, the antibody or fragment thereof further comprises a light chain variable region (LCVR) selected from the group consisting of SEQ ID NO:12, 28, 44, 60, 76, 92, 102, 106, 110, 114, 124, 134, 138, 148, 158, 168, 178, 182, 192, 202, 206, 216, 226, 230, 234, 238, 248, 258, 262, 272, 282, 286, 296, 306, 310, 320, 330, 334, 344, 354, 358, 368, 378, 382, 392, 402, 412, 422, 432, 448, 458, 462, 472, 482, 486, 496, 506, 510, 520, 530, and 534, or a substantially similar sequence thereof having at least 90%, at least 95%, at least 98% or at least 99% sequence identity. In a preferred embodiment, the antibody or antigen-binding portion of an antibody comprises a LCVR having an amino acid sequence selected from the group consisting of SEQ ID NO:92, 102 and 110.

In specific embodiments, the antibody or fragment thereof comprises a HCVR and LCVR (HCVR/LCVR) sequence pair selected from the group consisting of SEQ ID NO:4/12, 20/28, 36/44, 52/60, 68/76, 84/92, 100/102, 104/106, 108/110, 112/114, 116/124, 132/134, 136/138, 140/148, 156/158, 160/168, 176/178, 180/182, 184/192, 200/202, 204/206, 208/216, 224/226, 228/230, 232/234, 236/238, 240/248, 256/258, 260/262, 264/272, 280/282, 284/286, 288/296, 304/306, 308/310, 312/320, 328/330, 332/334, 336/344, 352/354, 356/358, 360/368, 376/378, 380/382, 384/392, 400/402, 404/412, 420/422, 424/432, 440/448, 456/458, 460/462, 464/472, 480/482, 484/486, 488/496, 504/506, 508/510, 512/520, 528/530 and 532/534. In a preferred embodiment, the antibody or fragment thereof comprises a HCVR and LCVR selected from the amino acid sequence pairs of SEQ ID NO:84 and 92; 100 and 102; and 108 and 110.

In a second aspect, the invention features an antibody or antigen-binding fragment of an antibody comprising a heavy chain CDR3 (HCDR3) domain selected from the group consisting of SEQ ID NO:10, 26, 42, 58, 74, 90, 122, 146, 166, 190, 214, 246, 270, 294, 318, 342, 366, 390, 410, 430, 446, 470, 494 and 518, or a substantially similar sequence thereof having at least 90%, at least 95%, at least 98% or at least 99% sequence identity; and a light chain CDR3 (LCDR3) domain selected from the group consisting of 18, 34, 50, 66, 82, 98, 130, 154, 174, 198, 222, 254, 278, 302, 326, 350, 374, 398, 418, 438, 454, 478, 502 and 526, or substantially similar sequences thereof having at least 90%, at least 95%, at least 98% or at least 99% sequence identity. In a preferred embodiment, the antibody or antigen-binding portion of an antibody comprises HCDR3 and LCDR3 sequences SEQ ID NO:90 and 98; 214 and 222; 410 and 418; 430 and 438; or 446 and 454.

In a further embodiment, the invention comprises an antibody or fragment thereof further comprising a heavy chain CDR1 (HCDR1) domain selected from the group consisting of SEQ ID NO:6, 22, 38, 54, 70, 86, 118, 142, 162, 186, 210, 242, 266, 290, 314, 338, 362, 386, 406, 426, 442, 466, 490, and 514, or a substantially similar sequence thereof having at least 90%, at least 95%, at least 98% or at least 99% sequence identity. a heavy chain CDR2 (HCDR2) domain selected from the group consisting of SEQ ID NO:8, 24, 40, 56, 72, 88, 120, 144, 164, 188, 212, 244, 268, 292, 316, 340, 364, 388, 408, 428, 444, 468, 492 and 516 or a substantially similar sequence thereof having at least 90%, at least 95%, at least 98% or at least 99% sequence identity; a light chain CDR1 (LCDR1) domain selected from the group consisting of SEQ ID NO:14, 30, 46, 62, 78, 94, 126, 150, 170, 194, 218, 250, 274, 298, 322, 346, 370, 394, 414, 434, 450, 474, 498, and 522, or a substantially similar sequence thereof having at least 90%, at least 95%, at least 98% or at least 99% sequence identity; and a light chain CDR2 (LCDR2) domain selected from the group consisting of SEQ ID NO:16, 32, 48, 64, 80, 96, 128, 152, 172, 196, 220, 252, 276, 300, 324, 348, 372, 396, 416, 436, 452, 476, 500 and 524, or a substantially similar sequence thereof having at least 90%, at least 95%, at least 98% or at least 99% sequence identity. In a preferred embodiment, the antibody or antigen-binding portion of an antibody comprises heavy and light chain CDR sequences SEQ ID NO:86, 88, 90, 94, 96 and 98; 210, 212, 214, 218, 220 and 222; 406, 408, 410, 414, 416 and 418; 442, 444, 446, 450, 452 and 454; and 426, 428, 430, 434, 436 and 438. Preferably, the antibody or fragment thereof comprises CDR sequences SEQ ID NO: 86, 88, 90, 94, 96 and 98.

In a third aspect, the invention provides nucleic acid molecules encoding anti-NGF antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and methods of recovering the antibodies produced.

In one embodiment, the invention provides an antibody or fragment thereof comprising a HCVR encoded by a nucleic acid sequence selected from the group consisting of SEQ ID NO:3, 19, 35, 51, 67, 83, 99, 103, 107, 111, 115, 131, 135, 139, 155, 159, 175, 179, 183, 199, 203, 207, 223, 227, 231, 235, 239, 255, 259, 263, 279, 283, 287, 303, 307, 311, 327, 331, 335, 351, 355, 359, 375, 379, 383, 399, 403, 419, 423, 439, 455, 459, 463, 479, 483, 487, 503, 507, 511, 527 and 531, or a substantially identical sequence having at least 90%, at least 95%, at least 98%, or at least 99% homology thereof. In a preferred embodiment, the antibody or fragment thereof comprises a HCVR encoded by a nucleic acid sequence selected from the group consisting of SEQ ID NO:83, 99 and 107.

In one embodiment, the antibody or fragment thereof further comprises a LCVR encoded by a nucleic acid sequence selected from the group consisting of SEQ ID NO:11, 27, 43, 59, 75, 91, 101, 105, 109, 113, 123, 133, 137, 147, 157, 167, 177, 181, 191, 201, 205, 215, 225, 229, 233, 237, 247, 257, 261, 271, 281, 285, 295, 305, 309, 319, 329, 333, 343, 353, 357, 367, 377, 381, 391, 401, 411, 421, 431, 447, 457, 461, 471, 481, 485, 495, 505, 509, 519, 529 and 533, or a substantially identical sequence having at least 90%, at least 95%, at least 98%, or at least 99% homology thereof. In a preferred embodiment, the antibody or fragment thereof comprises an LCVR encoded by a nucleic acid sequence selected from the group consisting of SEQ ID NO:91, 101 and 109.

In one embodiment, the invention features an antibody or antigen-binding fragment of an antibody comprising a HCDR3 domain encoded by a nucleotide sequence selected from the group consisting of SEQ ID NO:9, 25, 41, 57, 73, 89, 121, 145, 165, 189, 213, 245, 269, 293, 317, 341, 365, 389, 409, 429, 445, 469, 493 and 517, or a substantially identical sequence having at least 90%, at least 95%, at least 98%, or at least 99% homology thereof; and a LCDR3 domain encoded by a nucleotide sequence selected from the group consisting of SEQ ID NO: 17, 33, 49, 65, 81, 97, 129, 153, 173, 197, 221, 253, 277, 301, 325, 349, 373, 397, 417, 437, 453, 477, 501 and 525, or a substantially identical sequence having at least 90%, at least 95%, at least 98%, or at least 99% homology thereof. In a preferred embodiment, the antibody or fragment thereof comprises an HCDR3 and LCDR3 sequences encoded by the nucleic acid sequence of SEQ ID NO:89 and 97, respectively.

In another embodiment, the antibody or fragment thereof further comprises, a HCDR1 domain encoded by a nucleotide sequence selected from the group consisting of SEQ ID NO:5, 21, 37, 53, 69, 85, 117, 141, 161, 185, 209, 241, 265, 289, 313, 337, 361, 385, 405, 425, 441, 465, 489 and 513, or a substantially identical sequence having at least 90%, at least 95%, at least 98%, or at least 99% homology thereof; a HCDR2 domain encoded by a nucleotide sequence selected from the group consisting of SEQ ID NO:7, 23, 39, 55, 71, 87, 119, 143, 163, 187, 211, 243, 267, 291, 315, 339, 363, 387, 407, 427, 443, 467, 491 and 515, or a substantially identical sequence having at least 90%, at least 95%, at least 98%, or at least 99% homology thereof; a LCDR1 domain encoded by a nucleotide sequence selected from the group consisting of SEQ ID NO:13, 29, 45, 61, 77, 93, 125, 149, 169, 193, 217, 249, 273, 297, 321, 345, 369, 393, 413, 433, 449, 473, 497 and 521, or a substantially identical sequence having at least 90%, at least 95%, at least 98%, or at least 99% homology thereof; and a LCDR2 domain encoded by a nucleotide sequence selected from the group consisting of SEQ ID NO:15, 31, 47, 63, 79, 95, 127, 151, 171, 195, 219, 251, 275, 299, 323, 347, 371, 395, 415, 435, 451, 475, 499 and 523, or a substantially identical sequence having at least 90%, at least 95%, at least 98%, or at least 99% homology thereof. In a preferred embodiment, the antibody or fragment thereof comprises heavy chain CDR sequences encoded by the nucleic acid sequences of SEQ ID NO:85, 87, and 89, respectively; and light chain CDR sequences encoded by the nucleic acid sequences of SEQ ID NO:93, 95 and 97, respectively.

In a fourth aspect, the invention features an isolated antibody or antigen-binding fragment of an antibody that specifically binds human NGF, comprising a HCDR3 and a LCDR3, wherein the HCDR3 comprises an amino acid sequence of the formula $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$ (SEQ ID NO:537) wherein $X^1$ is Ala or Ser, $X^2$ is Thr or Lys, $X^3$ is Glu or Ile, $X^4$ is Phe or Gly, $X^5$ is Val or Gly, $X^6$ is Val or Trp, $X^7$ is Val or Phe, $X^8$ is Thr or Gly, $X^9$ is Asn or Lys, $X^{10}$ is Phe or Leu, $X^{11}$ is Asp or Phe, $X^{12}$ is Asn or Ser, $X^{13}$ is Ser or absent, $X^{14}$ is Tyr or absent, $X^{15}$ is Gly or absent, $X^{16}$ is Met or absent, $X^{17}$ is Asp or absent, and $X^{18}$ is Val or absent; and the LCDR3 comprises an amino acid sequence of the formula $X^1$-$X^2$-$X^3$-$X^4$-$X^5$-$X^6$-$X^7$-$X^8$-$X^9$ (SEQ ID NO:540) wherein $X^1$ is Gln, $X^2$ is Gln, $X^3$ is Tyr, $X^4$ is Asn, $X^5$ is Arg or Asn, $X^6$ is Tyr or Trp, $X^7$ is Pro, $X^8$ is Tyr or Trp, and $X^9$ is Thr.

In another embodiment, the invention features an isolated antibody or fragment thereof that specifically binds human NGF, comprising a HCDR1 sequence of the formula $X^1$-$X^2$-$X^3$-$X^4$-$X^5$-$X^6$-$X^7$-$X^8$ (SEQ ID NO:535), wherein $X^1$ is Gly, $X^2$ is Phe, $X^3$ is Thr or Asn, $X^4$ is Phe or Leu, $X^5$ is Thr or Asp, $X^6$ is Asp or Glu, $X^7$ is Tyr or Leu, and $X^8$ is Ser or Ala; a HCDR2 sequence of the formula $X^1$-$X^2$-$X^3$-$X^4$-$X^5$-$X^6$-$X^7$-$X^8$ (SEQ ID NO:536), wherein $X^1$ is Ile or Phe, $X^2$ is Asp or Ser, $X^3$ is Pro or Trp, $X^4$ is Glu or Asn, $X^5$ is Asp or Ser, $X^6$ is Gly, $X^7$ is Thr, Glu or Ser, $X^8$ is Thr or Ile; a HCDR3 comprises an amino acid sequence of the formula $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$ (SEQ ID NO:537) wherein $X^1$ is Ala or Ser, $X^2$ is Thr or Lys, $X^3$ is Glu or Ile, $X^4$ is Phe or Gly, $X^5$ is Val or Gly, $X^6$ is Val or Trp, $X^7$ is Val or Phe, $X^8$ is Thr or Gly, $X^9$ is Asn or Lys, $X^{10}$ is Phe or Leu, $X^{11}$ is Asp or Phe, $X^{12}$ is Asn or Ser, $X^{13}$ is Ser or absent, $X^{14}$ is Tyr or absent, $X^{15}$ is Gly or absent, $X^{16}$ is Met or absent, $X^{17}$ is Asp or absent, and $X^{18}$ is Val or absent; a LCDR1 sequence of the formula $X^1$-$X^2$-$X^3$-$X^4$-$X^5$-$X^6$ (SEQ ID NO:538) wherein $X^1$ is Gln or Arg, $X^2$ is Ala, Ser or Thr, $X^3$ is Val or Ile, $X^4$ is Arg or Thr, $X^5$ is Asn, Phe or Tyr, and $X^6$ is Asp or Asn; a LCDR2 sequence of the formula $X^1$-$X^2$-$X^3$ (SEQ ID NO:539) wherein $X^1$ is Gly or Ala, $X^2$ is Ala, and $X^3$ is Ser or Phe; and a LCDR3 comprises an amino acid sequence of the formula $X^1$-$X^2$-$X^3$-$X^4$-$X^5$-$X^6$-$X^7$-$X^8$-$X^9$ (SEQ ID NO:540) wherein $X^1$ is Gln, $X^2$ is Gln, $X^3$ is Tyr, $X^4$ is Asn, $X^5$ is Arg or Asn, $X^6$ is Tyr or Trp, $X^7$ is Pro, $X^8$ is Tyr or Trp, and $X^9$ is Thr.

In a fifth aspect, the invention features a fully human antibody or antibody fragment which blocks NGF activity with an $IC_{50}$ of less than about 10 nM, as measured in in vitro PC12 cell-based assay (described below). In a preferred embodiment, the antibody of the invention exhibits an $IC_{50}$ of about 500 pM or less. In an even more preferred embodiment, the antibody of the invention exhibits an $IC_{50}$ of about 100 pM or less; about 50 pM or less; or about 25 pM or less. In one embodiment, the invention provides an isolated human antibody, or an antigen-binding portion thereof, that binds NGF with a $K_D$ of less than about 500 pM, preferably less than about 300 pM, even more preferably less than about 100 pM, less than about 50 pM, less than about 20 pM; less than about 10 pM, less than about 5 pM, or less than about 1 pM, as determined by surface plasmon resonance (BIACORE™). In a preferred embodiment, the anti-NGF human antibody or antibody fragment of the invention binds human NGF with a $K_D$ of about 0.5 pM or less. In preferred embodiments, the antibody or fragment thereof binds human NGF about 1.5-fold, 2-fold, 3-fold, 4-fold, 5-fold, 6-fold, 7-fold, 8-fold, 9-fold or 10-fold higher affinity than rat NGF and about 1.5-fold, 2-fold, 2.5-fold, 3-fold, 4-fold, 5-fold, 6-fold, 7-fold, 8-fold, 9-fold, or 10-fold higher than mouse NGF.

In one embodiment, the antibody or fragment thereof exhibits high specificity for human NGF, for example, does not cross-reacting with closely related neurotrophin-3 (NT-3). Thus, in a preferred embodiment, the high affinity and high selectivity antibody or fragment thereof exhibits a $K_D$ for human NGF of 1.0 pM or less, inhibits binding of NGF to receptors TrkA and p75, and does not cross-react with human NT-3, as measured by surface plasmon resonance. NT-3 plays a critical role in such physiological processes as, for example, muscle motor neuron coordination, and thus, antibodies or antibody fragments that do not cross-react with NT-3 provide an unexpected clinical and therapeutic advantage over prior art antibodies. NT-3 has been shown to prevent the development of thermal hyperalgesia in the CCl model of neuropathic pain (see, for example, Wilson-Gerwing et al. (2005) J Neuroscience 25:758-767). More recently, exogenous NT-3 has been shown to significantly decrease expression of two sodium channels which appear to play a role in the generation of neuropathic pain (Wilson-Gerwing & Verge (2006) Neuroscience 141:2075-2085. These data suggest a beneficial role of NT-3 in neuropathic pain.

The invention encompasses anti-NGF antibodies having a modified glycosylation pattern. In some applications, modification to remove undesirable glycosylation sites may be used, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In a sixth aspect, the invention features a composition comprising a recombinant human antibody or fragment thereof which specifically binds NGF and an acceptable carrier. In a related aspect, the invention features a composition which is a combination of an NGF inhibitor and a second therapeutic agent. In one embodiment, the NGF inhibitor is an antibody or fragment thereof. In a preferred embodiment, the second therapeutic agent is any agent that is advantageously combined with an NGF inhibitor, without limitation.

In a seventh aspect, the invention features methods for inhibiting human NGF activity using the anti-NGF antibody or antigen-binding portion of the antibody of the invention. The disorder treated is any disease or condition which is improved, ameliorated, inhibited or prevented by removal, inhibition or reduction of NGF activity. More specifically, the invention provides a method of treating an NGF-related condition or disease such as inflammatory pain, post-operative incision pain, complex regional pain syndrome, primary or metastatic bone cancer pain, neuropathic pain, fracture pain, osteoporotic fracture pain, pain resulting from burn, osteoporosis, gout joint pain, pains associated with sickle cell crises, and other nociceptic pains, as well as pain associated with hepatocellular carcinoma, breast cancer, and liver cirrhosis, by administering an NGF inhibitor, such as the antibody or antibody fragment of the invention, as a single agent, or with a second therapeutic agent. In preferred embodiments of neuropathic pain, referred trigeminal neuralgia, post-herpetic neuralgia, phantom limb pain, fibromyalgia, reflex sympathetic dystrophy and neurogenic pain conditions are preferably treated. The second therapeutic agent may be an interleukin-1 (IL-1) inhibitor, for example, a fusion protein (U.S. Pat. No. 6,927,044); or an antiepileptic drug, such as gabapentain, pregabalin, topiramate; or a tricyclic antidepressant, such as amitriptyline; celecoxib; a cytokine antagonist, such as an antagonist to IL-1, IL-6, IL-6R, IL-18 or IL-18R. In one embodiment, the second therapeutic agent is another neurotrophin, for example, NT-3. Other objects and advantages will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

DEFINITIONS

The term "human nerve growth factor" or "NGF", as used herein, refers to human NGF having the nucleic acid sequence shown in SEQ ID NO:1 and the amino acid sequence of SEQ ID NO:2, or a biologically active fragment thereof.

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "high affinity" antibody refers to those antibodies having a binding affinity to NGF of at least $10^{-9}$ M; preferably $10^{-10}$ M; even more preferably $10^{-11}$ M, as measured by surface plasmon resonance, e.g., BIACORE™ or solution-affinity ELISA.

By the term "slow off rate" or "Koff" is meant an antibody that dissociates from NGF with a rate constant of $1\times10^{-3}$ $s^{-1}$ or less, preferably $1\times10^{-4}$ $s^{-1}$ or less, as determined by surface plasmon resonance, e.g., BIACORE™.

The term "antigen-binding portion" of an antibody (or simply "antibody portion" or "antibody fragment"), as used herein, refers to one or more fragments of an antibody that retain the ability to specifically bind to an antigen (e.g., NGF). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) Proc. Natl. Acad. Sci. USA 90:6444-6448; Poljak et al. (1994) Structure 2:1121-1123).

Still further, an antibody or antigen-binding portion thereof may be part of larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov et al. (1995) Human Antibodies and Hybridomas 6:93-101) and use of a cysteine residue, a marker peptide and a C-terminal polyhistidine tag to make bivalent and biotinylated scFv molecules (Kipriyanov et al. (1994) Mol. Immunol. 31:1047-1058). Antibody portions, such as Fab and $F(ab')_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

An "isolated antibody", as used herein, is intended to refer to an antibody that is substantially free of other antibodies having different antigenic specificities (e.g., an isolated antibody that specifically binds NGF is substantially free of antibodies that specifically bind antigens other than NGF). An isolated antibody that specifically binds NGF may, however, have cross-reactivity to other antigens, such as NGF molecules from other species. Moreover, an isolated antibody may be substantially free of other cellular material and/or chemicals.

A "neutralizing antibody", as used herein (or an "antibody that neutralizes NGF activity"), is intended to refer to an antibody whose binding to NGF results in inhibition of the biological activity of NGF. This inhibition of the biological activity of NGF can be assessed by measuring one or more indicators of NGF biological activity, such as NGF-induced cellular activation and NGF binding to NGF receptor. These indicators of NGF biological activity can be assessed by one or more of several standard in vitro or in vivo assays known in the art (see examples below).

A "CDR" or complementarity determining region is a region of hypervariability interspersed with regions that are more conserved, termed "framework regions". A group of CDRs may be defined as an amino acid consensus sequence.

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "isolated nucleic acid molecule", as used herein in reference to nucleic acids encoding antibodies or antibody portions (e.g., VH, VL, CDR3) that bind NGF is intended to refer to a nucleic acid molecule in which the nucleotide sequences encoding the antibody or antibody portion are free of other nucleotide sequences encoding antibodies or antibody portions that bind antigens other than NGF, which other sequences may naturally flank the nucleic acid in human genomic DNA. Thus, for example, an isolated nucleic acid of the invention encoding a VH region of an anti-NGF antibody contains no other sequences encoding other VH regions that bind antigens other than human NGF.

The term "epitope" includes any determinant, preferably a polypeptide determinant, capable of specific binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. In preferred embodiments, an antibody is said to specifically bind an antigen when the equilibrium dissociation constant is less than or equal to $10^{-8}$ M, more preferably when the equilibrium dissociation constant is less than or equal to $10^{-9}$ M, and most preferably when the dissociation constant is less than or equal to $10^{-10}$ M.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403 410 and Altschul et al. (1997) Nucleic Acids Res. 25:3389 402, each of which is herein incorporated by reference.

Preparation of Human Antibodies

Methods for generating human antibodies include, for example, VELOCIMMUNE™, XENOMOUSE™ technology (Green et al. (1994) Nature Genetics 7:13-21), the "minilocus" approach, and phage display. The VELOCIMMUNE™ technology (U.S. Pat. No. 6,596,541, Regeneron Pharmaceuticals) encompasses a method of generating a high specificity fully human antibody to a select antigen. This technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody. In specific embodiment, the cell is a CHO cell.

Antibodies may be therapeutically useful in blocking a ligand-receptor interaction or inhibiting receptor component interaction, rather than by killing cells through fixation of complement and participation in complement-dependent cytotoxicity (CDC), or killing cells through antibody-dependent cell-mediated cytotoxicity (ADCC). The constant region of an antibody is thus important in the ability of an antibody to fix complement and mediate cell-dependent cytotoxicity. Thus, the isotype of an antibody may be selected on the basis of whether it is desirable for the antibody to mediate cytotoxicity.

Human immunoglobulins can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, CH2 or CH3 region which may be desirable, for example, in production, to improve the yield of the desired antibody form.

Antibodies of the invention are preferably prepared with the use of VELOCIMMUNE™ technology. A transgenic mouse in which the endogenous immunoglobulin heavy and light chain variable regions are replaced with the corresponding human variable regions is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

In general, the antibodies of the instant invention possess very high affinities, typically possessing $K_D$ of from about $10^{-9}$ through about $10^{-12}$ M or higher, for example, at least about $10^{-9}$ M, at least $10^{-10}$ M, at least $10^{-11}$ M or at least $10^{-12}$ M, when measured by binding to antigen either immobilized on solid phase or in solution phase.

Initially, high affinity chimeric antibodies are isolated having a human variable region and a mouse constant region. As described below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4 (for example, SEQ ID NO:541, 542 or 543). While the constant region selected may vary according to specific use, high affinity antigen-binding and target specificity characteristics reside in the variable region.

Epitope Mapping and Related Technologies

To screen for antibodies that bind to a particular epitope (e.g., those which block binding of IgE to its high affinity receptor), a routine cross-blocking assay such as that described in Harlow and Lane (1990) supra can be performed. Other methods include alanine scanning mutants, peptide blots (Reineke (2004) Methods Mol Biol 248:443-63) (herein specifically incorporated by reference in its entirety), or peptide cleavage analysis. In addition, methods such as epitope excision, epitope extraction and chemical modification of antigens can be employed (Tomer (2000) Protein Science 9: 487-496) (herein specifically incorporated by reference in its entirety).

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the anti-NGF antibodies of the invention into groups of antibodies binding different epitopes.

Immunoconjugates

The invention encompasses a human anti-NGF monoclonal antibody conjugated to a therapeutic moiety ("immunoconjugate"), such as a cytotoxin, a chemotherapeutic drug, an immunosuppressant or a radioisotope. Cytotoxin agents include any agent that is detrimental to cells. Examples of suitable cytotoxin agents and chemotherapeutic agents for forming immunoconjugates are known in the art, see for example, WO 05/103081, herein specifically incorporated by reference in its entirety).

Bispecifics

The antibodies of the present invention may be monospecific, bispecific, or multispecific. Multispecific antibodies may be specific for different epitopes of one target polypeptide or may contain antigen-binding domains specific for more than one target polypeptide. See, e.g., Tutt et al. (1991) J. Immunol. 147:60-69. The human anti-NGF antibodies can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment, to produce a bispecific or a multispecific antibody with a second binding specificity.

Therapeutic Administration and Formulations

The invention provides therapeutic compositions comprising the anti-NGF antibodies or antigen-binding fragments thereof of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose may vary depending upon the age and the size of a subject to be administered, target disease, conditions, route of administration, and the like. When the antibody of the present invention is used for treating various conditions and diseases associated with NGF, including inflammatory pain, neuropathic and/or nociceptive pain, hepatocellular carcinoma, breast cancer, liver cirrhosis, and the like, in an adult patient, it is advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.

In certain situations, the pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used (see Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984). Other controlled release systems are discussed in the review by Langer (1990) Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to 500 mg per dosage form in a unit dose; especially in the form of injection, it is preferred that the aforesaid antibody is contained in about 5 to 100 mg and in about 10 to 250 mg for the other dosage forms.

Single and combination therapies. The invention provides therapeutic methods in which the antibody or antibody fragment of the invention is useful to treat pain associated with a variety of conditions involving NGF. The anti-NGF antibodies or antibody fragments of the invention are particularly useful for the treatment of pain resulting from any condition associated with neurogenic, neuropathic or nociceptic pain. In preferred embodiments of neuropathic pain, referred trigeminal neuralgia, post-herpetic neuralgia, phantom limb pain, fibromyalgia, reflex sympathetic dystrophy and neurogenic pain conditions are preferably treated. In other preferred embodiments, cancer pain, particularly, bone cancer pain, osteoarthritis or rheumatoid arthritis pain, lower back pain, post-operative incision pain, fracture pain, osteoporotic fracture pain, osteoporosis, gout joint pain, diabetic neuropathy, sciatica, pains associated with sickle cell crises, migraine, and other neuropathic and/or nociceptic pain are preferably treated.

Other indications include, for example, treatment for breast cancer (Adriaenssens et al. (2008) Cancer Res 68:346-51). In specific embodiments of the therapeutic methods of the invention, a subject suffering from joint pain associated with gout is treated with a combination of an antibody or antibody fragment of the invention and optionally with a second therapeutic agent. In one embodiment, the second therapeutic agent is preferably an interleukin-1 (IL-1) antagonist such as rilonacept ("IL-1 trap"; Regeneron). Suitable second therapeutic agents may be one or more agents selected from the group consisting of rilonacept, anakinra (KINERET®, Amgen), a recombinant, nonglycosylated form of the human IL-1 receptor antagonist or antibody (IL1Ra), an anti-IL-18 drug such as IL-18BP or a derivative, an IL-18 Trap, an antibody such as an anti-IL-18, anti-IL-18R1, anti-IL-18Racp, or anti-IL-6 or anti-IL6Ra antibody or antibody fragment. Other co-therapies which may be combined with an NGF antibody or antigen-binding fragment thereof, alone or in combination with an IL-1 antagonist, include low dose colchine, aspirin or other NSAIDs, steroids such as prednisolone, methotrexate, low dose cyclosporine A, TNF inhibitors such as ENBREL®, or HUMIRA®, other inflammatory inhibitors such as inhibitors of caspase-1, p38, IKK1/2, CTLA-4Ig, etc., and/or co-therapies such as uric acid synthesis inhibitors to inhibit the accumulation of uric acid in the body, for example, allopurinol, uric acid excretion promoters to accelerate the rapid excretion of uric acid accumulated in the body, for example, probenecid, sulfinpyrazone and/or benzbromarone are examples of uric acid excretion promoters; corticosteroids; non-steroidal anti-inflammatory drugs (NSAIDs), anti-epileptic drugs such as topiramate; gabapentin, pregabablin; celecoxib; or another neurotrophin, such as NT-3.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric. The statistical analyses were conducted according to mixed Factorial ANOVA with Bondferroni post hoc or Turkey HSD post hoc tests.

Example 1

Immunization and Antibody Generation

Immunization of rodents can be done by any methods known in the art (see, for example, Harlow and Lane, Antibodies: A Laboratory Manual: Cold Spring Harbor Press, New York; Malik and Lillehoj, Antibody techniques: Academic Press, San Diego). In a preferred embodiment, human NGF protein is administered directly to mice which have DNA loci encoding both human Ig heavy chain variable region and Kappa light chain variable region (VELOCIMMUNE™, Regeneron; U.S. Pat. No. 6,596,541), with an adjuvant to stimulate the immune response. Such an adjuvant includes complete and incomplete Freund's adjuvant, MPL+TDM adjuvant system (Sigma), or RIBI (muramyl dipeptides) (see O'Hagan, Vaccine Adjuvant, Human Press, 2000, Totawa, N.J.). Such an adjuvant can prevent rapid dispersal of polypeptide by sequestering the antigen in a local depot, and may contain factors that can stimulate host immune response. In one embodiment, NGF is administered indirectly as a DNA plasmid that contains NGF gene and expresses NGF using the host cellular protein expression machinery to produce antigen polypeptide in vivo. In both approaches, to obtain optimal anti-antigen responses, mice are given boost injections every 3~4 weeks and serum samples are collected 10 days after each injection. The antibody immune response is monitored using standard antigen direct binding ELISA methods. Post-boost serum samples diluted in 3-fold serial dilutions are applied to NGF coated plates. Serum titer is defined as the dilution of serum sample that yielded two-fold over background signal in the assay. Animals with optimal responses receive a final boost via intravenous and intra-peritoneal injections without an adjuvant 3~4 days prior to sacrifice. The harvested splenocytes are processed as described below in order to obtain antigen specific monoclonal antibodies.

Example 2

Monoclonal Antibody Isolation

In one embodiment, antibody-expressing B cells are fused with mouse myeloma cells to form hybridoma cells. The hybrid cells are plated in 96-well plates under HAT selection and allowed to grow for 10 to 20 days. The conditioned media from wells with growing hybridoma cells are screened for antigen binding and receptor blocking activities as described below. Hybridoma cells expressing antibodies of interest are single-cell sub-cloned using flow cytometry, and VH and VL genes from clonal hybridoma cells cloned and sequenced. Antibody proteins are also purified from cultures of antigen specific hybridomas using IgG depleted medium (Invitrogen) and characterized as described below.

In another embodiment, antigen specific antibodies are isolated directly from antigen positive B cells without being immortalized with specific myeloma cells, and a host CHO cell producing a stable recombinant antibody is generated, as described in U.S. Ser. No. 11/809,482 (US patent Publication No. 2007/0280945, herein specifically incorporated by reference in its entirety).

Example 3

Primary Antigen Binding and Receptor Blocking Screening

To identify antigen specific antibody producing hybridomas, conditioned media were sampled from 96-well culture plates 10 to 20 days after fusion, and antigen binding specificity determined using high through-put direct binding ELISA. Briefly, the condition media at 1:10 and 1:100 fold dilution were allowed to bind to recombinant NGF protein coated MAXISORB™ plates (Nunc) at 100 ng/well. The plate-bound antibodies were detected using goat anti-mouse IgG Fcγ specific HRP conjugated polyclonal antibody (Jackson Immuno Lab). Plates were developed using TMB substrates (BD Pharmigen) and optical density at $OD_{450\ nm}$ recorded. In parallel, samples at the same dilutions were applied to a streptavidin presented biotin-labeled NGF plates, and the plate bound antibodies detected. Wells showing binding activity to either plate were selected for cell culture expansion and cryo-preserved, and antibody containing supernatants were used for further analysis to obtain specificity, affinity, and functionality profile.

In addition to the direct antigen binding screening, functional screening was also utilized in order to identify clones secreting antibody with desirable properties. Maxisorb plates were coated with 100 ng/well recombinant human TrkA-hFc overnight at 4° C. Conditioned media at 1:2 and 1:10 fold dilutions were allowed to bind to 2 ng/ml biotin-NGF in solution for 1 hour prior to transfer to the TrkA-hFc coated plates for the measurement of plate-bound biotin-NGF. The plate-bound biotin-NGF was detected using HRP conjugated streptavidin (Pierce) and developed using TMB substrates (BD Pharmingen) and optical density recorded. Hybridomas in which culture media prevented binding of biotin-NGF to TrkA-hFc were identified as potential blockers and were further characterized.

Similar in vitro screens were applied to 96-well conditioned medium from CHO cells transfected with the fully human IgG containing V genes isolated directly from antigen positive B cells. In addition, samples were screened for NGF binding activity using antigen-coated LUMINEX™ beads, to which antigen specific bound antibody was detected using PE-conjugated goat anti-human IgG Fcγ-specific polyclonal antibodies. The antigen-binding antibodies were subjected to affinity measurement using BIACORE™. Briefly, antibodies from crude culture supernatants were captured on an amine coupled hFc specific polyclonal antibody surface. Antigen binding at a single concentration was monitored. A 1:1 bimolecular interaction model was used to fit the binding sensogram to determine the antigen-binding affinities ($K_D$) using the kinetic rate constants ka and kd for each antibody interaction under identical conditions. Specifically, goat anti-human IgG Fcγ-specific polyclonal antibodies were covalently coupled onto CM-5 chip surfaces, and antibody-containing CHO supernatants were injected at 1 μl/min for 5 minutes followed by a buffer wash. Human NGF (25 nM) was injected for 3 minutes to allow NGF to bind to the human antibody immobilized surface. Immediately following NGF injection, the surfaces were buffer injected at 100 μl/min for ~10 minutes and the decay of RU signal recorded. Surfaces were regenerated to remove bound antibody and NGF, and the cycle repeated with the next CHO supernatant sample.

Example 4

Antigen Binding Affinity Determination

Antigen binding affinities of the antibodies for human NGF were determined by surface kinetics using a real-time biosensor surface plasmon resonance assay (BIACORE™). Antibodies were captured on either a goat, anti-human or anti-mouse IgG polyclonal antibody surface created by direct amine coupling of the capture antibody to a BIACORE™ chip. Various concentrations of human NGF were injected over the captured antibody surfaces while the association of the antigen to the antibody and the dissociation of the bound complex were monitored in real time. Kinetic analysis was performed to obtain the equilibrium dissociation constant ($K_D$) and dissociation rate constant, and the latter was used to calculate the antigen/antibody complex dissociation $t_{1/2}$ (Table 1). A humanized anti-human NGF monoclonal antibody E3 ("RN624") (tanezumab; CAS Registry No. 880266-57-9; US patent publication 2004/0237124, herein specifically incorporated by reference in its entirety) was used as the control.

TABLE 1

| Antibody | $K_D$ (pM) | $t_{1/2}$ |
|---|---|---|
| 301272-1D07-B10 | 0.5 | 34.6 hr |
| 301272-1H07-G9 | 60.1 | 32.8 min |
| 301272-1H08-G8 | 0.2 | 55.6 hr |
| 301272-3D08-C11 | 0.7 | 6.9 hr |
| 301272-3F12-D7 | 190.0 | 13.2 min |
| 301272-3G11-C1 | 1.1 | 14.6 hr |
| 301272-3H10-A10 | 0.1 | 25.2 hr |
| 301272-3H11-A3 | 23.8 | 4.3 hr |
| 301272-6E07-D10 | 13.0 | 4.5 hr |
| 301272-6G10-D7 | 7.7 | 44.3 min |
| 301272-7A10-D7 | 75.0 | 11.6 min |
| 301272-7C05-G1 | 162.0 | 10.1 min |
| 301272-7E05-F6 | 0.4 | 40.0 hr |
| 301272-7F11-A8 | 5.8 | 5.3 hr |
| 301272-7G09-E4 | 17.0 | 4.3 hr |
| 301272-7G10-E1 | 292.0 | 10.1 min |
| 301272-7G11-F6 | 4.9 | 2.9 hr |
| 301272-7H05-D4 | 77.6 | 1.0 hr |
| 301272-7H07-C12 | 9.8 | 6.0 hr |
| VAT 8C10-8 | 102.0 | 14.7 min |
| VAT 13F5-5 | 156.0 | 13.7 min |
| VAT 12A10-13 | 109.0 | 9.4 min |
| VAT 2C2-1 | 959.0 | 9.0 min |
| Control (RN624) | 1.3 | 35.0 hr |

Antigen binding affinities of selected purified antibodies for NGF were also determined by surface kinetics employing a real-time biosensor surface plasmon resonance assay (BIACORE™) as described above. For convenience, antibody 301272-3H10-A10 was renamed "REGN261" (HCVR/LCVR SEQ ID NOs:84/92 and hIgG1 SEQ ID NO:541); 301272-6E07-D10 was renamed "REGN263" (HCVR/LCVR SEQ ID NO:208/216 and hIgG1 SEQ ID NO:541). Derived antibodies tested included REGN472 (HCVR/LCVR SEQ ID NO:100/102 and hIgG1 SEQ ID NO:541), REGN474 (HCVR/LCVR SEQ ID NO:100/102 and mutant hIgG4 SEQ ID NO:543), REGN475 (HCVR/LCVR SEQ ID NO:108/110 and mutant hIgG4 SEQ ID NO:543), REGN476 (HCVR/LCVR SEQ ID NO:224/226 and mutant hIgG4 SEQ ID NO:543), and REGN477 (HCVR/LCVR SEQ ID NO:232/234 and mutant hIgG4 SEQ ID NO:543).

TABLE 2

| Antibody | $K_D$ (pM) | $t_{1/2}$ (hr) |
|---|---|---|
| REGN472 | 0.41 | 30 |
| REGN474 | 0.41 | 31 |
| REGN475 | 0.18 | 57 |
| REGN476 | 8.91 | 4 |
| REGN477 | 7.98 | 4 |
| Control (RN624) | 1.25 | 35 |

Example 5

Cross-Reactivity to Neurotrophin-3 (NT-3)

NGF and NT-3 belong to nerve growth factor family and are small, basic, secretory proteins that allow the survival of specific neuronal populations. Though these two neurotrophins share some amino acid identities, biological functions may vary (Barde et al. 1990 Prog Growth Factor Res 2(4): 237-48).

The anti-NGF antibodies were examined for binding cross-reactivity with human NT-3. Briefly, goat anti-human IgG polyclonal antibody was chemically linked to a CM5 chip. Anti-NGF monoclonal antibodies were injected forming a surface of about 50 to 900 RU of immobilized antibody through the interaction with the chip coupled polyclonal antibodies. NGF or NT-3 protein at a concentration of 20 nM was injected over the surface, followed by a buffer wash to allow bound ligand to dissociate. Both association and dissociation phases were monitored and data were analyzed. Results are shown in Table 3 (NB=no binding activity observed). In contrast to the control antibody (RN624), all of the test antibodies showed no measurable binding to NT-3, thus indicating a higher degree of antigen specificity relative to the control antibody.

TABLE 3

| Antibody | NGF $K_D$ (pM) | NT-3 $K_D$ (nM) |
|---|---|---|
| 301272-1D07-B10 | 0.5 | NB |
| 301272-1H07-G9 | 60.1 | NB |
| 301272-1H08-G8 | 0.2 | NB |
| 301272-3D08-C11 | 0.7 | NB |
| 301272-3F12-D7 | 190.0 | NB |
| 301272-3G11-C1 | 1.1 | NB |
| 301272-3H10-A10 | 0.1 | NB |
| 301272-3H11-A3 | 23.8 | NB |
| 301272-6E07-D10 | 4.3 | NB |
| 301272-6G10-D7 | 7.7 | NB |
| 301272-7A10-D7 | 75.0 | NB |
| 301272-7C05-G1 | 162.0 | NB |
| 301272-7E05-F6 | 0.1 | NB |
| 301272-7F11-A8 | 7.5 | NB |
| 301272-7G09-E4 | 5.5 | NB |
| 301272-7G10-E1 | 292.0 | NB |
| 301272-7G11-F6 | 4.9 | NB |
| 301272-7H05-D4 | 77.6 | NB |
| 301272-7H07-C12 | 9.8 | NB |
| Control (RN624) | 1.3 | 1.1 |

OCTET™-based solution competition assays were also employed to measure the ability of REGN475 and RN624 to compete in solution for the binding to NT-3, NGF or human brain derived neurotrophic factor (hBDNF). Briefly, antibody-antigen samples were prepared by pre-incubating control antibody RN624 (2.5 μg/ml) or REGN475 (2.5 μg/ml), with various concentrations of NT-3 (0 to 4 μM), hBDNF (0 to 4 μM) or NGF (0 to 0.2 μM) for 1 hour at 30° C. Streptavidin high binding FA sensors (HBS, ForteBio, Inc., CA) were incubated with biotin-NGF at 2 μg/ml for 10 min at 30° C. Biotin-NGF bound sensors were then incubated with the pre-incubated antigen-antibody samples for 10 min at 30° C. Changes in the thickness of the biological layer were measured after incubation. The binding was normalized as a percentage of binding relative to the binding of antibody in absence of competitor. As shown in Table 4, the binding between NGF and RN624 was blocked by NT-3 in a dose-dependent manner, whereas binding between REGN475 and NGF was not blocked by NT-3. The presence of hBDNF did not block the binding of either RN624 or REGN475 to NGF, whereas the presence of soluble NGF almost completely blocked the binding of both RN624 and REGN475 to immobilized NGF.

TABLE 4

| Competitor | RN624 % Binding | REGN475 % Binding |
|---|---|---|
| NT-3 (4 μM) | 17 | 102 |
| NT-3 (2 μM) | 26 | 102 |
| NT-3 (1 μM) | 38 | 98 |
| NT-3 (0.5 μM) | 52 | 93 |
| NT-3 (0.25 μM) | 72 | 101 |
| NT-3 (0 μM) | 100 | 100 |
| BDNF (4 μM) | 103 | 116 |
| BDNF (2 μM) | 104 | 115 |
| BDNF (1 μM) | 104 | 106 |
| BDNF (0 μM) | 100 | 100 |
| NGF (0.2 μM) | 1 | 3 |
| NGF (0.1 μM) | −1 | 2 |
| NGF (0.05 μM) | 0 | 1 |
| NGF (0 μM) | 100 | 100 |

The binding between selected purified human anti-NGF antibody REGN472, REGN474, REGN475, REGN476, REGN477, or control antibody RN624 and NT-3 was also evaluated using the BIACORE™ assay with NT-3 concentrations ranging from 1.25 nM to 40 nM. While control antibody (RN624) bound NT-3 with a $K_D$ of 1.1 nM, none of the test antibodies exhibited measurable affinity for NT-3.

Example 6

Cross-Reactivity to Murine and Rat NGF

Human NGF (NGF) is highly homologous in amino acid sequence to mouse NGF (mNGF) and rat NGF (rNGF) with about 90% identity. The binding affinities of the antibodies to both mNGF and rNGF were determined as described above. All antibodies showed cross-reactivity to both mNGF and rNGF. One group of antibodies bound NGF from all species strongly with a $K_D$ value of less than 10 pM; a second group preferably bound NGF and exhibited $K_D$s>~100 pM for mNGF and rNGF (control=RN624) (Table 5).

TABLE 5

| Antibody | Human NGF $K_D$ (pM) | mNGF $K_D$ (pM) | rNGF $K_D$ (pM) |
|---|---|---|---|
| 301272-1D07-B10 | 0.5 | 3.0 | 6.6 |
| 301272-1H07-G9 | 60.1 | 2280.0 | 6330.0 |
| 301272-1H08-G8 | 0.2 | 1.7 | 0.7 |
| 301272-3D08-C11 | 0.7 | 5.0 | 8.5 |
| 301272-3F12-D7 | 190.0 | 3130.0 | 8710.0 |
| 301272-3G11-C1 | 1.1 | 6.1 | 5.9 |
| 301272-3H10-A10 | 0.1 | 0.2 | 0.6 |
| 301272-3H11-A3 | 23.8 | 619.0 | 800.0 |
| 301272-6E07-D10 | 13.0 | 362.0 | 360.0 |
| 301272-6G10-D7 | 7.7 | 94.7 | 157.0 |
| 301272-7A10-D7 | 75.0 | 2630.0 | 4900.0 |
| 301272-7C05-G1 | 162.0 | 2000.0 | 1790.0 |
| 301272-7E05-F6 | 0.4 | 4.1 | 1.6 |
| 301272-7F11-A8 | 5.8 | 320.0 | 459.0 |
| 301272-7G09-E4 | 16.8 | 379.0 | 425.0 |
| 301272-7G10-E1 | 292.0 | 7090.0 | 11800.0 |
| 301272-7G11-F6 | 4.9 | 157.0 | 160.0 |
| 301272-7H05-D4 | 77.6 | 5520.0 | 7090.0 |
| 301272-7H07-C12 | 9.8 | 1200.0 | 473.0 |
| Control (RN624) | 1.25 | 1.4 | 1.5 |

The binding affinity of selected purified anti-NGF antibodies to mNGF and rNGF were also determined (Table 6).

TABLE 6

| Antibody | NGF $K_D$ (pM) | mNGF $K_D$ (pM) | rNGF $K_D$ (pM) |
|---|---|---|---|
| REGN472 | 0.41 | 0.61 | 3.96 |
| REGN474 | 0.41 | 0.43 | 3.42 |
| REGN475 | 0.18 | 0.36 | 0.93 |
| REGN476 | 8.91 | 115 | 155 |
| REGN477 | 7.98 | 133 | 164 |
| Control (RN624) | 1.25 | 1.4 | 1.51 |

Example 7

Inhibition of NGF Binding to Receptors TrkA/hFc and p75/hFc

To identify blocking antibodies, a receptor blocking assay was designed using a BIACORE™ 3000 instrument. Recombinant human TrkA-hFc and human p75-hFc proteins were amine-coupled to a CM5 chip to a density of about 5000-6000 RU. Human NGF (10 nM to 25 nM) was bound to the TrkA and p75 surface to determine maximal RU for NGF binding. The surface was then regenerated and 10 nM to 25 nM NGF was mixed with excess molar concentrations of the individual antibodies or soluble receptorbodies, and the solution was injected over the regenerated chip surface to determine the remaining free NGF binding signals. Table 7 shows the percentage free NGF bound to TrkA and p75 in the presence of antibody or receptorbody. The maximal RU binding of human NGF in the absence of antibody was given a relative value of 100%. As positive controls, RN624, TrkA-hFc and p75-hFc in solution were used and, as a negative binding control, IgG1 control (AVASTIN®; Genentech, CA) was used.

TABLE 7

| Antibody | % Binding TrkA-hFc | % Binding p75-hFc |
|---|---|---|
| NGF alone | 100 | 100 |
| 301272-1D07-B10 | 2 | 4 |
| 301272-1H07-G9 | 20 | 25 |
| 301272-1H08-G8 | 1 | 3 |
| 301272-3D08-C11 | 1 | 2 |
| 301272-3F12-D7 | 25 | 23 |
| 301272-3G11-C1 | 1 | 1 |
| 301272-3H10-A10 | 1 | 2 |
| 301272-3H11-A3 | 18 | 20 |
| 301272-6E07-D10 | 4 | 6 |
| 301272-6G10-D7 | 2 | 2 |
| 301272-7A10-D7 | 31 | 26 |
| 301272-7C05-G1 | 1 | 1 |
| 301272-7E05-F6 | 1 | 1 |
| 301272-7F11-A8 | 4 | 3 |
| 301272-7G09-E4 | 8 | 16 |
| 301272-7G10-E1 | 62 | 62 |
| 301272-7G11-F6 | 1 | 1 |
| 301272-7H05-D4 | 14 | 20 |
| 301272-7H07-C12 | 42 | 81 |
| VAT 8C10-8 | 4 | 395 |
| VAT 13F5-5 | 4 | 5 |
| VAT 12A10-13 | 11 | 539 |
| VAT 2C2-1 | 11 | 360 |
| REGN472 | 4 | 7 |
| REGN474 | 6 | 9 |
| REGN475 | 6 | 10 |
| REGN476 | 6 | 13 |
| REGN477 | 9 | 13 |
| Control mAb (RN624) | 10 | 16 |
| Control (TrkA-hFc) | 10 | 15 |
| Control (p75-hFc) | 3 | 5 |
| IgG1 Control | 116 | 116 |

The ability of selected test antibodies, REGN472, REGN474, REGN475, REGN476 and REGN477, and control antibody RN624 to block human NGF binding to human TrkA and p75 receptors was also quantitatively measured with a competition sandwich ELISA, in which the presence of the antibody with a fixed concentration of NGF in solution prevented NGF from binding to TrkA-hFc or p75-hFc coated on a microtiter plate. The human NGF used in the assay was a recombinant protein produced in *E. coli* and the human TrkA-hFc and p75-hFc proteins were dimeric fusion proteins consisting of the extracellular domains of the respective receptors fused in-line with the Fc portion of human IgG1. Biotin-labeled NGF protein at a fixed concentration of 50 pM was titrated with various amounts of the antibody from 1.5 pM to 1.5 nM in solution for one hour at room temperature. The amount of unbound free biotin-NGF in the solution mixtures was then quantified by capturing the biotin-NGF on either hTrkA-hFc or hp75-hFc coated microtiter plates, followed by detection of plate bound biotinylated-NGF with Streptavidin-HRP. Specifically, the microtiter plates were prepared by coating the plates with 0.5 μg/ml hTrkA-hFc or 1 μg/ml hp75-hFc solution in PBS buffer overnight at 4° C., followed by blocking the plates with 0.5% BSA prior to use. To measure the unbound biotin-NGF, the pre-incubated antibody and biotin-NGF solutions were transferred to the receptor-coated plates followed by 1-hour incubation at room temperature. The plate-bound biotinylated-NGF was detected with Streptavidin-HRP and developed with a colorimetric TMB substrate, and $OD_{450\ nm}$ recorded. The dependence of the $OD_{450\ nm}$ values on REGN475 concentrations in the pre-binding solutions was analyzed using a sigmoidal dose-response model provided by PRISM™ (Graph Pad, CA). The predicted $IC_{50}$ value, which is defined as the antibody concentration required to block 50% of the binding of 50 pM biotinylated-NGF to the receptor coated plates, was used as an indicator of the potency of the antibody in blocking NGF binding to hTrkA-hFc or hp75-hFc. Table 8 shows $IC_{50}$ values of each antibody tested against hTrkA-hFc and hp75-hFc. Control mAb=RN624.

TABLE 8

| | TrkA-hFc Blocking $IC_{50}$ (pM) | p75-hFc Blocking $IC_{50}$ (pM) |
|---|---|---|
| REGN472 | 12 | 12 |
| REGN474 | 8.1 | 6.3 |
| REGN475 | 20 | 22 |
| REGN476 | 65 | 61 |
| REGN477 | 65 | 62 |
| Control (RN624) | 48 | 72 |

Example 8

Inhibition of NT-3 Binding to Receptors TrkA-, TrkB-, TrkC- and p75-hFc

The binding of 20 nM human NT-3 to human TrkA-, TrkB-, TrkC- and p75-hFc surfaces, respectively, in the presence of 500 nM of REGN475, RN624 and AVASTIN® (IgG1 control), was also tested. Human TrkA-hFc (9300 RU), human TrkB-hFc(6000 RU), human TrkC-hFc (9100 RU) and human p75-hFc (7500 RU) were covalently coupled to BIACORE® CM5 chip surfaces by amine-coupling procedure. Twenty nM of human NT-3 was mixed with 500 nM of control (IgG1 control AVASTIN®), REGN475, RN624, hTrkA-hFc, TrkB-hFc, TrkC-hFc or p75-hFc in solution. The binding mixture was first incubated at room temperature to reach equilibrium (about 1 hr) and then was injected over the above TrkA-hFc, TrkB-hFc, TrkC-hFc and p75-hFc surfaces. The level of human NT-3 binding in each sample was measured. The binding RU from each sample mixture was normalized according to the RU value from the negative control sample (i.e., 20 nM human NT-3 with 500 nM AVASTIN®) and presented as % binding to Trk surfaces (Table 9). REGN475 showed almost no interference with NT-3 binding to the receptors, while the remaining samples showed significant blocking of NT-3 binding to the receptors.

TABLE 9

| Antibody | TrkA-hFc | TrkB-hFc | TrkC-hFc | p75-hFc |
|---|---|---|---|---|
| IgG1 Control | 100 | 100 | 100 | 100 |
| RN624 | 7 | 8 | 8 | 19 |
| REGN475 | 90 | 99 | 101 | 103 |
| TrkA-hFc | 21 | 5 | 3 | 7 |
| TrkB-hFc | 6 | 0 | 0 | 0 |
| TrkC-hFc | 11 | 0 | 0 | 0 |
| P75-hFc | 14 | 2 | 2 | 4 |

Example 9

Neutralization of NGF Biological Activity In Vitro

The ability of NGF antibodies to block NGF-dependent and TrkA receptor-mediated cell growth activity was carried out using MG87 cells stably transfected with a plasmid encoding human TrkA receptor. Briefly, the transfected cells were trypsinized and resuspended at approximately $2.5\times10^5$ cells per ml and plated at 5,000 cells per well in a 96-well tissue culture plate. The purified antibody proteins were serially diluted in defined medium plus 0.1% BSA and added to the plated cells at concentrations ranging from 0 to 500 nM. Human NGF was added to the wells to a final concentration of 373 pM. The response was measured after incubating the cells for 3 days at 37° C. in a humidified 5% $CO_2$ incubator. Cell growth activity was measured with a CCK8 kit (Dojindo) and $OD_{450\ nm}$ recorded. The dependency of the signals on the concentrations of antibody was analyzed and $IC_{50}$ values reported (Table 10, column 2).

The ability of NGF antibodies to block NGF signaling p75 and TrkA receptor-mediated activity was also measured in vitro using a rat adrenal medulla cell line, PC12, which express both receptors endogenously (Urdiales et al. 1998 J. Neuroscience 18(17):6767-6775). Briefly, PC12 cells were stably transfected with a reporter plasmid containing a serum response element (SRE) linked to a luciferase gene. The transfected cells were resuspended at approximately $2.5\times10^5$ cells per ml and plated at 50,000 cells per well in a 96-well tissue culture plate in Opti-MEM media overnight. The purified antibody proteins were serially diluted in medium (DMEM plus 0.1% BSA) and added to the plated cells at concentrations ranging from 0 to 100 nM. Human NGF was added to the wells to a final concentration of 12.5 pM. Luciferase activity was measured after incubating the cells for 6 hours at 37° C. in a humidified 7.5% $CO_2$ incubator using BRIGHT GLOW™ luciferase assay system (Promega). $IC_{50}$ values were determined as described above, and reported in Table 10, column 3. Control mAb=RN624.

TABLE 10

| Antibody | MG87 $IC_{50}$ (nM) | PC12 $IC_{50}$ (nM) |
|---|---|---|
| 301272-1D07-B10 | <0.186 | 0.011 |
| 301272-1H07-G9 | 2.000 | 0.261 |
| 301272-1H08-G8 | <0.186 | 0.006 |
| 301272-3D08-C11 | 0.576 | 0.005 |
| 301272-3F12-D7 | <0.186 | — |
| 301272-3G11-C1 | <0.186 | 0.019 |
| 301272-3H10-A10 | <0.186 | 0.009 |
| 301272-3H11-A3 | 16.000 | 0.842 |
| 301272-6E07-D10 | 0.293 | 0.726 |
| 301272-6G10-D7 | 106.000 | 0.087 |
| 301272-7A10-D7 | 15.000 | — |
| 301272-7C05-G1 | <0.186 | 0.035 |
| 301272-7E05-F6 | <0.186 | 0.018 |
| 301272-7F11-A8 | 0.428 | 0.071 |
| 301272-7G09-E4 | 3.000 | — |
| 301272-7G10-E1 | <0.186 | — |
| 301272-7G11-F6 | 9.000 | 0.088 |
| 301272-7H05-D4 | 3.000 | — |
| 301272-7H07-C12 | 0.383 | 0.183 |
| VAT2C2-1 | 532.000 | — |
| VAT8C10-8 | 41.000 | — |
| VAT12A10-13 | 41.000 | — |
| VAT13F5-5 | 5.000 | — |
| Control (RN624) | <0.186 | 0.021 |

The ability of selected purified anti-NGF antibodies, REGN472, REGN474, and REGN475, and control mAb RN624 to block NGF signaling through p75 and TrkA receptor-mediated activity in a PC12 cell line was also evaluated with the luciferase assay described above (Table 11).

TABLE 11

| Antibody | $IC_{50}$ (pM) |
|---|---|
| REGN472 | 4.5 |
| REGN474 | 6.6 |
| REGN475 | 9.6 |
| Control (RN624) | 4.9 |

The ability of anti-NGF antibody, REGN475, and control antibody to block NT-3 signaling through p75 and TrkA receptor-mediated activity in PC12 cell line was evaluated with the luciferase assay described above, modified by replacing 12.5 pM NGF with 75 nM NT-3. Results showed that the control mAb RN624 blocked NT-3 signaling with an $IC_{50}$ of about 104.8 nM, while REGN475 did not affect NT-3 signaling under the current experimental conditions.

Further, a bioassay was developed to determine the ability of anti-NGF antibodies, REGN475 and RN624, to neutralize NT-3 mediated cellular function through TrkC in vitro. An engineered HEK293 cell line expressing TrkC was transfected with a SRE-luciferase reporter plasmid. NT-3 drives luciferase expression in a 6-hour assay. The ability of REGN475 and RN624 to block NT-3 signaling through TrkC receptor-mediated activity in this engineered cell line was evaluated with the luciferase assay. The engineered HEK293 cell line was seeded onto 96-well plates at $1\times10^4$ cells/well in serum-free media and incubated overnight at 37° C., 5% $CO_2$. REGN475 and RN624 at concentrations ranging from 1.6 pM to 28 pM were preincubated with 15 pM NT-3 for 1 hour and the mixture was added to the cells. The cells were then incubated at 37° C., 5% $CO_2$ for 6 hours. Luciferase activity was determined by adding an equal well volume of BRIGHT GLOW™ (Promega). The result showed that RN624 inhibited NT-3-mediated luciferase activity with an $IC_{50}$ of ~150-200 nM in the presence of a constant concentration of 15 pM NGF, whereas REGN475 did not inhibit NT-3 mediated luciferase activity.

Example 10

Neutralization of NGF Biological Activity In Vivo

Complete Freund's Adjuvant (CFA) test of inflammatory pain. To determine if anti-NGF antibodies could relieve pain in a chronic peripheral inflammatory mouse model, complete Freund's adjuvant (CFA) was injected subcutaneously (s.c.) into the hind paw of C57BL/6 male mice, causing thermal hyperalgesia, which was measured using the Hargreaves' test (Torres et al. (2007) Pain 130:267-278). Control mice received the vehicle (i.e., PBS) only. After acclimating the mice to the Hargreaves' apparatus (model 336, IITC Life Science) for 2-3 hours per day for 3 days, they were tested in the apparatus with an active intensity setting of 17%. A cut-off time of 25 sec was used to avoid tissue damage. For each mouse, 3 readings were obtained during a period of 30 min per day and the median latency was used for analysis. After obtaining a baseline reading in the Hargreaves' apparatus, test anti-NGF antibodies, 301272-7E05-F6 (REGN268) and 301272-7G09-E4 (REGN270), and humanized anti-NGF antibody (RN624) as a positive control, were injected s.c. at 10 mg/kg or 25 mg/kg, 1 hr prior to injecting a 50% solution of CFA (10 mg/20 μl) into the intraplantar hind paw. The Hargreaves' test was repeated daily for up to 4 days after CFA injection and % decrease from the baseline in paw withdrawal latency calculated (Tables 12 and 13, mean % change±SEM). A significant decrease in thermal hyperalgesia was observed for at least one of the days examined for each of the antibodies tested, compared to control mice that received vehicle only (p<0.001-0.05). There was no statistical difference between the tested antibodies and the control antibody. Table 12: n=7 for each group; all groups 10 mg/kg. Table 13: vehicle: n=5; control RN624: n=5, 10 mg/kg; both REGN269: n=9).

TABLE 12

| Time after CFA injection | Vehicle | Control (RN624) | REGN268 | REGN270 |
|---|---|---|---|---|
| Baseline | 0.0 ± 0.0 | 0.0 ± 0.0 | 0.0 ± 0.0 | 0.0 ± 0.0 |
| Day 1 | −73.8 ± 1.8 | −58.3 ± 5.5 | −68.3 ± 3.0 | −55.8 ± 9.2 |
| Day 2 | −67.9 ± 2.1 | −30.9 ± 5.2 | −44.7 ± 9.5 | −36.6 ± 9.9 |
| Day 3 | −54.4 ± 2.8 | −20.7 ± 6.3 | −28.9 ± 11.3 | −38.1 ± 5.6 |

TABLE 13

| Time after CFA injection | Vehicle | Control (RN624) | REGN269 10 mg/kg | REGN269 25 mg/kg |
|---|---|---|---|---|
| Baseline | 0.0 ± 0.0 | 0.0 ± 0.0 | 0.0 ± 0.0 | 0.0 ± 0.0 |
| Day 1 | −82.6 ± 1.6 | −61.7 ± 9.7 | −79.8 ± 1.8 | −80.4 ± 2.2 |
| Day 2 | −76.7 ± 3.6 | −33.1 ± 17.9 | −57.0 ± 8.2 | −54.0 ± 5.2 |
| Day 3 | −60.8 ± 5.5 | −9.6 ± 15.4 | −23.9 ± 12.4 | −41.1 ± 8.9 |
| Day 4 | −40.3 ± 5.0 | −0.4 ± 18.5 | −25.3 ± 6.6 | −16.9 ± 12.6 |

Post-operative incision pain model. A rodent model of post-operative pain in which a hind paw plantar incision causes increased sensitivity to touch, guarding behavior, and thermal hyperalgesia, was used to study the efficacy of anti-NGF antibody therapy. For the plantar incision surgery, C57BL/6 mice under isoflurane received an incision through skin, fascia and then isolating the underlying flexor muscle and bisecting vertically. After suture and recovery, the mice were tested for thermal hyperalgesia in the Hargreaves' test and for guarding behavior in the weight bearing test (model 600, IITC Life Science) for 5 days. A single s.c. injection of vehicle (n=7), mAb REGN268 (n=7), or control mAb RN624 (n=7), at 10 mg/kg, was administered 1 hr prior to the incision (Table 14, mean percent change from Hargreaves baseline±SEM. Table 15 shows results of the weight bearing test (mean percent weight distribution on affected limb±SEM) (n=7 for each group, control RN624 and REGN268 each 10 mg/kg). In both tests, the pre-treatment with the test antibody or the control antibody significantly reduced the post-operative pain compared to the control mice that received vehicle only (p<0.001-0.05).

TABLE 14

| Time after surgery | Vehicle | Control (RN624) | REGN268 |
|---|---|---|---|
| Baseline | 0.00 ± 0.0 | 0.00 ± 0.0 | 0.00 ± 0.0 |
| Day 1 | −72.4 ± 4.4 | −62.5 ± 10.6 | −59.9 ± 8.9 |
| Day 2 | −72.7 ± 3.5 | −55.2 ± 9.4 | −34.4 ± 21.3 |
| Day 3 | −63.8 ± 7.4 | −5.3 ± 12.1 | −19.8 ± 18.8 |
| Day 4 | −52.1 ± 7.8 | −6.4 ± 8.7 | 6.9 ± 4.4 |
| Day 5 | −32.7 ± 10.0 | −5.3 ± 5.6 | 6.8 ± 7.8 |

TABLE 15

| Time after surgery | Vehicle | Control (RN624) | REGN268 |
|---|---|---|---|
| Day 0 | 49.7 ± 0.9 | 49.0 ± 0.5 | 50.3 ± 0.7 |
| Day 1 | 35.3 ± 1.5 | 44.8 ± 1.9 | 39.5 ± 3.4 |
| Day 2 | 34.3 ± 1.9 | 42.7 ± 1.8 | 40.7 ± 2.0 |
| Day 3 | 34.1 ± 2.5 | 48.7 ± 1.9 | 42.0 ± 3.3 |
| Day 4 | 42.2 ± 0.8 | 47.2 ± 1.2 | 44.8 ± 1.0 |
| Day 5 | 48.6 ± 1.3 | 49.7 ± 0.7 | 48.8 ± 0.8 |

To study whether anti-NGF antibodies could relieve established pain in the post-operative incision pain model, REGN475 (25 mg/kg, n=7), RN624 (25 mg/kg, n=7), and IgG1 control antibody (25 mg/kg, n=7) were intraperitoneally (i.p.) injected on day 1 post-surgery after performing the behavioral work. Thermal hyperalgesia was studied in the Hargreaves' test and mechanical allodynia was tested in the von Frey test. In this latter test, mice were tested after being acclimated for 2-3 hours for 4 days in an apparatus with a wire mesh floor. The test was performed by applying, in ascending order, a series of von Frey hairs through the wire mesh onto the plantar surface of the hind paw with the incision. A response was considered positive if the paw was raised from the platform in response to application of the filament. Starting from the thinnest hair, each von Frey filament was applied up to five times until a response was observed. The result from the Hargreaves' test (Table 16) showed that the REGN475 antibody treatment led to a significant reversal of the thermal hyperalgesia by 72 hours post-surgery (p<0.001-0.01). This return to baseline was not observed in the RN624 treated cohort of mice, which behaved similarly to the IgG control treated group. In the von Frey test (Paw Withdrawal Threshold) (g) (Table 17), both anti-NGF antibodies caused similar relief of mechanical allodynia (p<0.001-0.05) (IgG1 control=AVASTIN®, 25 mg/kg, n=7; RN624, 25 mg/kg, n=7; REGN475, 25 mg/kg, n=7).

TABLE 16

| Time after anti-NGF treatment | IgG1 Control | RN624 | REGN475 |
|---|---|---|---|
| Baseline | 0.0 ± 0.0 | 0.0 ± 0.0 | 0.0 ± 0.0 |
| Day 1 | −66.5 ± 9.0 | −74.7 ± 4.3 | −72.6 ± 5.4 |
| 6 hr | −79.8 ± 3.8 | −68.1 ± 5.2 | −59.3 ± 9.6 |
| 23 hr | −77.6 ± 3.6 | −40.5 ± 8.9 | −37.0 ± 15.0 |
| 47 hr | −61.2 ± 6.6 | −37.6 ± 7.2 | −30.5 ± 10.8 |
| 72 hr | −57.0 ± 7.9 | −47.2 ± 8.0 | 2.1 ± 17.3 |

TABLE 17

| Time after anti-NGF Treatment | IgG1 Control | RN624 | REGN475 |
|---|---|---|---|
| Baseline | 1.314 ± 0.137 | 1.314 ± 0.137 | 1.286 ± 0.074 |
| Day 1 | 0.011 ± 0.002 | 0.010 ± 0.002 | 0.010 ± 0.002 |
| 5 hr | 0.011 ± 0.002 | 0.083 ± 0.053 | 0.034 ± 0.009 |
| 22 hr | 0.029 ± 0.004 | 0.610 ± 0.123 | 0.714 ± 0.074 |
| 45 hr | 0.190 ± 0.135 | 0.909 ± 0.216 | 1.086 ± 0.184 |
| 70 hr | 0.194 ± 0.034 | 1.143 ± 0.189 | 1.571 ± 0.437 |

On day 4, after the behavioral tests from post incision pain model were completed, the mice's sera were collected and analyzed for circulating levels of neurotrophin-3 (NT-3) using a sandwich ELISA. The limit of detection (~40 pg/ml) was defined as two standard deviations (2σ) above background with a minimum of five NT-3 standards to define the response to concentration curve. NT-3 levels from mice treated with RN624 (mean±std dev pg/ml, Table 18) showed a significant increase (172±114 pg/ml, n=7) from those treated with either REGN475 (not detected=ND, n=7) or IgG control (AVASTIN®; ND, n=7).

TABLE 18

| Group | Serum NT-3 |
|---|---|
| RN624 | 172 ± 114 |
| REGN475 | ND |
| IgG1 control | ND |

For comparison, naïve C57BL/6 mice under isoflurane were given one s.c. injection (50 mg/kg) of REGN475, RN624 or IgG1 control mAb (AVASTIN®) and their sera were analyzed at 1, 7 and 14 days post treatment for NT-3 levels using a sandwich ELISA. The limit of detection (~40 pg/ml) was defined as two standard deviations (2σ) above background with a minimum of five NT-3 standards to define the response to concentration curve. NT-3 levels (Table 19) in RN624 treated mice (131-199 pg/ml, n=6) were elevated compared to REGN475 (ND, n=6) or IgG control (ND, n=6), as observed with the post-operative incision pain model described above.

TABLE 19

| Group | Serum NT-3 |
|---|---|
| Day 1 | |
| RN624 | 131 ± 41 |
| REGN475 | ND |
| IgG1 Control | ND |
| Day 7 | |
| RN624 | 199 ± 15 |
| REGN475 | ND |
| IgG1 Control | ND |
| Day 14 | |
| RN624 | 196 ± 35 |
| REGN475 | ND |
| IgG1 Control | ND |

Acute gout joint pain model. A mouse model of joint pain caused by injection of monosodium urate (MSU) crystals into the ankle was used to study the efficacy of the antibodies of the invention to treat gout arthritic joint pain. Endotoxin-free MSU crystals (0.5 mg/20 μl) were injected intra-articularly into the ankle of C57BL/6 mice and the mice were then tested for heel thermal pain in the Hargreaves' test for up to 3 days post-MSU crystals injection. The acclimation parameters and apparatus setting for the Hargreaves' test is as described above. Test mAb 7E05-F6 (REGN268; n=7), 6E07-D10 (REGN263; n=7), or control humanized mAb (RN624; n=7), or vehicle (n=7) was s.c. injected at 10 mg/kg 1 hr prior to the MSU crystals ankle injection. As shown in Tables 20 and 21, the test antibodies significantly reduced the joint pain, compared to the control mice that received vehicle only (p<0.001-0.05).

TABLE 20

| Time after MSU crystals ankle injection | Vehicle | Control (RN624) | REGN268 | REGN263 |
|---|---|---|---|---|
| Baseline | 0.0 ± 0.0 | 0.0 ± 0.0 | 0.0 ± 0.0 | 0.0 ± 0.0 |
| Day 1 | −62.4 ± 3.1 | −33.3 ± 5.2 | −28.1 ± 7.8 | −36.3 ± 3.8 |
| Day 2 | −44.2 ± 3.5 | −4.5 ± 11.2 | 29 ± 19.3 | 16.8 ± 22.3 |
| Day 3 | −24.9 ± 7.9 | −3.2 ± 12.0 | 12.1 ± 15.5 | 4.5 ± 15.5 |
| Day 4 | −11.6 ± 10.5 | 28.3 ± 18.7 | 19.9 ± 16.5 | −9.0 ± 5.5 |

TABLE 21

| Time after MSU crystals ankle injection | Vehicle | Control (RN624) | REGN268 | REGN263 |
|---|---|---|---|---|
| Baseline | 0.0 ± 0.0 | 0.0 ± 0.0 | 0.0 ± 0.0 | 0.0 ± 0.0 |
| Day 1 | −62.6 ± 2.7 | −36.0 ± 6.8 | −46.7 ± 4.2 | −53.9 ± 4.0 |
| Day 2 | −54.8 ± 2.7 | −11.8 ± 9.8 | −28.5 ± 8.4 | −35.3 ± 8.5 |
| Day 3 | −31.8 ± 3.4 | −5.3 ± 8.2 | −12.6 ± 9.0 | −28.5 ± 8.6 |

The ability of an anti-NGF antibody to relieve established pain in the acute gout model was further studied in mice injected with an IL-1 antagonist (IL-1 trap (rinolacept), Economides et al. (2003) Nature 9:47-52) or colchicine. A day after injecting the MSU crystals into the ankles, mice were injected with mIL-1 trap (35 mg/kg; n=7), colchicine (1 mg/kg; n=7), control mAb RN624 (10 mg/kg; n=7), or vehicle (n=7), and tested for thermal hyperalgesia as described above. Additionally, another cohort of mice (n=3) received co-treatment with both mIL-1 trap and the control RN624. Combination therapy of anti-NGF antibody and IL-1 antagonist significantly relieved the established thermal hyperalgesia compared to treatment with vehicle only (p<0.001-0.05), or either anti-NGF antibody alone (p<0.001) or IL-1 antagonist alone (p<0.001) at Day 2 post-treatment (Table 22).

TABLE 22

| Time | Vehicle | mIL-1 Trap | Colchicine | Control (RN624) | mIL-1Trap + RN624 |
|---|---|---|---|---|---|
| Baseline | 0.0 ± 0.0 | 0.0 ± 0.0 | 0.0 ± 0.0 | 0.0 ± 0.0 | 0.0 ± 0.1 |
| Day 1 post MSU injection | −51.9 ± 3.0 | −52.9 ± 2.6 | −52.8 ± 2.1 | −51.9 ± 2.4 | −46.6 ± 4.3 |
| 7 hr post treatment | −54.8 ± 2.0 | −50.6 ± 1.8 | −33.1 ± 4.9 | −53.2 ± 3.0 | −43.3 ± 4.4 |
| Day 1 post treatment | −46.8 ± 2.1 | −31.9 ± 6.2 | −23.1 ± 7.1 | −32.0 ± 10.6 | −3.7 ± 11.0 |
| Day 2 post treatment | −37.3 ± 3.6 | −9.1 ± 9.4 | −23.0 ± 7.6 | −27.6 ± 8.3 | 40.0 ± 29.1 |
| Day 3 post treatment | −26.9 ± 4.4 | −12.4 ± 10.4 | −14.3 ± 9.8 | −9.1 ± 10.9 | 21.9 ± 19.9 |

Neuropathic pain. The mouse Seltzer model of neuropathic pain (Malmberg et al. (1998) Pain 76:215-222) was used with C57BL/6 male mice, in which a partial nerve injury was produced by tying a tight ligature with a 7-0 silk suture around approximately ⅓ to ½ the diameter of the sciatic nerve of one single thigh per mouse. Post-surgery, the mice were allowed to recover for at least two days and then they were studied for several weeks post-surgery for thermal hyperalgesia in the Hargreaves' test. Controls were sham-operated mice in which the sciatic nerve was exposed and elevated but not tied. Following surgery, the mice were tested at day 4 and at day 7 post-surgery to confirm that the thermal hyperalgesia had developed. At day 7 post-surgery, the mice were injected s.c. with mAb REGN268 (100 mg/kg), IgG1 control (AVASTIN® 100 mg/kg), and with vehicle. REGN268 significantly relieved established thermal hyperalgesia in this nerve injury model (Table 23; $p<0.05$). This pain relief was not observed in the sham-operated mice. Results expressed as mean percent change from Hargreaves baseline±SEM (sham-vehicle, n=3; sham-100 mg/kg IgG1 control (AVASTIN®), n=4; sham-100 mg/kg REGN268, n=5; Seltzer-vehicle, n=5; Seltzer-100 mg/kg IgG1 control (AVASTIN®), n=5; Seltzer-100 mg/kg REGN268, n=8).

TABLE 23

| Days after Surgery | Sham-Vehicle | Sham-IgG1 control | Sham-REGN268 | Seltzer-Vehicle | Seltzer-IgG1 control | Seltzer-REGN268 |
|---|---|---|---|---|---|---|
| 0 | 0.0 ± 0.0 | 0.0 ± 0.0 | 0.0 ± 0.0 | 0.0 ± 0.0 | 0.0 ± 0.0 | 0.0 ± 0.0 |
| 4 | 8.5 ± 3.9 | −7.2 ± 3.7 | 12.0 ± 4.0 | −42.5 ± 3.0 | −46.9 ± 6.5 | −46.4 ± 3.7 |
| 7 | 4.5 ± 1.3 | 8.7 ± 13.2 | 8.7 ± 7.7 | −45.7 ± 1.5 | −55.3 ± 6.4 | −46.5 ± 2.7 |
| 8 | 10.3 ± 1.7 | −9.4 ± 4.1 | 3.0 ± 5.1 | −53.2 ± 3.2 | −55.6 ± 4.3 | −2.4 ± 6.8 |
| 11 | 5.0 ± 2.3 | 14.7 ± 11.4 | 1.5 ± 5.7 | −61.5 ± 4.2 | −57.3 ± 5.1 | 4.2 ± 11.2 |
| 13 | 15.4 ± 2.6 | −6.9 ± 3.3 | 28.7 ± 13.8 | −61.4 ± 3.8 | −59.7 ± 6.5 | 1.2 ± 5.7 |
| 16 | 4.2 ± 4.0 | 2.3 ± 3.0 | 9.0 ± 1.4 | −52.2 ± 5.3 | −51.2 ± 4.0 | 2.1 ± 12.1 |
| 18 | 10.2 ± 7.8 | 0.2 ± 2.8 | 6.3 ± 4.8 | −54.9 ± 4.4 | −57.7 ± 4.6 | 2.2 ± 10.0 |
| 20 | 7.8 ± 6.0 | 3.6 ± 2.4 | 5.0 ± 4.5 | −53.8 ± 4.5 | −53.2 ± 4.9 | −20.8 ± 8.1 |
| 24 | 7.6 ± 5.6 | 1.5 ± 2.9 | 11.1 ± 3.2 | −56.4 ± 3.0 | −54.9 ± 4.1 | −26.4 ± 6.8 |
| 28 | 11.1 ± 6.0 | 0.7 ± 2.5 | 10.9 ± 5.0 | −53.9 ± 2.1 | −51.81 ± 4.1 | −5.4 ± 15.0 |
| 31 | 11.7 ± 6.6 | 1.1 ± 2.3 | 5.1 ± 1.8 | −49.6 ± 4.1 | −49.7 ± 2.5 | −23.3 ± 11.7 |

In the second experiment, in order to see whether anti-NGF treatment could relieve thermal hyperalgesia past day 7 post-surgery, anti-NGF REGN268 (100 mg/kg) was injected s.c. at days 7, 14, or 21 post-surgery. Significant pain relief was obtained at all 3 time points compared to IgG1 control (AVASTIN® 100 mg/kg; $p<0.05$) (Table 24, mean percent change from Hargreaves baseline±SEM; 100 mg/kg IgG1 control, n=6; 100 mg/kg REGN268, n=7).

TABLE 24

| Days After | Day 7 | | Day 14 | | Day 21 | |
|---|---|---|---|---|---|---|
| Surgery | IgG1 control | REGN268 | IgG1 control | REGN268 | IgG1 control | REGN268 |
| Baseline | 0.0 ± 0.0 | 0.0 ± 0.0 | 0.0 ± 0.0 | 0.0 ± 0.0 | 0.0 ± 0.0 | 0.0 ± 0.0 |
| Day 5 | −53.5 ± 5.9 | −51.4 ± 5.6 | −60.0 ± 4.8 | −54.2 ± 5.2 | −55.5 ± 5.0 | −55.5 ± 6.0 |
| Day 7 | −55.4 ± 4.4 | −50.0 ± 6.6 | −54.4 ± 6.4 | −47.9 ± 3.6 | −47.2 ± 4.8 | −40.7 ± 8.5 |
| Day 8 | −56.7 ± 3.8 | 17.3 ± 13.5 | −55.3 ± 6.1 | −47.2 ± 3.2 | −47.9 ± 4.7 | −41.2 ± 7.3 |
| Day 10 | −64.3 ± 2.6 | −6.4 ± 7.7 | −52.8 ± 7.2 | −62.9 ± 5.2 | −55.0 ± 6.7 | −45.9 ± 6.9 |
| Day 14 | −66.9 ± 5.1 | −4.9 ± 3.4 | −62.1 ± 5.7 | −59.7 ± 2.1 | −63.8 ± 4.6 | −61.2 ± 3.4 |
| Day 15 | −60.6 ± 4.0 | −1.7 ± 10.5 | −63.0 ± 5.8 | −38.5 ± 7.3 | −54.5 ± 5.0 | −47.1 ± 4.4 |
| Day 17 | −58.9 ± 3.5 | −0.8 ± 10.5 | −58.6 ± 5.7 | 25.2 ± 17.0 | −52.4 ± 5.3 | −48.4 ± 4.5 |
| Day 21 | −54.1 ± 9.6 | 0.9 ± 9.9 | −57.1 ± 4.4 | 2.1 ± 14.8 | −55.8 ± 3.6 | −48.1 ± 5.0 |
| Day 22 | −56.3 ± 4.9 | −1.0 ± 10.0 | −55.4 ± 5.1 | −6.4 ± 7.1 | −50.6 ± 5.3 | −34.0 ± 6.4 |
| Day 24 | −55.6 ± 5.1 | −1.0 ± 10.3 | −49.5 ± 6.6 | −2.1 ± 11.4 | −44.7 ± 5.7 | −3.2 ± 10.8 |
| Day 28 | −54.1 ± 3.5 | −9.0 ± 9.6 | −53.6 ± 5.4 | −1.8 ± 8.5 | −46.0 ± 7.6 | 13.9 ± 12.0 |
| Day 32 | −41.9 ± 8.3 | −29.1 ± 7.1 | −40.9 ± 13.1 | −10.2 ± 8.7 | −32.8 ± 4.8 | 8.0 ± 12.9 |
| Day 35 | −43.9 ± 6.8 | −32.6 ± 7.4 | −42.9 ± 10.3 | −11.8 ± 7.9 | −39.8 ± 4.5 | 12.2 ± 12.4 |
| Day 39 | −42.5 ± 6.9 | −29.0 ± 7.9 | −39.0 ± 11.4 | −11.7 ± 6.7 | −34.6 ± 10.0 | 12.3 ± 10.8 |
| Day 42 | −35.0 ± 6.6 | −26.1 ± 7.6 | −38.1 ± 12.5 | −8.9 ± 8.6 | −33.9 ± 9.9 | 13.5 ± 11.5 |

In the third experiment, the ability of another anti-NGF antibody REGN475 was tested in the Seltzer model. Following the Seltzer surgery, mice were tested at days 5 and 7 post-surgery to confirm that the thermal hyperalgesia had developed. Then, at day 7 post-surgery the mice were injected by s.c. or i.p. routes with REGN475 (50 mg/kg), control mAb RN624 (50 mg/kg) or IgG1 control (AVASTIN®) (50 mg/kg). Significant pain relief was observed with both anti-NGF antibodies in both cohorts of mice, either injected s.c. (Table 25) or i.p. (Table 26), while control IgG1 showed no effect (p<0.001-0.05) (Mean percent change from Hargreaves baseline±SEM; 50 mg/kg IgG1 control, n=7; 50 mg/kg RN624, n=7; 50 mg/kg REGN475, n=7).

TABLE 25

| Days after Surgery | IgG1 control | RN624 | REGN475 |
|---|---|---|---|
| Baseline | 0.0 ± 0.0 | 0.0 ± 0.0 | 0.0 ± 0.0 |
| 5 | −51.2 ± 5.2 | −53.5 ± 6.3 | −55.2 ± 3.5 |
| 7 | −47.6 ± 3.9 | −48.4 ± 6.2 | −50.9 ± 4.3 |
| 8 | −31.1 ± 11.9 | 4.5 ± 9.0 | 10.3 ± 14.1 |
| 9 | −36.7 ± 14.6 | −15.2 ± 8.5 | 8.2 ± 7.2 |
| 12 | −47.2 ± 5.5 | −4.2 ± 12.0 | −20.1 ± 4.3 |
| 15 | −46.7 ± 8.5 | 2.1 ± 10.9 | −14.1 ± 6.1 |
| 19 | −28.6 ± 7.5 | −11.5 ± 12.1 | 3.0 ± 10.9 |
| 22 | −34.9 ± 7.9 | −5.7 ± 9.5 | −13.7 ± 13.4 |

TABLE 26

| Days after Surgery | IgG1 control | RN624 | REGN475 |
|---|---|---|---|
| Baseline | 0.0 ± 0.0 | 0.0 ± 0.0 | 0.0 ± 0.0 |
| 5 | −55.5 ± 3.8 | −56.6 ± 2.3 | −58.7 ± 2.3 |
| 7 | −61.6 ± 1.8 | −62.3 ± 3.4 | −61.7 ± 2.7 |
| 8 | −59.3 ± 4.0 | −3.3 ± 16.0 | −8.2 ± 16.1 |
| 9 | −51.0 ± 4.2 | −18.4 ± 12.9 | −7.9 ± 9.6 |
| 12 | −46.5 ± 6.3 | −7.0 ± 11.8 | −0.1 ± 22.8 |
| 15 | −43.3 ± 6.6 | −16.2 ± 14.8 | −10.8 ± 18.0 |

To determine the ability of antibodies to neutralize human NGF activities in vivo, transgenic mice were made of which the endogenous mouse NGF locus was replaced with the human NGF gene. These mice were used in a Seltzer neuropathic pain model to test REGN268 and control mAbs. Following the Seltzer surgery, these mice were tested at day 4 and at day 8 post-surgery to confirm that the thermal hyperalgesia had developed. Then, at day 8 post-surgery the mice were injected s.c. with 50 mg/kg mAb REGN268 (n=7), 50 mg/kg control RN624 (n=8), or 50 mg/kg IgG1 control (AVASTIN®) (n=6). The results (Table 27) showed that REGN268 was as efficacious as a humanized anti-NGF antibody (RN624) in relieving the neuropathic pain in the humanized NGF mice, whereas IgG1 control had no effect (p<0.05).

TABLE 27

| Days after Surgery | IgG1 Control | RN624 | REGN268 |
|---|---|---|---|
| Baseline | 0.0 ± 0.0 | 0.0 ± 0.0 | 0.0 ± 0.0 |
| 8 | −55.4 ± 5.7 | −38.1 ± 6.4 | −40.8 ± 6.9 |
| 10 | −54.3 ± 8.0 | −23.0 ± 7.7 | −16.8 ± 5.4 |
| 12 | −44.8 ± 7.9 | −18.4 ± 8.4 | −15.1 ± 10.1 |
| 14 | −41.3 ± 7.0 | 5.0 ± 23.6 | −6.7 ± 12.9 |
| 16 | −42.5 ± 8.8 | −12.7 ± 9.5 | 5.2 ± 16.3 |
| 20 | −44.2 ± 8.9 | −15.7 ± 13.0 | −8.0 ± 13.7 |

Example 11

Effect of Anti-NGF on Animal Motor Function

In order to study whether anti-NGF treatment could alter motor function, motor coordination in the rotarod test in naive C57BL/6 male mice was assessed. Animals were first trained to stay on a rotarod (Columbus Instruments, 3.5 cm diameter, 9 cm wide) rotating at progressively higher speeds (maximum speed 10 rpm). Mice remained at 10 rpm in training until they could walk for 60 sec consecutively, or until they had spent a total of 2 min walking on the rotarod at 10 rpm each day for three consecutive days. After training, each mouse was placed on the rotarod at 10 rpm three times consecutively (with a brief break between trials), and the latency to fall off was recorded. Animals were removed after 1 min, and assigned a score of 60 sec if they did not fall off. The median score of 3 trials for each mouse was used in analysis. After obtaining a baseline reading in the rotarod, mAbs REGN475, RN624, or IgG negative control was injected s.c. at 50 mg/kg or 100 mg/kg. The mice were then tested for up to 20 days post-antibody injection. Results (Table 28, expressed as latency to fall in sec) (mean±sem) showed that the mice treated with RN624, but not REGN475, had significantly impaired motor coordination (p<0.001-0.05). Interestingly, it has been reported that NT-3 and TrkC knock-out mice displayed abnormal movements and postures and lost proprioception (Ernfors et al. (1994) Cell 77:503-512; and Klein et al. (1994) Nature 368:249-251). Besides the rotarod, Hargreaves' and von Frey tests on naïve mice injected with anti-NGF antibodies were also conducted. No statistically significant differences were observed for any group of mice in the Hargreaves' and von Frey tests during the 20 days post-antibody administration (n=6 for each group).

TABLE 28

| Time after anti-NGF treatment | 100 mg/kg IgG1 control | 50 mg/kg RN624 | 100 mg/kg RN624 | 50 mg/kg REGN475 | 100 mg/kg REGN475 |
|---|---|---|---|---|---|
| Baseline | 57.7 ± 1.6 | 54.2 ± 4.6 | 60.0 ± 0.0 | 55.0 ± 3.6 | 60.0 ± 0.0 |
| Day 1 | 59.2 ± 0.7 | 43.2 ± 3.7 | 32.8 ± 2.2 | 58.0 ± 1.3 | 58.4 ± 1.5 |
| Day 4 | 52.8 ± 4.8 | 36.3 ± 4.3 | 32.5 ± 3.2 | 52.5 ± 4.3 | 53.2 ± 3.3 |
| Day 7 | 57.7 ± 1.8 | 47.2 ± 3.7 | 37.5 ± 5.2 | 58.0 ± 1.3 | 60.0 ± 0.0 |
| Day 11 | 58.7 ± 1.0 | 50.0 ± 4.7 | 44.7 ± 6.2 | 55.2 ± 2.1 | 60.0 ± 0.0 |
| Day 15 | 57.8 ± 1.6 | 56.7 ± 2.6 | 36.0 ± 1.7 | 55.2 ± 2.2 | 57.7 ± 1.6 |
| Day 20 | 57.8 ± 1.8 | 57.8 ± 1.3 | 45.7 ± 5.0 | 51.8 ± 3.3 | 53.7 ± 3.1 |

Example 12

Treatment of Patient Suffering from Post-Herpetic Neuralgia

A patient who has developed chronic pain at the site of a shingles rash is diagnosed with post-herpetic neuralgia. The patient is treated by administration of therapeutically-effective amount of a pharmaceutically acceptable composition comprising an anti-NGF mAb of the invention. Administration may be by subcutaneous or intravenous injection, at the anti-NGF antibody concentrations of, preferably, between 0.01 to 10 mg/kg body weight. Frequency of treatment may be every 1-12 weeks 8-12 weeks, or as needed. Within several days after administration of the anti-NGF antibody composition, the patient's pain is substantially alleviated. Repeated administration of the anti-NGF mAb composition maintains this pain relief.

Example 13

Treatment of Patient Suffering from Osteoarthritis Pain

A patient suffering from moderate to severe pain caused by osteoarthritis in any joint is treated by administering the therapeutically-effective amount of a pharmaceutically acceptable composition comprising an anti-NGF mAb of the invention. The composition can be administered intravenously at the concentrations of the anti-NGF antibody between 10 pg/kg body weight to 10 mg/kg body weight. Frequency of treatment may be every 1-12 weeks, or as needed. Within several days of the administration of the anti-NGF antibody composition, the patient's pain is substantially alleviated and the patient regains mobility of the affected joint. The treatment can be repeated as long as necessary.

We claim:

1. An isolated nucleic acid molecule encoding a human antibody or antigen-binding fragment thereof that specifically binds human nerve growth factor (NGF), wherein the antibody or antigen-binding fragment thereof comprises the three heavy chain CDRs (HCDR1, HCDR2 and HCDR3) contained within any one of the HCVR amino acid sequences selected from the group consisting of SEQ ID NOs: 100 and 108; and the three light chain CDRs (LCDR1, LCDR2 and LCDR3) contained within any one of the LCVR amino acid sequences selected from the group consisting of SEQ ID NOs: 92, 102 and 110.

2. The isolated nucleic acid molecule of claim 1, wherein the nucleic acid sequence encoding the three heavy chain CDRs is selected from the group consisting of SEQ ID NOs: 99 and 107; and wherein the nucleic acid sequence encoding the three light chain CDRs is selected from the group consisting of SEQ ID NOs: 91, 101 and 109.

3. An isolated nucleic acid molecule encoding a human antibody or antigen-binding fragment thereof that specifically binds human nerve growth factor (NGF), wherein the antibody or antigen-binding fragment thereof comprises a heavy chain variable region (HCVR) selected from the group consisting of SEQ ID NOs:100 and 108.

4. The isolated nucleic acid molecule of claim 3, wherein the nucleic acid sequence encoding the heavy chain variable region is selected from the group consisting of SEQ ID NOs: 99 and 107.

5. An isolated nucleic acid molecule encoding a human antibody or antigen-binding fragment thereof that specifically binds human nerve growth factor (NGF), wherein the antibody or antigen-binding fragment thereof comprises a light chain variable region (LCVR) selected from the group consisting of SEQ ID NOs: 92, 102, and 110.

6. The isolated nucleic acid molecule of claim 5, wherein the nucleic acid sequence encoding the light chain variable region is selected from the group consisting of SEQ ID NOs: 91, 101 and 109.

7. An isolated nucleic acid molecule encoding the human antibody or antigen-binding fragment thereof of claim 1, wherein the antibody or antigen-binding fragment thereof comprises a HCVR having an amino acid sequence selected from the group consisting of SEQ ID NOs: 100 and 108 and a LCVR having an amino acid sequence selected from the group consisting of SEQ ID NOs: 92, 102 and 110.

8. The isolated nucleic acid molecule of claim 7, wherein the nucleic acid sequence encoding the heavy chain variable region is selected from the group consisting of SEQ ID NOs: 99 and 107 and the nucleic acid sequence encoding the light chain variable region is selected from the group consisting of SEQ ID NOs: 91, 101 and 109.

9. The isolated nucleic acid molecule of claim 1 encoding a human antibody or antigen-binding fragment thereof that specifically binds human nerve growth factor (NGF), wherein HCDR1 comprises the amino acid sequence of SEQ ID NO: 86; HCDR2 comprises the amino acid sequence of SEQ ID NO: 88; HCDR3 comprises the amino acid sequence of SEQ ID NO: 90; LCDR1 comprises the amino acid sequence of SEQ ID NO: 94; LCDR2 comprises the amino acid sequence of SEQ ID NO: 96 and LCDR3 comprises the amino acid sequence of SEQ ID NO: 98.

10. The isolated nucleic acid molecule of claim 9, wherein the nucleic acid sequence encoding the HCDR1 is set forth in SEQ ID NO: 85; the nucleic acid sequence encoding the HCDR2 is set forth in SEQ ID NO: 87; the nucleic acid sequence encoding the HCDR3 is set forth in SEQ ID NO: 89; the nucleic acid sequence encoding the LCDR1 is set forth in SEQ ID NO: 93, the nucleic acid sequence encoding the LCDR2 is set forth in SEQ ID NO: 95; and the nucleic acid sequence encoding the LCDR3 is set forth in SEQ ID NO: 97.

11. An isolated nucleic acid molecule encoding the human antibody or antigen-binding fragment thereof of claim 1, wherein the antibody comprises a heavy chain variable region (HCVR) and a light chain variable region (LCVR), wherein the HCVR and LCVR amino acid sequence pairs are selected from the group consisting of SEQ ID NOs: 108 and 92; SEQ ID NOs: 100 and 102; and SEQ ID NOs: 108 and 110.

12. The isolated nucleic acid molecule of claim 11, wherein the nucleic acid sequence pairs encoding the HCVR and LCVR amino acid sequence pairs are selected from the group consisting of SEQ ID NOs: 107 and 91; SEQ ID NOs: 99 and 101 and SEQ ID NOs: 107 and 109.

13. An expression vector comprising the nucleic acid molecule of claim 1.

14. A host cell comprising the vector according to claim 13.

15. A method of producing an anti-human NGF antibody or antigen-binding fragment of an antibody comprising introducing the expression vector of claim 13 into an isolated host cell, growing the cell under conditions permitting production of the antibody or antibody fragment, and recovering the antibody or antibody fragment so produced.

16. The method of claim 15, wherein the host cell is an *E. coli* cell, a CHO cell, or a COS cell.

* * * * *